US012447082B2

(12) United States Patent
Bui et al.

(10) Patent No.: US 12,447,082 B2
(45) Date of Patent: Oct. 21, 2025

(54) DEVICES AND METHODS FOR TRANSFERRING AN OBJECT

(71) Applicant: Able Innovations Inc., Toronto (CA)

(72) Inventors: Ngoc Phuong Bui, Toronto (CA); Philip Chang, York (CA); Trevor Jordan Vaughan, Toronto (CA); Alexandre Lemay, Quebec (CA); Veronica Guthrie, Toronto (CA); Jayiesh Singh, Toronto (CA)

(73) Assignee: Able Innovations Inc. (CA)

( * ) Notice: Subject to any disclaimer, the term of this patent is extended or adjusted under 35 U.S.C. 154(b) by 285 days.

(21) Appl. No.: 18/270,574

(22) PCT Filed: Jan. 12, 2022

(86) PCT No.: PCT/CA2022/050044
§ 371 (c)(1),
(2) Date: Jun. 30, 2023

(87) PCT Pub. No.: WO2022/150915
PCT Pub. Date: Jul. 21, 2022

(65) Prior Publication Data

US 2024/0065908 A1 Feb. 29, 2024

Related U.S. Application Data

(60) Provisional application No. 63/136,348, filed on Jan. 12, 2021.

(51) Int. Cl.
*A61G 7/10* (2006.01)
*A61G 7/08* (2006.01)
(Continued)

(52) U.S. Cl.
CPC ............... *A61G 7/103* (2013.01); *A61G 7/08* (2013.01); *A61G 7/1032* (2013.01);
(Continued)

(58) Field of Classification Search
CPC ........ A61G 1/003; A61G 7/08; A61G 7/1025; A61G 7/1026; A61G 7/103; A61G 7/1032;
(Continued)

(56) References Cited

U.S. PATENT DOCUMENTS 2,528,048 A * 10/1950 Gilleland ............. A61G 7/1046 5/86.1
3,593,351 A * 7/1971 Dove ................... A61G 7/1057 5/88.1
(Continued)

FOREIGN PATENT DOCUMENTS

CN 104856808 B 5/2017
CN 110916940 A 3/2020
(Continued)

OTHER PUBLICATIONS

International Search Report and Written Opinion dated Apr. 12, 2022 issued on corresponding International Application No. PCT/CA2022/050044, 11 pages.

*Primary Examiner* — George Sun
(74) *Attorney, Agent, or Firm* — DENTONS DAVIS BROWN PC; Matthew Warner-Blankenship

(57) ABSTRACT

A transfer device includes a device body, and an articulated transfer platform. The articulated transfer platform include a distal platform segment and a plurality of intermediate platform segments. A distal locking mechanism is releasably securable to a locking mechanism of a lead intermediate platform segment, and locking mechanisms of successive intermediate platform segment are releasably securable to locking mechanisms of preceding intermediate platform segment. In a stowed position, the successive intermediate platform segments are positioned below the lead intermediate platform segment. In an extended position, the distal platform segment is located laterally away from the device
(Continued)

body, the distal locking mechanism is secured to the locking mechanism of the lead intermediate platform segment, and the locking mechanism of a successive intermediate platform segment is secured to the locking mechanism of the lead intermediate platform segment.

47 Claims, 60 Drawing Sheets

(51) Int. Cl.
*A61L 2/10* (2006.01)
*A61L 2/18* (2006.01)
*A61L 2/26* (2006.01)

(52) U.S. Cl.
CPC .............. *A61G 7/1044* (2013.01); *A61L 2/10* (2013.01); *A61L 2/18* (2013.01); *A61L 2/26* (2013.01); *A61L 2202/11* (2013.01); *A61L 2202/15* (2013.01); *A61L 2202/17* (2013.01); *A61L 2202/26* (2013.01)

(58) Field of Classification Search
CPC .. A61G 7/1034; A61G 7/1036; A61G 7/1044; A61G 2203/10; A61G 2203/70; A61L 2/10; A61L 2/18; A61L 2/22; A61L 2/26; A61L 2202/11; A61L 2202/15; A61L 2202/17; A61L 2202/26
See application file for complete search history.

(56) References Cited

U.S. PATENT DOCUMENTS

| | | | | | |
|---|---|---|---|---|---|
| 4,306,343 | A * | 12/1981 | Rochat | H03H 3/02 29/25.35 |
| 5,390,379 | A * | 2/1995 | Palmer, Jr. | A61G 7/1076 5/81.1 C |
| 2005/0066442 | A1* | 3/2005 | Kasagami | A61G 7/1032 5/81.1 C |
| 2007/0079438 | A1* | 4/2007 | Patterson | A61G 7/1019 5/81.1 C |
| 2012/0291196 | A1* | 11/2012 | Konda | A61G 7/1032 5/81.1 C |
| 2014/0306429 | A1* | 10/2014 | Patterson | A61G 7/0528 280/657 |
| 2019/0070054 | A1* | 3/2019 | Tee | A61G 7/103 |
| 2020/0230003 | A1* | 7/2020 | Yochum | A61G 7/1046 |

FOREIGN PATENT DOCUMENTS

| | | | |
|---|---|---|---|
| CN | 111329697 | A | 6/2020 |
| DE | 202015000229 | U1 | 3/2016 |
| JP | S551980-041099 | A | 3/1980 |
| JP | H101998-033593 | A | 2/1998 |
| JP | 2013-525233 | A | 6/2013 |
| KR | 200464739 | Y1 | 1/2013 |
| WO | 2011138607 | A2 | 11/2011 |
| WO | WO 2021072547 | A1 * | 4/2021 |

* cited by examiner

DEVICES AND METHODS FOR TRANSFERRING AN OBJECT

CROSS-REFERENCE TO RELATED APPLICATIONS

This patent application is the U.S. national stage of International Application No. PCT/CA2022/050044 filed on Jan. 12, 2022, which in turn claims the benefit of priority of U.S. Provisional Patent Application No. 63/136,348 filed on Jan. 12, 2021. Both International Application No. PCT/CA2022/050044 and U.S. Provisional Patent Application No. 63/136,348 are hereby incorporated herein by reference in their entirety.

FIELD OF THE DISCLOSURE

This disclosure relates generally to devices and methods for transferring an object from a position on a first surface, onto a platform of the device, and then onto a second surface (or back to the first surface), and more specifically to devices and methods for transferring an object using an articulated transfer platform.

BACKGROUND

Countries around the world are facing an aging problem whereby in the coming decades, the majority of their populations will become dependents rather than of an independent age contributing to society. Coupled with this aging population is a growing number of people that have restricted mobility due to injury, illness, or old age. Being mobile necessitates a means of transportation (from point A to point B) as well as being transferred (from surface A to surface B).

There are various transportation aids that are often used to aid mobility. Examples include walkers, wheelchairs, slings, transfer boards and gantry hoists. Many of these devices have not been updated or improved in decades and as a result, fundamental problems associated with the operation of these transfer methods persist. These included injuries to practitioners, reduced patient health and well-being as a result of interaction with these devices, and induced stress on the health-care sector due to implications of the operation of these devices.

The fact however, is that these devices are greatly needed, as between 30% to 60% of patients in long-term care facilities need assistance with transfer to perform routine tasks such as eating a meal or going to the washroom. Without the aid of these devices, people would remain largely immobile once their health starts to fail. Similar challenges exist when performing routine medical diagnostics or conducting routine transfers with bariatrics patients. In these circumstances some transfers that may be required include (but not limited to), from a gurney to a medical imaging table (e.g. the bed of an MRI or CT scanner), movement of a patient temporarily to perform routine operations (e.g. bed cleaning, obtaining a weight measurement for the patient), or simply re-positioning of their body on their existing surface.

Currently the most popular devices used to assist in patient transfer consist of variations of lifts, slings, and transfer boards and sheets. The lifts among these systems are commonly referred to by their trade name as Hoyer Lifts, Hoyer being a popular manufacturer of these devices. These lifts have been in the market for decades with most innovations focusing on improving or re-packaging existing lift technologies. Current technologies typically place significant strain on a human operator, as they typically require some form of "staging" where a sling (or other strap(s) or harnesses) must be inserted underneath a patient, and then removed from under the patient after a transfer. Furthermore, these devices are often costly and may put heavy burdens on operating budgets of long-term care and health care facilities. These devices are also error prone, which often results in numerous injuries to the individuals being transferred, and in some cases has even resulted in death.

SUMMARY OF THE DISCLOSURE

The following introduction is provided to introduce the reader to the more detailed discussion to follow. The introduction is not intended to limit or define any claimed or as yet unclaimed invention. One or more inventions may reside in any combination or sub-combination of the elements or process steps disclosed in any part of this document including its claims and figures.

Transfer devices as disclosed herein include articulated transfer platforms and a transfer belt that overlies the transfer platforms. The articulated platforms include a series of segments or slats that are coupled to each other in a manner that allows adjacent platform segments to pivot relative to each other.

The disclosed transfer devices may be used to perform a transfer of an object from an initial starting position on a surface, onto the device's platform, and then transfer the said object off again onto the same or a different desired surface. For example, an articulated platform may be extended to a position underneath an object to be transferred (e.g. a human body)—i.e. between the object and a surface on which the object is supported—and then retracted with the object supported by the transfer belt and the articulated platform so that the object is positioned above the body of the transfer device. Additionally, or alternatively, an articulated platform may be extended to transfer an object positioned above the body of the transfer device (i.e. supported on the transfer belt) onto to a remote surface.

Transfer devices with articulated transfer platforms may have one or more advantages. For example, the ability of adjacent platform segments to pivot relative to each other may allow the transfer platform to flex, curve, or otherwise conform to the shape of a lower surface of an object to be transferred (e.g. a human body) and/or to a surface on which the object is resting (e.g. a soft mattress, a padded CT table). The ability of an articulated platform to be deformed in a controlled manner may result in reduced normal forces as it is extended underneath the object. As a result, there may be a lower potential for damage and/or discomfort to the object/patient being transferred.

As another example, articulated transfer platforms may be stored in a relatively small volume when in a retracted configuration. This may allow a transfer device to have a transfer platform that can extend laterally by a length greater than the width of the device body (i.e. when the transfer platform is in a retracted configuration). Put another way, an articulated transfer platform may be retracted/stored in a volumetric space that has a smaller width than the extent of the platform's lateral reach.

As another advantage, a transfer device with articulated transfer platforms may allow an object to be transferred to/from both sides of the device. For example, the transfer device may be positioned between an object to be transferred (e.g. a patient on a hospital bed or gurney) and a surface onto which the object is to be transferred (e.g. a CT or MRI bed). An articulated transfer platform may be extended from one side of the transfer device, used to transfer the object from a first surface (e.g. a hospital gurney) onto a central portion of the transfer device, and then an articulated transfer platform may be extended from the other side of the transfer device, and used to transfer the object from the central portion of the transfer device to a second surface (e.g. a CT bed).

Transfer devices as disclosed herein may be characterized as being mechatronic in nature, e.g. utilizing a mechanical system with computer-controlled, semi-autonomous or full-autonomous control systems and associated control algorithms. Optionally, the control systems may allow a transfer device to perform a transfer operation of the desired object predictably and safely, with consistent repeatability.

In accordance with one broad aspect of this disclosure, there is provided a transfer device comprising: a device body having a first end, a second end, a first side, and a second side; and an articulated transfer platform comprising: a distal platform segment having a first end, a second end, a leading edge extending between the first end and the second end, a trailing edge extending between the first end and the second end, and a distal locking mechanism; a plurality of intermediate platform segments, including a lead intermediate platform segment and one or more successive intermediate platform segments, each intermediate platform segment having a first end, a second end, a first edge extending between the first end and the second end, a second edge extending between the first end and the second end, and an intermediate locking mechanism; wherein the distal locking mechanism is releasably securable to the intermediate locking mechanism of the lead intermediate platform segment, and wherein the intermediate locking mechanism of each successive intermediate platform segment is releasably securable to the intermediate locking mechanism of a preceding intermediate platform segment; and wherein, in a stowed position, the one or more successive intermediate platform segments are positioned below the lead intermediate platform segment, and wherein, in an extended position, the distal platform segment is located laterally away from the device body, the distal locking mechanism is secured to the intermediate locking mechanism of the lead intermediate platform segment, and the intermediate locking mechanism of one of the successive intermediate platform segments is secured to the intermediate locking mechanism of the lead intermediate platform segment.

In some embodiments, the distal locking mechanism is located proximate the first end of the distal platform segment, and for each intermediate platform segment, the intermediate locking mechanism is located proximate the first end of the intermediate platform segment.

In some embodiments, the transfer device further comprises a transfer device controller configured to control the articulated transfer platform.

In some embodiments, the transfer device further comprises a platform lateral actuator operably coupled to the transfer device controller, the platform lateral actuator being configured to selectively move the distal platform segment and intermediate platform segments secured thereto laterally relative to the device body.

In some embodiments, the transfer device further comprises a platform segment support assembly operably coupled to the transfer device controller, the platform segment support assembly being configured to selectively raise the one or more successive intermediate platform segments to bring the intermediate locking mechanism of a raised successive intermediate platform segment into alignment with the intermediate locking mechanism of a preceding intermediate platform segment.

In some embodiments, the transfer device further comprises a platform segment release actuator operably coupled to the transfer device controller, the platform segment release actuator being configured to selectively disengage the locking mechanisms of successive platform segments.

In some embodiments, in the stowed position, the distal platform segment at least partially overlies the device body.

In some embodiments, in the stowed position, the distal platform segment is secured to the lead intermediate platform segment.

In some embodiments, in the stowed position, the successive intermediate platform segments are vertically stacked below the lead intermediate platform segment.

In some embodiments, when the distal platform segment and the intermediate platform segments of the articulated transfer platform are secured to each other to produce secured segments, the secured segments may be pivoted relative to each other by about 1° to 30°, or by about 10° to 20°, or by about 15°.

In some embodiments, when the distal platform segment and the intermediate platform segments of the articulated transfer platform are secured to each other to produce the secured segments, the secured segments are biased towards a neutral alignment in which adjacent segments are generally planar.

In some embodiments, when the distal platform segment and the intermediate platform segments of the articulated transfer platform are secured to each other to produce the secured segments, a magnitude of the bias towards the neutral alignment is selectively adjustable.

In some embodiments, the device body has a width between the first and second sides of the device body, and wherein, in the extended position, a distance between the leading edge of the distal platform segment and the first side of the device body is greater than the width of the device body.

In some embodiments, the width of the device body is about 400 mm to 1000 mm, and wherein, in the extended position, the distance between the leading edge of the distal platform segment and the first side of the device body is about 600 mm to 1400 mm.

In some embodiments, the distal locking mechanism comprises one or more recesses.

In some embodiments, the distal locking mechanism comprises one or more projections.

In some embodiments, the intermediate locking mechanisms comprise one or more projections and one or more recesses.

In some embodiments, the transfer device further comprises a transfer belt having a first end secured to a first driven roller, a second end secured to a second driven roller, the belt extending from the first driven roller, around the leading edge of the distal platform segment, above an upper surface of the articulated transfer platform, and to the second driven roller, wherein the first driven roller and the second driven roller are operably coupled to the transfer device controller.

In some embodiments, the transfer belt is a first transfer belt and the transfer device further comprises a second transfer belt extending below a bottom surface of the articulated transfer platform, wherein the second transfer belt is coupled to an actuator that is operably coupled to the transfer device controller.

In some embodiments, the transfer device further comprises a belt treatment system comprising at least one of: an Ultraviolet (UV) light emitter configured to direct UV light towards at least an upper surface of the transfer belt; a fluid emitter configured to direct at least one of a cleaning fluid and a disinfectant fluid towards at least the upper surface of the transfer belt; and a fluid agitator configured to agitate fluid in a fluid chamber through which the transfer belt is configured to pass.

In some embodiments, the transfer device controller is operatively coupled to the belt treatment system, and the transfer device controller is configured to selectively actuate one or more of the UV light emitter, the fluid emitter, and the fluid agitator concurrently or separately from each other.

In some embodiments, the transfer device further comprises: a platform segment treatment system comprising at least one of: an Ultraviolet (UV) light emitter configured to direct UV light towards at least an upper surface of the one or more successive intermediate platform segments; a fluid emitter configured to direct at least one of a cleaning fluid and a disinfectant fluid towards at least the upper surface of the one or more successive intermediate platform segments; and a fluid agitator configured to agitate fluid in a fluid chamber through which the one or more successive intermediate platform segments are configured to pass.

In some embodiments, the transfer device controller is operatively coupled to the platform segment treatment system, and the transfer device controller is configured to selectively actuate one or more of the UV light emitter, the fluid emitter, and the fluid agitator concurrently or separately from each other.

In some embodiments, the transfer device further comprises a device support structure secured to the device body for supporting the device body above a floor surface, wherein the device support structure is configurable to adjust a height of the device body above the floor surface and/or an angle of the device body.

In some embodiments, the device support structure comprises a plurality of wheels to facilitate translation of the transfer device across the floor surface.

In some embodiments, at least one of the plurality of wheels is driven by a motor, such that the transfer device is able to transport itself across the floor surface.

In some embodiments, the transfer device comprises a plurality of controllable subsystems, and wherein the transfer device controller comprises a plurality of controllers configured to control the articulated transfer platform and all of the controllable subsystems.

In some embodiments, the transfer device comprises a plurality of controllable subsystems, and wherein the transfer device controller comprises a single controller configured to control the articulated transfer platform and all of the controllable subsystems.

In accordance with another broad aspect, there is provided a transfer device comprising: a device body having a first end, a second end, a first side, and a second side; and an articulated transfer platform comprising: a distal platform segment, and a plurality of intermediate platform segments, each platform segment having a first end, a second end, and a segment link positioned at each of the first and second ends, the distal platform segment having a leading edge; wherein the segment links of adjacent platform segments are pivotally coupled to each other, wherein the segment links of adjacent platform segments are configured to be selectively restrained in an aligned position; wherein, in a stowed position, the platform segments of the articulated transfer platform are engaged with an internal track of the device body, wherein, as the articulated transfer platform is extended from the stowed position, the distal platform segment is extended laterally away from the device body and the segment links of successive platform segments are restrained in the aligned position upon exiting the internal track, and wherein, as the articulated transfer platform is retracted, the segment links of successive platform segments are unrestrained from the aligned position upon entering the internal track.

In some embodiments, the transfer device further comprises a transfer device controller configured to control the articulated transfer platform.

In some embodiments, the articulated transfer platform is a first articulated transfer platform, the distal platform segment is a first distal platform segment, the intermediate platform segments are first intermediate platform segments, the internal track is a first internal track, and the transfer device further comprises: a second articulated transfer platform comprising: a second distal platform segment, and a plurality of second intermediate platform segments, each second platform segment having a first end, a second end, and a segment link positioned at each of the first and second ends, the second distal platform segment having a leading edge; wherein the segment links of adjacent second platform segments are pivotally coupled to each other, and wherein the segment links of adjacent second platform segments are configured to be selectively restrained in an aligned position; wherein, in a stowed position, the platform segments of the second articulated transfer platform are engaged with a second internal track of the device body, wherein, as the second articulated transfer platform is extended from the stowed position, the second distal platform segment is extended laterally away from the device body and the segment links of successive second platform segments are restrained in the aligned position upon exiting the second internal track, and wherein, as the second articulated transfer platform is retracted, the segment links of successive second platform segments are unrestrained from the aligned position upon entering the second internal track.

In accordance with another broad aspect, there is provided a transfer device comprising: a device body having a first side and a second side; and an articulated transfer platform comprising: a first distal platform segment, a plurality of intermediate platform segments, and a second distal platform segment, each platform segment having a first end, a second end, and a segment link positioned at each of the first and second ends, and each distal platform segment having a leading edge; wherein the segment links of adjacent platform segments are pivotally coupled to each other, and are configured to be selectively restrained in an aligned position; wherein, in a stowed position, the platform segments of the articulated transfer platform are engaged with an internal track of the device body; wherein, as the articulated transfer platform is extended from the first side of the device body, the first distal platform segment is extended laterally away from the device body and the segment links of successive intermediate platform segments are restrained in the aligned position upon exiting the internal track; wherein, as the articulated transfer platform is extended from the second side of the device body, the second distal platform segment is extended laterally away from the device body and the segment links of successive intermediate platform segments are restrained in the aligned position upon exiting the internal track; and wherein, as intermediate platform segments enter the internal track, their segment links are unrestrained from the aligned position.

In some embodiments, the transfer device further comprises a transfer device controller configured to control the articulated transfer platform.

In some embodiments, the transfer device further comprises: a transfer belt having a first end secured to a first driven roller, a second end secured to a second driven roller, the belt extending from the first driven roller, around the leading edge of the first distal platform segment, above an upper surface of the articulated transfer platform, and to the second driven roller, wherein the first driven roller and the second driven roller are operably coupled to the transfer device controller.

In some embodiments, the transfer belt is a first transfer belt and the transfer device further comprises a second transfer belt extending below a bottom surface of the articulated transfer platform on the first side of the device body, and a third transfer belt extending below a bottom surface of the articulated transfer platform on the second side of the device body, wherein the second transfer belt and the third transfer belt are coupled to actuators that are operably coupled to the transfer device controller.

In some embodiments, the transfer device further comprises: an engagement plate positioned proximate an end of the internal track, the engagement plate being configured to restrain adjacent segment links as they pass the engagement plate as the articulated transfer platform is extended, and configured to unrestrain adjacent segment links as they pass the engagement plate as the articulated transfer platform is retracted.

In some embodiments, the transfer device further comprises: a first engagement plate positioned proximate a first end of the internal track, and a second engagement plate positioned proximate a second end of the internal track, the first and second engagement plates being configured to restrain adjacent segment links as they exit the internal track, and to unrestrain adjacent segment links they enter the internal track.

In some embodiments, the device body has a width between the first and second sides of the device body, and wherein, when the articulated transfer platform is fully extended from the first side of the device body, a distance between the leading edge of the first distal platform segment and the first side of the device body is greater than the width of the device body.

In some embodiments, the transfer device further comprises: a belt treatment system comprising at least one of: an Ultraviolet (UV) light emitter configured to direct UV light towards at least an upper surface of the transfer belt; a fluid emitter configured to direct at least one of a cleaning fluid and a disinfectant fluid towards at least the upper surface of the transfer belt; and a fluid agitator configured to agitate fluid in a fluid chamber through which the transfer belt is configured to pass.

In some embodiments, the transfer device controller is operatively coupled to the belt treatment system, and wherein the transfer device controller is configured to selectively actuate one or more of the UV light emitter, the fluid emitter, and the fluid agitator concurrently or separately from each other.

In some embodiments, the transfer device further comprises: a platform segment treatment system comprising at least one of: an Ultraviolet (UV) light emitter configured to direct UV light towards at least an upper surface of the one or more successive intermediate platform segments; a fluid emitter configured to direct at least one of a cleaning fluid and a disinfectant fluid towards at least the upper surface of the one or more successive intermediate platform segments; and a fluid agitator configured to agitate fluid in a fluid chamber through which the one or more successive intermediate platform segments are configured to pass.

In some embodiments, the transfer device controller is operatively coupled to the platform segment treatment system, and wherein the transfer device controller is configured to selectively actuate one or more of the UV light emitter, the fluid emitter, and the fluid agitator concurrently or separately from each other.

In some embodiments, the transfer device further comprises a device support structure secured to the device body for supporting the device body above a floor surface, wherein the device support structure is configurable to adjust a height of the device body above the floor surface and/or an angle of the device body.

In some embodiments, the device support structure comprises a plurality of wheels to facilitate translation of the transfer device across the floor surface.

In some embodiments, at least one of the plurality of wheels is driven by a motor, such that the transfer device is able to transport itself across the floor surface.

In some embodiments, the transfer device comprises a plurality of controllable subsystems, and wherein the transfer device controller comprises a plurality of controllers configured to control the articulated transfer platform and all of the controllable subsystems.

In some embodiments, the transfer device comprises a plurality of controllable subsystems, and wherein the transfer device controller comprises a single controller configured to control the articulated transfer platform and all of the controllable subsystems.

It will be appreciated by a person skilled in the art that a method or apparatus disclosed herein may embody any one or more of the features contained herein and that the features may be used in any particular combination or sub-combination.

These and other aspects and features of various embodiments will be described in greater detail below.

BRIEF DESCRIPTION OF THE DRAWINGS

For a better understanding of the described embodiments and to show more clearly how they may be carried into effect, reference will now be made, by way of example, to the accompanying drawings in which.

Figure 1:
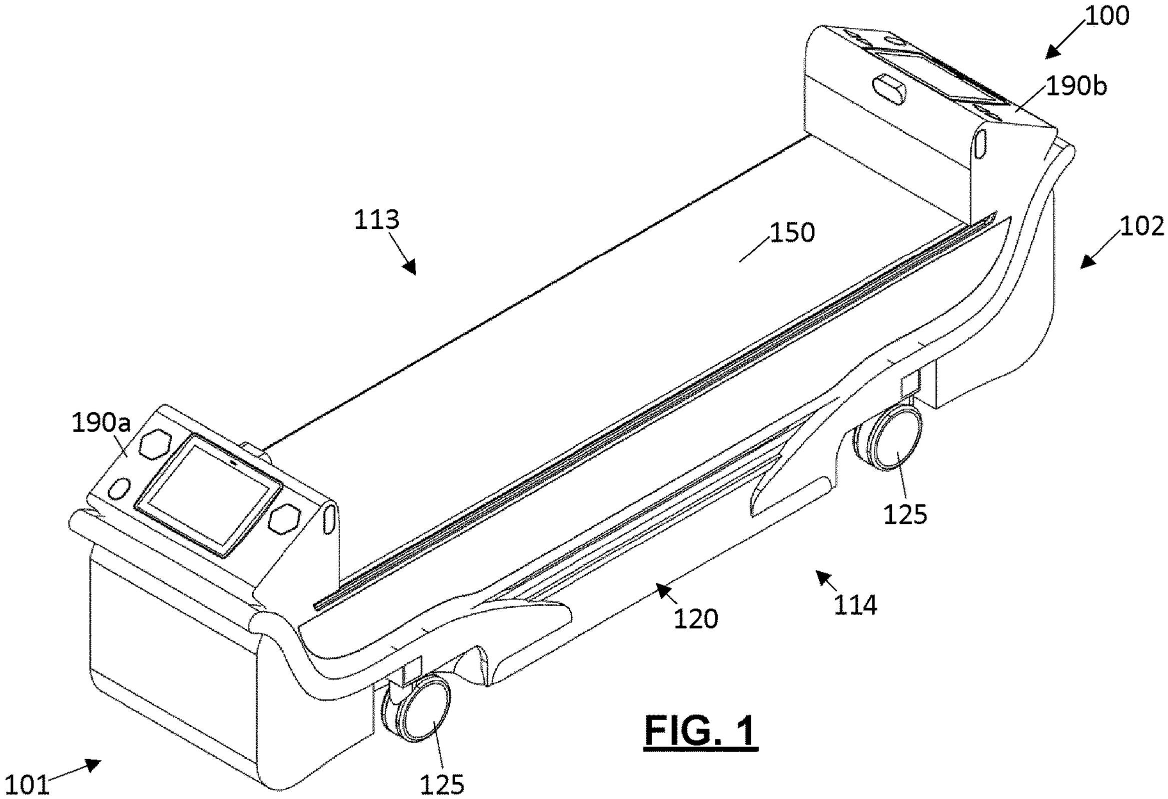
FIG. 1 is a perspective view of a transfer device in accordance with one embodiment.

The drawings included herewith are for illustrating various examples of articles, methods, and apparatuses of the teaching of the present specification and are not intended to limit the scope of what is taught in any way.

DETAILED DESCRIPTION OF EMBODIMENTS

Various apparatuses, methods and compositions are described below to provide an example of an embodiment of each claimed invention. No embodiment described below limits any claimed invention and any claimed invention may cover apparatuses and methods that differ from those described below. The claimed inventions are not limited to apparatuses, methods and compositions having all of the features of any one apparatus, method or composition described below or to features common to multiple or all of the apparatuses, methods or compositions described below. It is possible that an apparatus, method or composition described below is not an embodiment of any claimed invention. Any invention disclosed in an apparatus, method or composition described below that is not claimed in this document may be the subject matter of another protective instrument, for example, a continuing or divisional patent application, and the applicant(s), inventor(s) and/or owner(s) do not intend to abandon, disclaim, or dedicate to the public any such invention by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

Overview of Transfer Device

FIGS. 1 to 36 illustrate example embodiments of a transfer device 100, which can be used to move a human body (or object) from a first location to a second location and/or to re-position the human body (or object) on a surface. An overview of the transfer device 100 is provided in this section with reference to a subset of the drawings. It is to be understood at the outset that the transfer device 100 is shown with very specific features for exemplary purposes only. Other implementations are possible and are within the scope of the disclosure.

Figure 2:
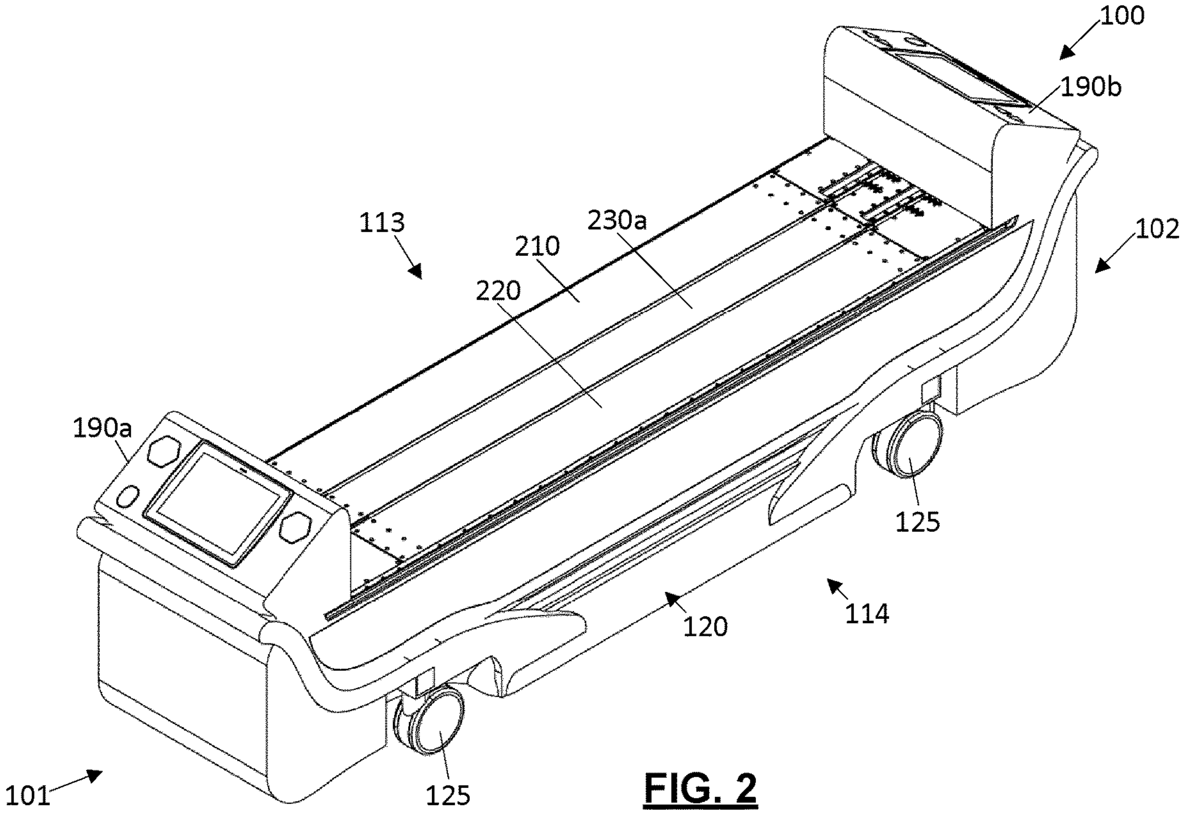
FIG. 2 is a perspective view of the transfer device of FIG. 1, with a transfer belt omitted for clarity.

With reference to FIGS. 1 and 2, the transfer device 100 has a device body 110 having a first end 101, a second end 102, a first side 113, and a second side 114. The transfer device 100 also has platform segments 210, 220 and 230*a-h* that can form an articulated transfer platform. In some implementations, the transfer device 100 has a transfer belt 150 covering the platform segments 210, 220 and 230*a-h* as shown in FIG. 1. Note that the transfer belt 150 has been removed from FIG. 2 for clarity and to reveal the platform segments 210, 220 and 230*a-h*.

Figure 10:
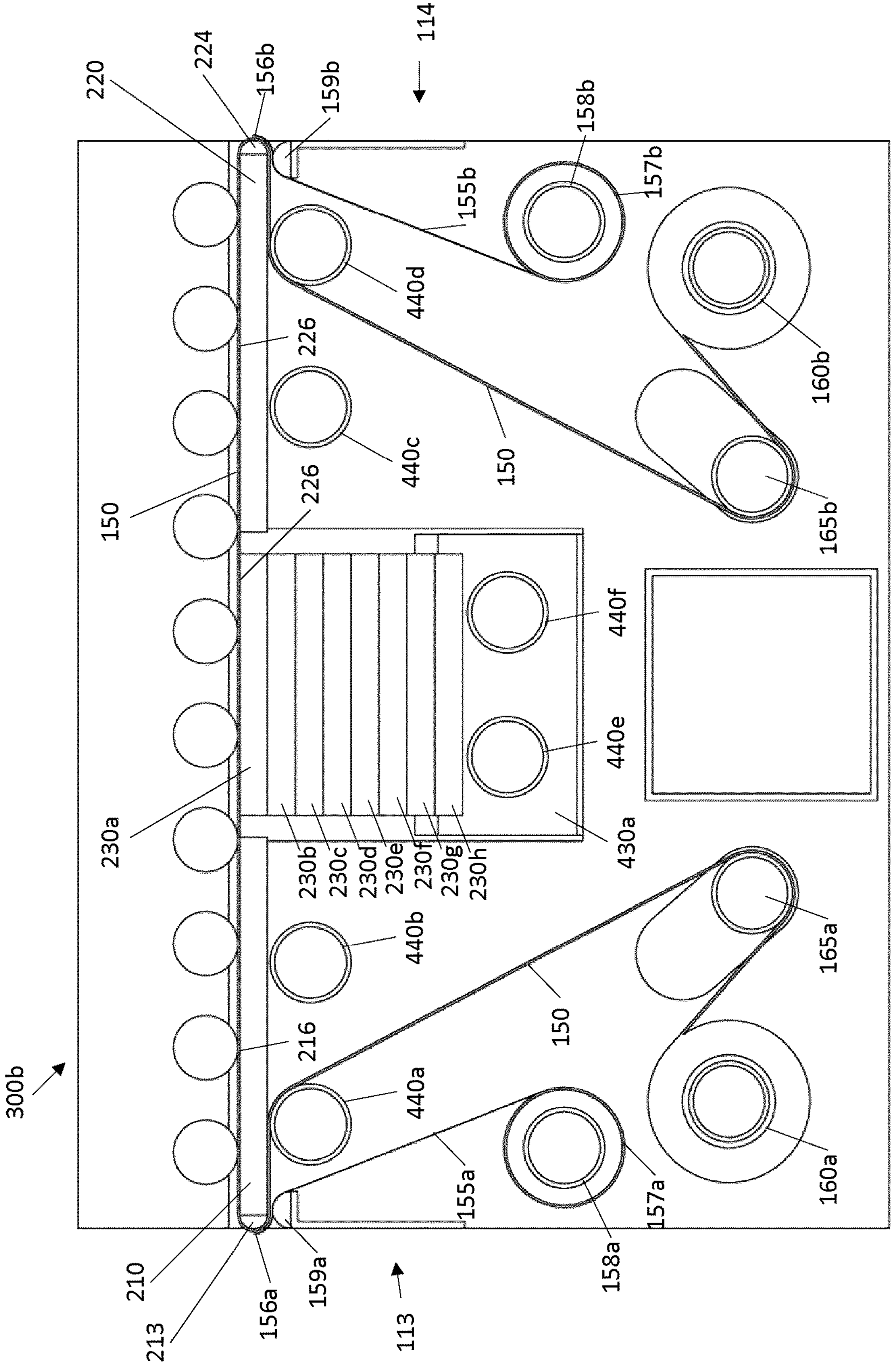
FIG. 10 is a schematic view of a transfer belt path of the transfer device of FIG. 1.

In some implementations, the platform segments 210, 220 and 230*a-h* of the articulated transfer platform include a first distal platform segment 210, a second distal platform segment 220, and a plurality of intermediate platform segments 230*a-h*. However, only one of the intermediate platform segments 230*a-h* is visible in FIG. 2, namely a lead intermediate platform segment 230*a*. With reference to FIG. 10, all other intermediate platform segments 230*b-h* are shown in a stacked configuration beneath the lead intermediate platform segment 230*a*, and hence they are not visible in FIG. 2.

Figure 7:
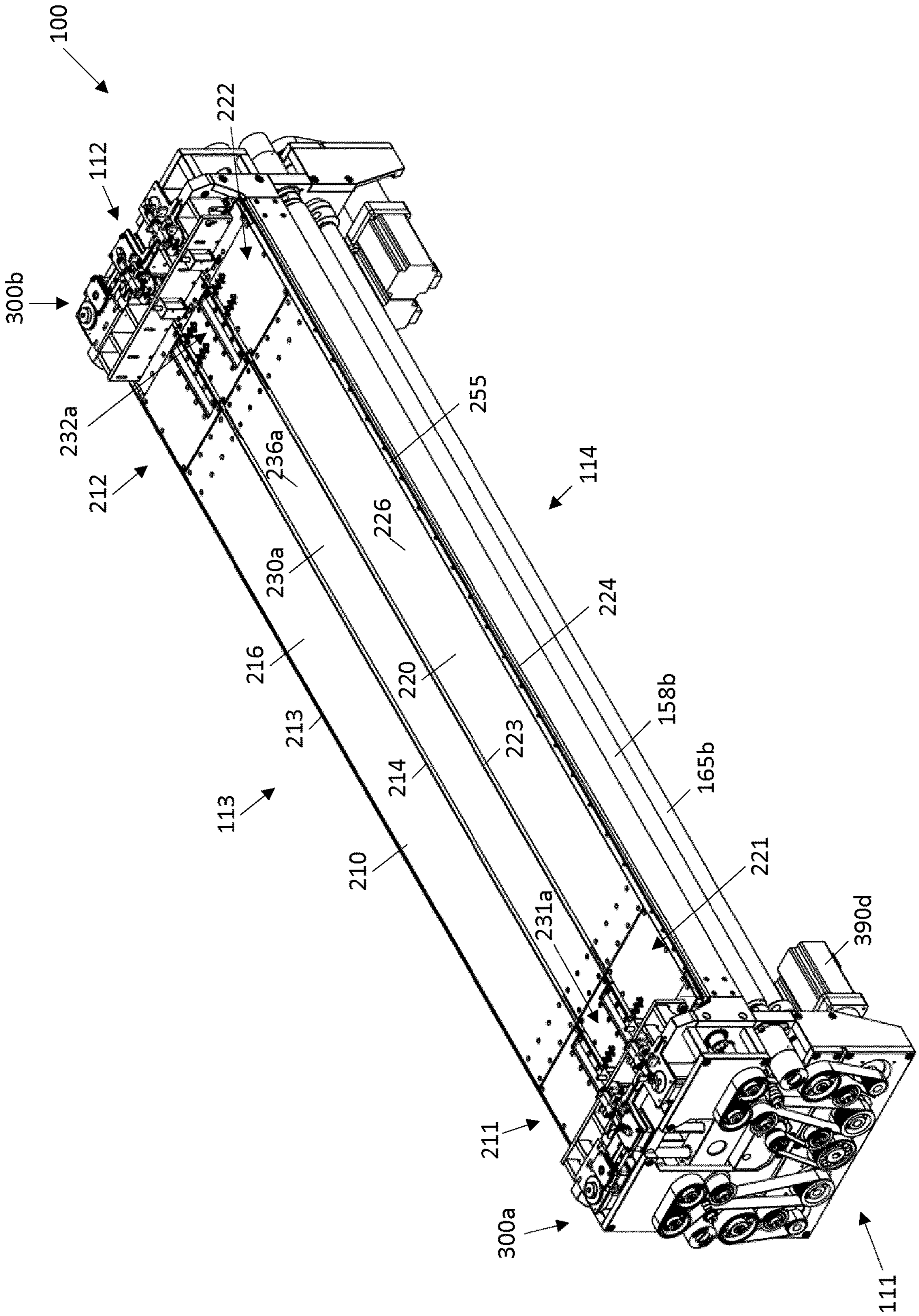
FIG. 7 is a perspective view of the transfer device of FIG. 6, with a transfer belt omitted for clarity.
Figure 8:
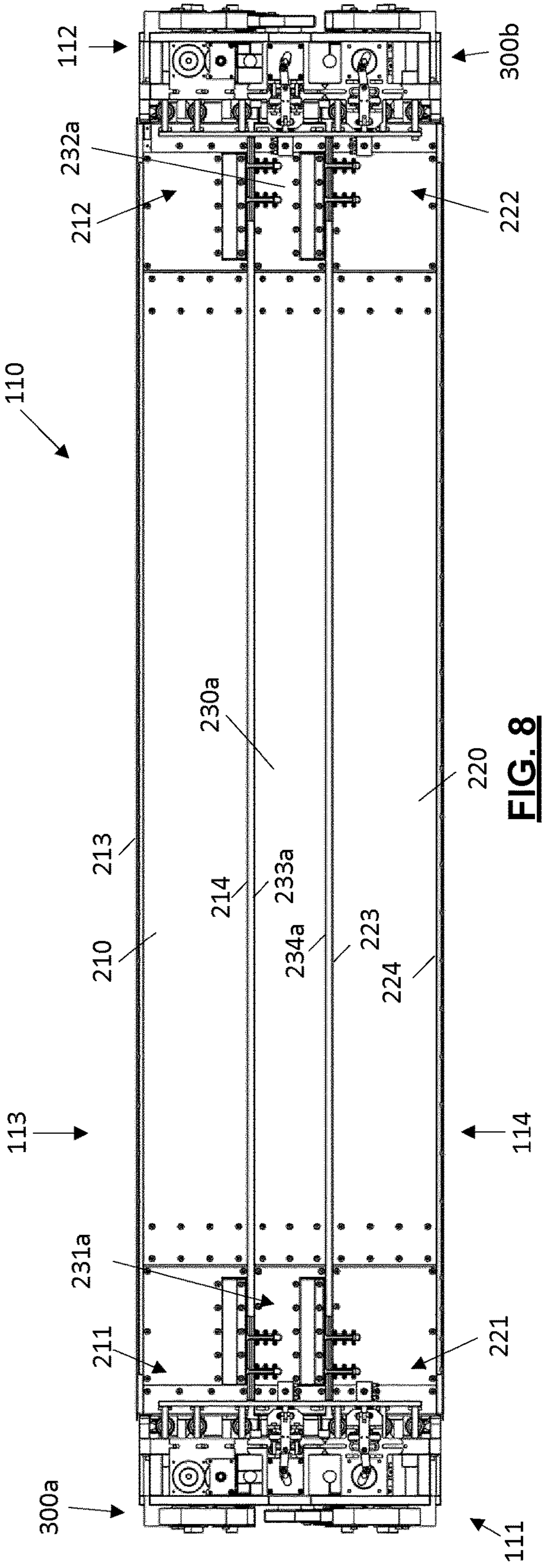
FIG. 8 is a top plan view of the transfer device of FIG. 7.
Figure 9:
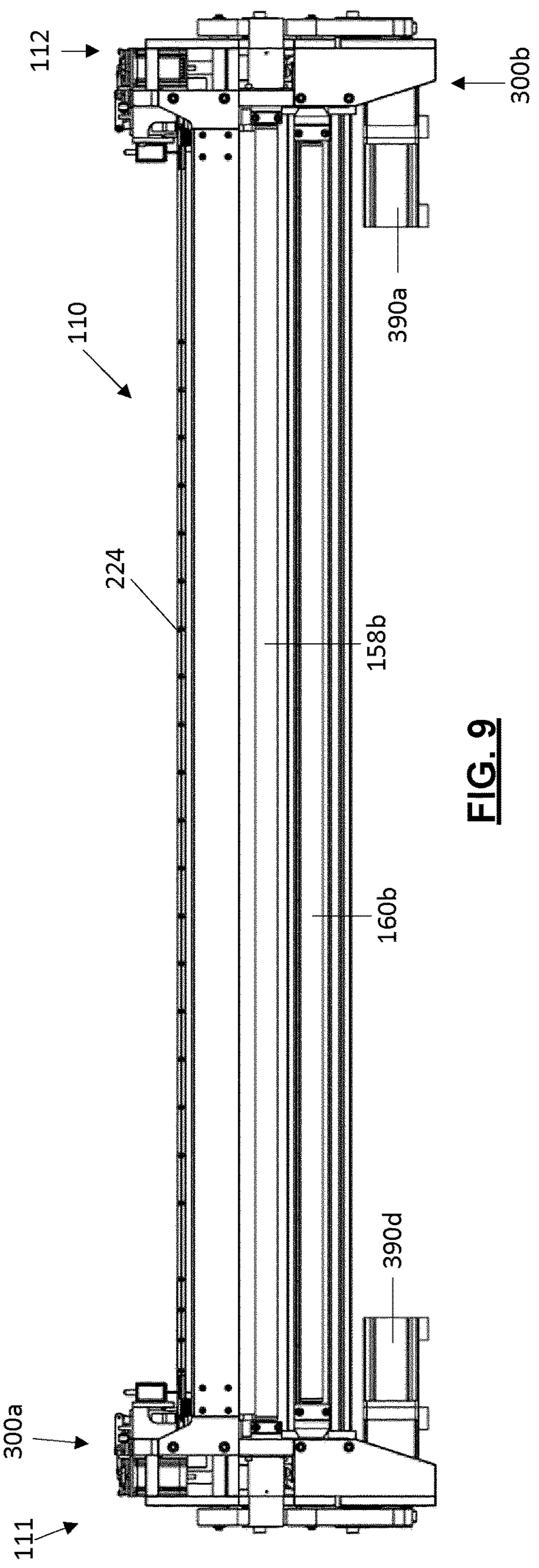
FIG. 9 is a side plan view of the transfer device of FIG. 7.

With reference to FIGS. 7 and 8, positioning and orientation of the platform segments 210, 220 and 230*a-h* can be seen. The first distal platform segment 210 has a first end 211, a second end 212, a leading edge 213 positioned adjacent the first side 113 of the device body 110. The second distal platform segment 220 has a first end 221, a second end 222, and a leading edge 224 positioned adjacent the second side 114 of the device body 110. The lead intermediate platform segment 230*a* has a first end 231*a*, a second end 232*a*, a first side 233*a* positioned adjacent a trailing edge 214 of first distal platform segment 210, and a second side 234*a* positioned adjacent a trailing edge 223 of the second distal platform segment 220.

Figure 3A:
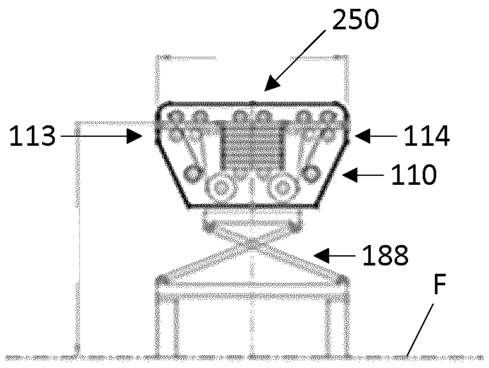
FIG. 3A is a schematic end view of the transfer device of FIG. 1, with a transfer platform in a retracted position.
Figure 3B:
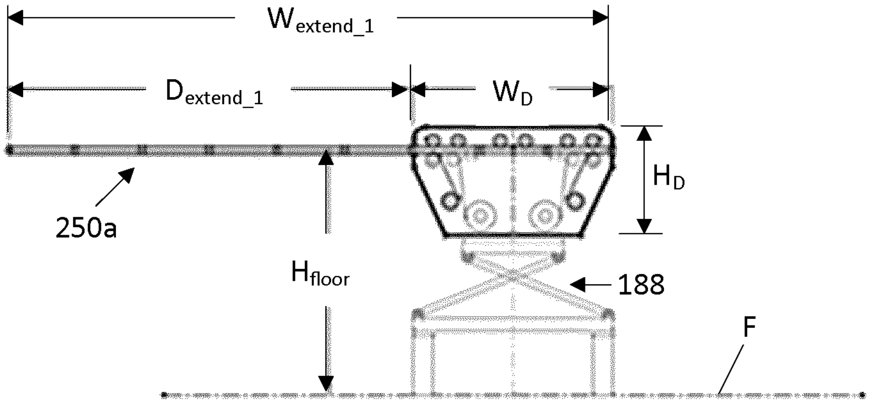
FIG. 3B is a schematic end view of the transfer device of FIG. 1, with a transfer platform in an extended position to a first side of the transfer device.
Figure 3C:
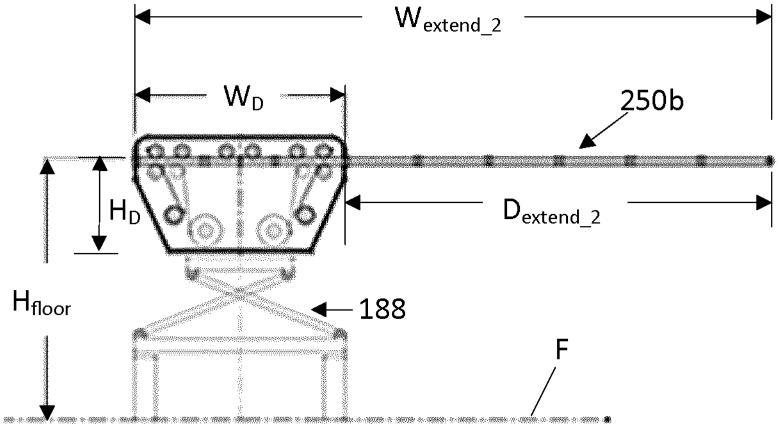
FIG. 3C is a schematic end view of the transfer device of FIG. 1, with a transfer platform in an extended position to a second side of the transfer device.
Figure 4:
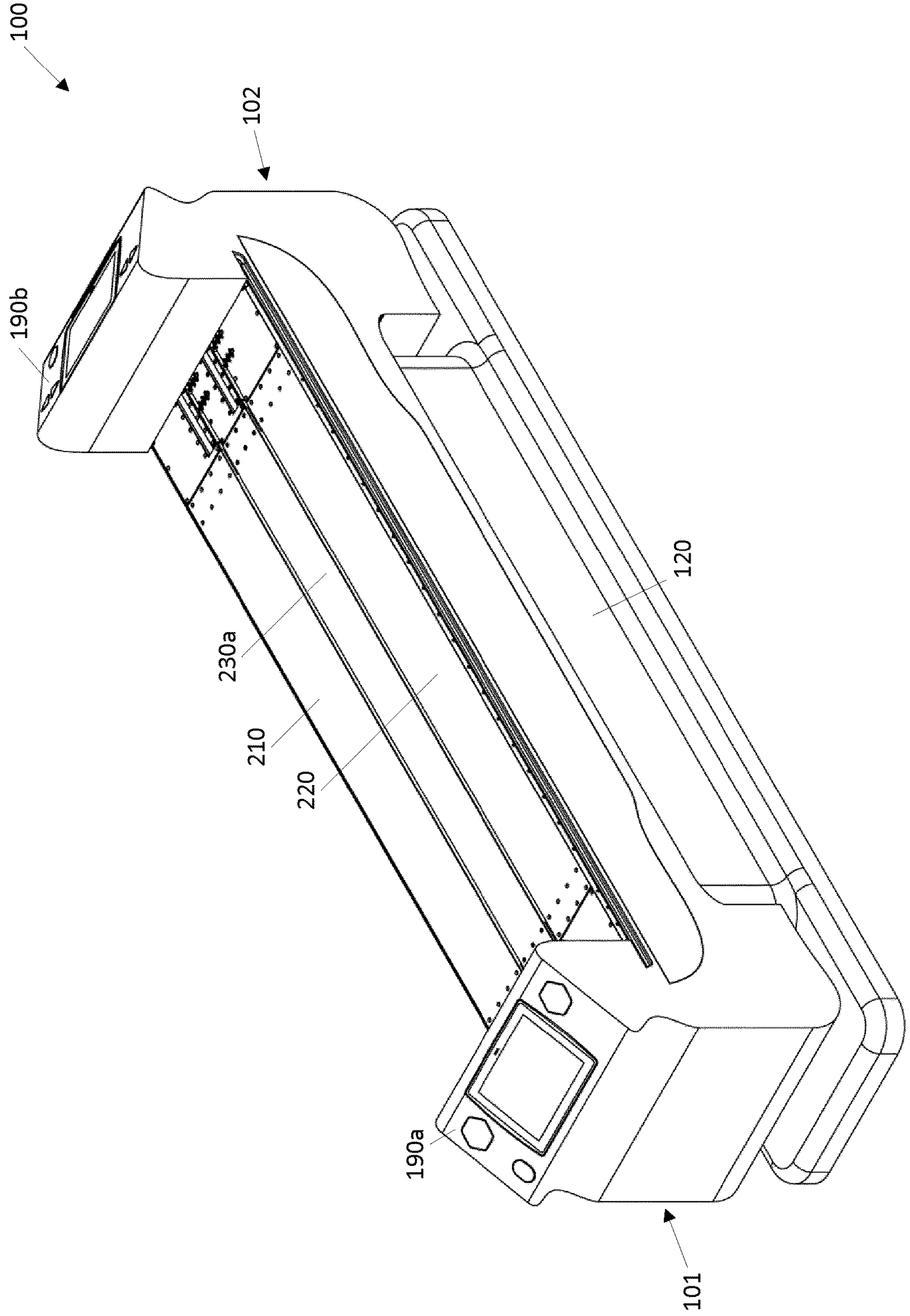
FIG. 4 is a perspective view of a transfer device in accordance with another embodiment, with a transfer belt omitted for clarity.

With reference to FIGS. 3A to 3C, an example operation of the transfer device 100 is illustrated schematically, showing how an articulated transfer platform 250 can be extended outward using the platform segments 210, 220 and 230*a-h*. In the position shown in FIG. 3A (which may be referred to as a stowed position or as a retracted position), the intermediate platform segments 230*b-h* are positioned centrally within the device body 110, and below the lead intermediate platform segment 230*a*, for example in the stacked configuration depicted in FIG. 10.

In the position shown in FIG. 3B, an articulated transfer platform 250*a* has been extended or 'built out' from the first side 113 of the device body 110. As described further below, the articulated transfer platform 250*a* may be 'built out' by securing the first edge 233*a* of the lead intermediate platform segment 230*a* to the trailing edge 214 of first distal platform segment 210, laterally moving the first distal platform segment 210 and the lead intermediate platform segment 230*a* outwardly, and connecting successive intermediate platform segments 230*b-h* to each other as the transfer platform 250*a* is extended.

In the position shown in FIG. 3C, an articulated transfer platform 250*b* has been extended or 'built out' from the second side 114 of the device body 110. In this example, the articulated transfer platform 250*b* may be 'built out' by securing the second edge 234*a* of the lead intermediate platform segment 230*a* to the trailing edge 223 of the second distal platform segment 220, laterally moving the second distal platform segment 220 and lead intermediate platform segment 230*a* outwardly, and connecting successive intermediate platform segments 230*b-h* to each other as the transfer platform 250*b* is extended.

In some implementations, some or all of the platform segments 210, 220 and 230*a-h* have a locking mechanism to enable adjacent segments 210, 220 and 230*a-h* to lock together when they are extended outward from the device body 110. In this way, the articulated transfer platform 250*a* or 250*b* has structural support to impart an outward force when being extended or 'built out' from the device body 110. In addition, the locking mechanism can unlock the platform segments 210, 220 and 230*a-h* so that they can be retracted, thereby enabling a relatively compact design for the transfer deice 100 when in the stowed position or retracted position. Thus, the combination of the platform segments 210, 220 and 230*a-h* and the locking mechanisms enable both (i) the articulated transfer platform 250*a* or 250*b* to have the structural support when being extended outward and (i) the articulated transfer platform 250*a* or 250*b* to be retracted in a manner that enables the relatively compact design.

In some implementations, the distal platform segment has a distal locking mechanism located proximate the first end of the distal platform segment, and each intermediate platform segment has an intermediate locking mechanism located proximate the first end of the intermediate platform segment. However, other locations for the distal locking mechanism and the intermediate locking mechanism are possible and are within the scope of the disclosure. In some implementations, the distal locking mechanism is releasably securable to the intermediate locking mechanism of the lead intermediate platform segment, and the intermediate locking mechanisms of each successive intermediate platform segment are releasably securable to the intermediate locking mechanism of a preceding intermediate platform segment.

In some implementations, in the stowed position, the one or more successive intermediate platform segments are positioned below the lead intermediate platform segment, for example in the stacked configuration depicted in FIG. 10. In some implementations, in an extended position, the distal platform segment is located laterally away from the device body, the distal locking mechanism is secured to the intermediate locking mechanism of the lead intermediate platform segment, and the intermediate locking mechanism of one of the successive intermediate platform segments is secured to the intermediate locking mechanism of the lead intermediate platform segment.

With reference again to FIGS. 3A to 3C, the device body 110 has a width $W_D$ and a height $H_D$. The device body 110 can be supported above a floor service F by a distance $H_{floor}$. In some implementations, as shown in FIG. 3B, the articulated transfer platform 250*a* may be extended by an extended or cantilevered distance $D_{extend\_1}$ from the first edge 113 of the device body 110, providing an overall platform width $W_{extend\_1}$. In some implementations, as shown in FIG. 3C, the articulated transfer platform 250*b* may be extended by an extended or cantilevered distance $D_{extend\_2}$ from the second edge 114 of the device body 110, providing an overall platform width $W_{extend\_2}$.

In some implementations, as can be seen from FIGS. 3A to 3C, the extended distance $D_{extend\_1}$ of articulated transfer platform 250 is greater than the width $W_D$ of the device body 110. In some implementations, the articulated transfer platform 250 can extend by at least twice the width of the device body 110. For example, if the width of the device body 110 is about $W_D$=480 millimeters, the articulated transfer platform 250 can preferably extend by a distance of about $D_{extend\_1}$=800 millimeters, providing an overall platform width of about $W_{extend\_1}$=1280 millimeters. In another implementation, a transfer device that has a device body with a width of about 800 millimeters may have an articulated transfer platform that can extend its leading edge outwardly by about 1200 millimeters from the edge of the device body. More generally, in some implementations, a transfer device that has a device body with a width of about 400 to 1000 millimeters may have an articulated transfer platform that can extend its leading edge outwardly by about 600 to 1400 millimeters from the edge of the device body.

Enabling the articulated transfer platform 250*a* to extend by at least twice the width of the device body 110 may have one or more advantages. For example, this may facilitate maneuvering the transfer device 100 through tight hallways, and/or may reduce the storage footprint of the transfer device when the articulated transfer platform is retracted. This is made possible by the combination of the platform segments 210, 220 and 230*a-h* and the locking mechanisms as noted above.

A relatively narrow width $W_D$ can advantageously facilitate maneuvering the transfer device 100 and/or reduce its storage footprint. However, in some cases it may be desirable for the transfer device 100 to have a supported (i.e. non-cantilevered) surface that has a relatively wider width $W_D$. For example, the device body 110 can have a wider non-cantilevered support surface to provide increased comfort and/or safety when transporting a patient between locations by moving the transfer device 100 across a floor surface.

The examples described above focus on embodiments of the transfer device 100 implementing the articulated transfer platform using the platform segments 210, 220 and 230*a-h* which can be releasably securable to one another via the locking mechanisms. However, in other embodiments, the platform segments 210, 220 and 230*a-h* are pivotally coupled to each other (e.g. using segment links) and can move within in an internal track. For such embodiments, the platform segments 210, 220 and 230*a-h* are configured to be selectively restrained in an aligned position upon exiting the internal track, and conversely are unrestrained from the aligned position when entering the internal track. In the stowed position, the intermediate platform segments may not be in the stacked configuration depicted in FIG. 10, but rather would be positioned within the internal track.

In some implementations, the transfer device 100 has a support structure 188 configurable to adjust a height of the device body 110 above the floor surface F and/or an angle of the device body 110. In some implementations, the support structure 188 can adjust height and tilt of the device body 110 in both the long and short axis. In some implementations, the support structure 188 has actuators coupled to a transfer device controller for controlling the height and/or the tilt of the device body 110. This can allow for changes in an angle of approach of the articulated transfer platform in advance of or during transfer in order to reduce reactionary forces on the device, reduce the pressure applied to the patient (or object) being transferred or allow for medically advantageous positions when a patient is on the transfer platform such as Trendelenburg or reverse Trendelenburg position. The actuation of these support actuators may be controlled by a main transfer device controller or separately by its own controller and operate in parallel through electronic communication with the transfer controller.

In the illustrated example, the platform segments 210, 220 and 230*a-h* include both the first distal platform segment 210 and the second distal platform segment 220, and the articulated transfer platform 250*a* and 250*b* is capable of extending outward in two directions (i.e. the articulated transfer platform 250*a* can extend outward in a first direction as shown in FIG. 3B, and the articulated transfer platform 250*b* can extend outward in a second direction as shown in FIG. 3C. In other implementations, the segments 210, 220 and 230*a-h* include only one distal platform segment and is capable of extending outward in only one direction. Other implementations are possible.

In some implementations, the transfer device 100 has a transfer device controller, which can control one or more actuators (e.g. motors) to extended or retract the articulated transfer platform 250*a* or 250*b* and/or control slack of the transfer belt 150. In some implementations, the transfer device controller is coupled to one or more sensors of the transfer device 100, and utilizes data from the sensors when operating the transfer device 100. In some implementations, the controller synchronizes and directly controls the transfer device 100 with its subsystems, provides feedback to the user in regards to a state of the transfer device 100, and uses the state it is monitoring in order to provide safe operation (e.g. shutting the system down automatically if the transfer device 100 is operating in an unsafe manner).

In some implementations, the transfer device controller is a single controller (e.g. single microcontroller) configured to handle all controllable subsystems of the transfer device 100. In other implementations, the transfer device controller includes multiple controllers (e.g. separate microcontrollers) for handling the controllable subsystems of the transfer device 100. Thus, the term "transfer device controller" covers one or more controllers (e.g. one or more microcontrollers). The purpose for utilizing more than one controller may be to reduce sensor transmission lengths, increase redundancy and/or locate the controllers advantageously, physically within the transfer device 100 to reduce latency. Multiple controllers may also be utilized due to practical limitations of current state of the art controllers (e.g. number of available General Purpose Input Outputs). For example, a first controller may be placed on the first end 101 and a second controller may be placed the second end 102 to capture signals from sensors mounted on each end independently.

There are many possibilities for the controllable subsystems of the transfer device 100. As described herein, some possibilities for the controllable subsystems can include platform lateral actuator(s), a platform segment support assembly, a platform segment release actuator, driven roller(s) for transfer belt(s), a belt treatment system, and/or a platform segment treatment system. Additional or other controllable subsystems may be possible.

Figure 5:
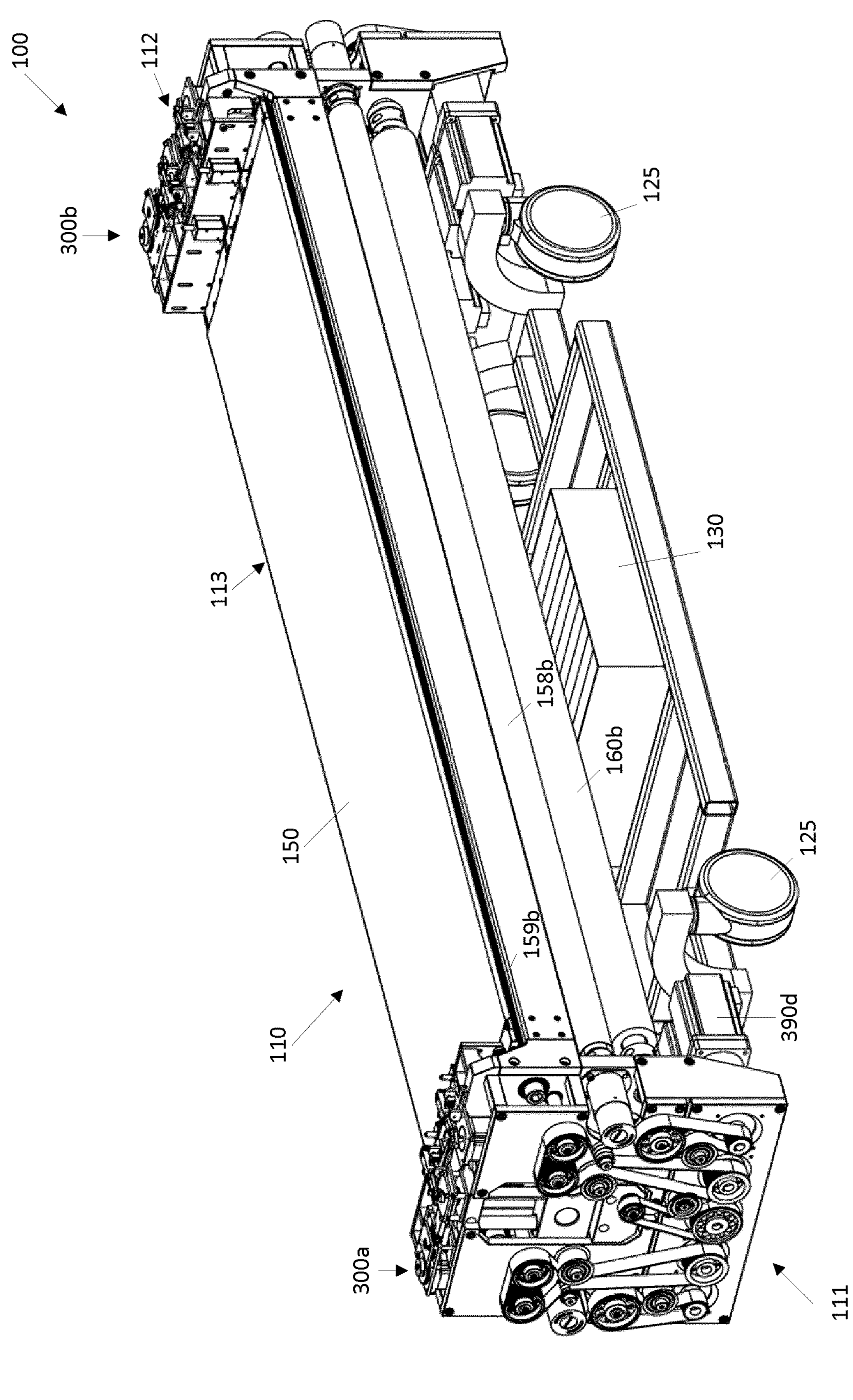
FIG. 5 is a perspective view of the transfer device of FIG. 1, with housing portions omitted for clarity.

In some implementations, the one or more actuators controlled by the transfer device controller are powered via a battery, which can help to enable the transfer device 100 to be portable. For example, with reference to FIG. 5, shown is the transfer device 100 with the housing and the control panels 190 removed for clarity and to reveal a battery pack 130 that can supply power to the transfer device controller, actuators (e.g. motors), etc. of the transfer device 100. Alternatively, a battery pack may not be provided, and transfer device 100 may be connected to an external source of electrical power.

In some implementations, the transfer device 100 has at least one control panel coupled to the transfer device controller to allow a user to operate the transfer device 100. For example, with reference back to FIGS. 1 and 2, the transfer device 100 has two control panels 190*a*, 190*b*, including one control panel 190*a* at the first end 101 of the device body 110, and another control panel 190*b* at the second end 102 of transfer device 100. It will be appreciated that, in other implementations, there may be only one control panel. Alternatively, or additionally, the transfer device 100 may be configured to be controlled from a remote device (e.g. pendant or tethered remote control, a mobile computing device, such as a tablet or laptop computer, or a control panel positioned elsewhere in a room in which the transfer device is positioned, or in an adjacent room), in which case the transfer device 100 could have no control panel.

In some implementations, the articulated transfer platform 250*a* or 250*b* is covered by the transfer belt 150, including when it is being extended outward from the device body 110 and retracted back towards the device body 110. In some implementations, the transfer device controller controls the transfer belt 150 using one or more actuators such that, when the articulated transfer platform 250*a* or 250*b* is being extended outward from the device body 110 or retracted back towards the device body 110, a top surface of the transfer belt 150 is not moving and excess slack in the transfer belt 150 is avoided or mitigated.

The examples described herein generally focus on the transfer device 100 having a transfer device controller, which is configured to control the articulated transfer platform, and optionally provides additional functionality as described herein. However, in another embodiment, the transfer device 100 can be implemented without any transfer device controller. For instance, the transfer device 100 could be entirely analogue and designed to function without a device controller.

In some implementations, the transfer device 100 has a base 120 that includes wheels 125 for assisting in translating transfer device 100 across a floor surface. Some or all of the wheels 125 can be driven by a motor, such that the transfer device 100 is able to transport itself across the floor surface. However, it will be appreciated that the wheels 125 are optional. In other implementations, the transfer device 100 is not configured for easy mobility across a floor service. For example, with reference to FIG. 4, the transfer device 100 can have a fixed base 120 with no wheels 125. Such implementations may be advantageous if the transfer device 100 is not intended to be moved during normal operation. For example, the transfer device 100 may be in a fixed position adjacent a bed of a CT or MRI machine.

Transferring a Human Body

Example operation of the transfer device 100 in transferring a human body from a first surface to a second surface will now be described with reference to FIGS. 37A-H. The operation will be described in connection with the transfer device 100 transferring a human body 10 from a gurney 20 to a bed 30 (e.g. a bed associated with a medical imaging device, such as CT or MRI scanner). However, it is to be understood that the transfer device 100 may be used to transfer a human body (or other object) off of and on to any raised surface in substantially the same manner.

Figure 37A:
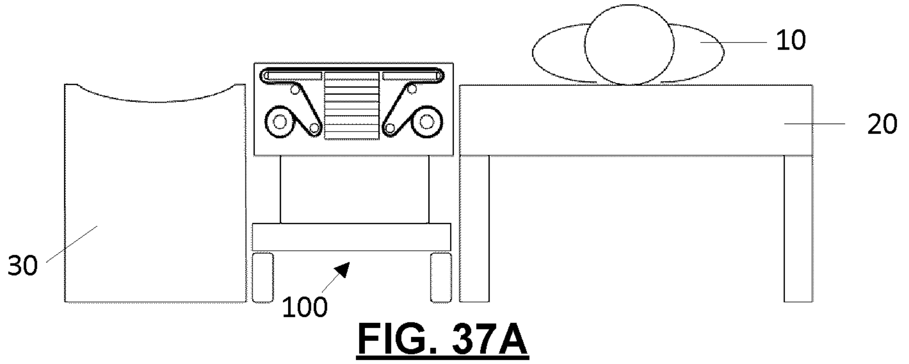
FIGS. 37A-H are a series of schematic elevation views illustrating the extendible transfer platform of FIG. 1 being used to transfer a human from a gurney onto a bed of a medical imaging scanner.

The transfer device 100 is positioned between the gurney 20 with the human body to be transferred and the bed 30, e.g. in the position shown in FIG. 37A, with the leading edge of the distal platform segment at a similar elevation to the surface of the gurney 20 on which the human body 10 is supported. For example, the transfer platform 100 may be supported by a wheeled base 120 as shown in FIGS. 1 and 2.

Figure 37B:
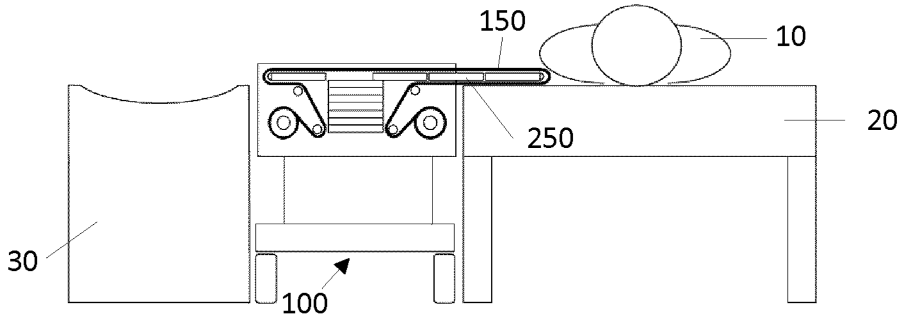
Figure 37C:
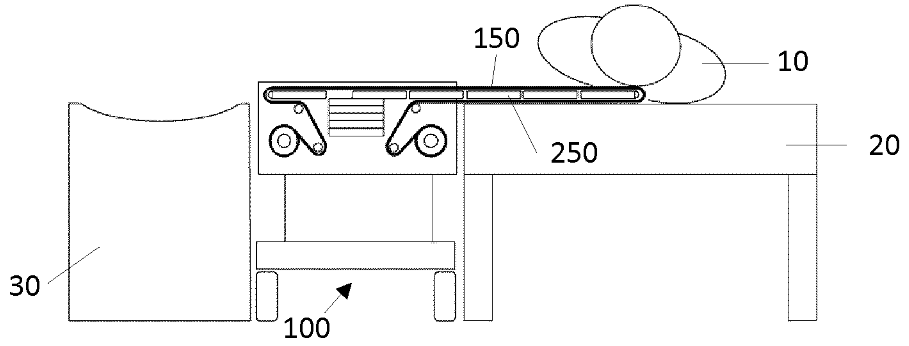
Figure 37D:
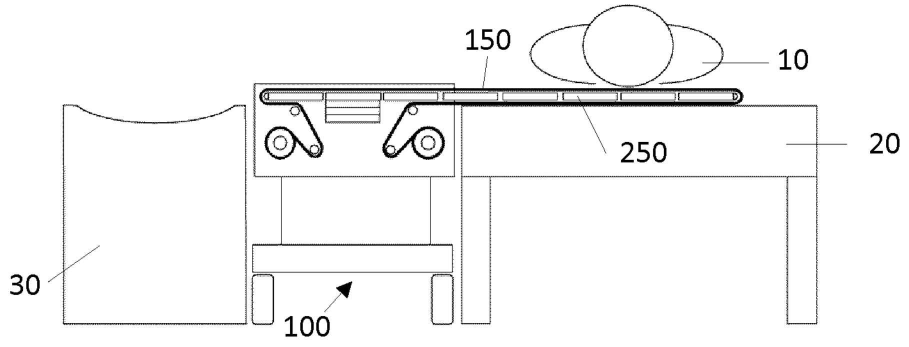

Referring to FIG. 37B, platform lateral actuators (e.g. platform drive pinions 382 as described later, not shown in FIGS. 37A-H) can be used to extend the leading edge of the articulated transfer platform (i.e. the leading edge of the distal platform segment) laterally outwardly from a side of the transfer device 100. As illustrated in FIGS. 37B to 37D, as the distal platform segment is extended, one or more intermediate platform segments 230 are sequentially engaged to form the articulated transfer platform 250. The articulated transfer platform 250 may be extended until at least a portion of the articulated transfer platform 250 is positioned below the human body 10 (and preferably completely between the surface of the gurney 20 and the human body 10), with a portion of the transfer belt 150 positioned between the transfer platform 250 and the human body 10.

In some implementations, the motion of articulated transfer platform 250 and/or the transfer belt 150 is controlled to provide limited (or zero) relative motion between an upper surface of articulated transfer platform 250 (i.e. the transfer belt 150) and the human body 10 during some or all of the transfer. In this way, the articulated transfer platform 250 can be extended outward and under the human body 10 as shown in FIGS. 37B-D without having to lift the human body 10 or roll the human body 10 onto the articulated transfer platform 250.

Optionally, a lower surface of a guard layer (e.g. guard layer 155 as described later, not shown in FIGS. 37A-H) may be in contact with the surface of the gurney 20 supporting the human body 10 before and during the transfer. Also, while not illustrated, it will be appreciated that the supporting surface 20 may be displaced and/or compressed by the articulated transfer platform 250, e.g. to reduce force on the human body 10, particularly when the articulated transfer platform 250 is being extended outward and under the human body 10 as shown in FIGS. 37B-D.

In some implementations, to enable limited relative motion between the upper surface of articulated transfer platform 250 (i.e. the transfer belt 150) and the human body 10 while the articulated transfer platform 250 is being extended outward from the transfer device 100 (i.e. FIGS. 37B-D), there is relative motion between the transfer belt 150 and the surface of the gurney 20. For instance, while the articulated transfer platform 250 is being extended outward from the transfer device 100, the transfer belt 150 is pushing outward on the surface of the gurney 20. To reduce or mitigate friction between the transfer belt 150 and the surface of the gurney 20, the surface of the gurney 20 can include a low friction bed sheet to enable the movement of the transfer belt 150. Alternatively, to reduce friction due to the relative motion, the transfer belt 150 may be made of a low friction material designed to perform such patient moving operations. Some examples of the aforementioned low friction belt material may be silicone or Polytetrafluoroethylene (PTFE) coated nylon or polyester fabrics.

Preferably, driven rollers (e.g. driven rollers 160*a* and 160*b* as described later, not shown in FIGS. 37A-H) may be controlled to take-up slack in the transfer belt 150 during the extension and/or retraction of the transfer platform 250. For example, tension in transfer belt 150 may be controlled throughout the transfer process by monitoring one or more of the following exemplary sensors: current from motor drivers, compression distance of a tensioner (e.g. tensioner 900 as described later, not shown in FIGS. 37A-H), strain sensors (not shown) embedded into the transfer belt 150, and/or other suitable sensors.

Figure 37E:
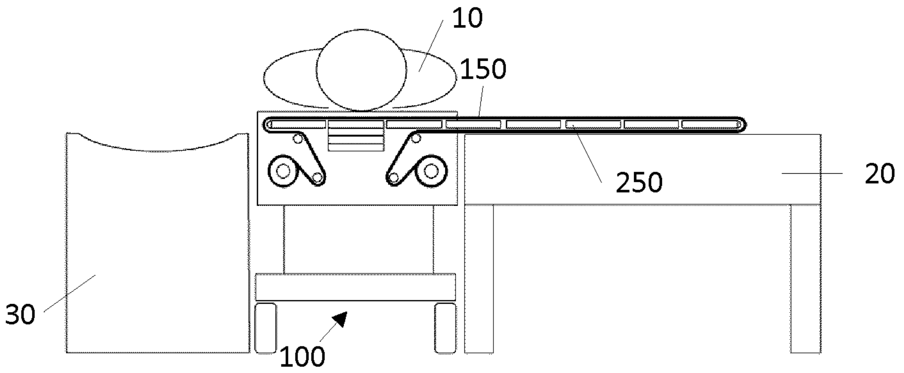

Referring to FIGS. 37D and 37E, the driven rollers are then actuated to convey the human body 10 along upper surfaces of the segments of the articulated transfer platform 250. For example, this may be achieved by 'winding' one driven roller while concurrently 'unwinding' the other driven roller to advance the upper surface of the transfer belt 150 towards the opposite side of the transfer device 100 in an actively controlled manner.

While the human body 10 is being moved from the gurney 20 towards the transfer device 100 (FIGS. 37D to 37E), if the articulated transfer platform 250 is not being retracted towards the transfer device 100, then the transfer belt 150 continues to push outward on the surface of the gurney 20. Again, to reduce or mitigate friction between the transfer belt 150 and the surface of the gurney 20, the surface of the gurney 20 can include a low friction bed sheet to enable the movement of the transfer belt 150. Again, alternatively the transfer belt 150 may be comprised of a low friction textile. Although not depicted, in another implementation, the articulated transfer platform 250 is retracted towards the transfer device 100 at the same time as the human body 10 is being moved from the gurney 20 towards the transfer device 100.

Figure 37F:
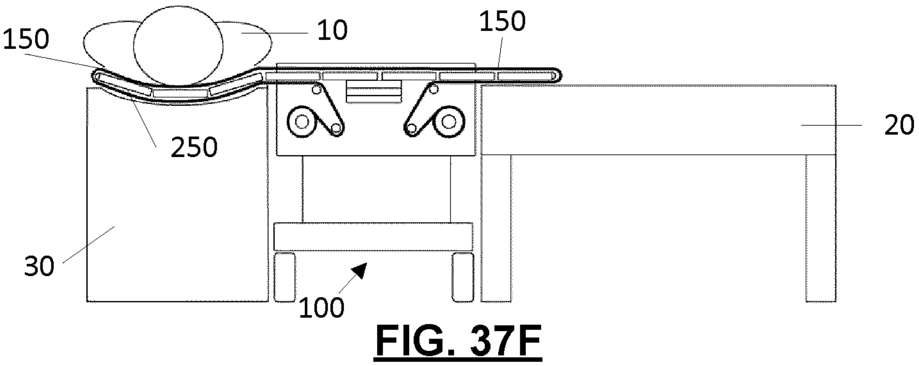

Referring to FIG. 37F, the human body 10 may then be transferred to the bed 30. For example, transfer device 100 may be controlled to laterally shift articulated transfer platform 250 to a position overlying bed 30 while controlling transfer belt 150 to maintain the human body 10 above the transfer device 100, and then transfer belt 150 may be controlled to advance patient towards the bed 30. Alternatively, the transfer device 100 may be controlled to laterally shift the articulated transfer platform 250 to a position overlying bed 30 while concurrently controlling transfer belt 150 to maintain the human body 10 above the advancing end of the transfer platform, until the human body 10 and the articulated transfer platform 250 overlie the bed 30.

Figure 37G:
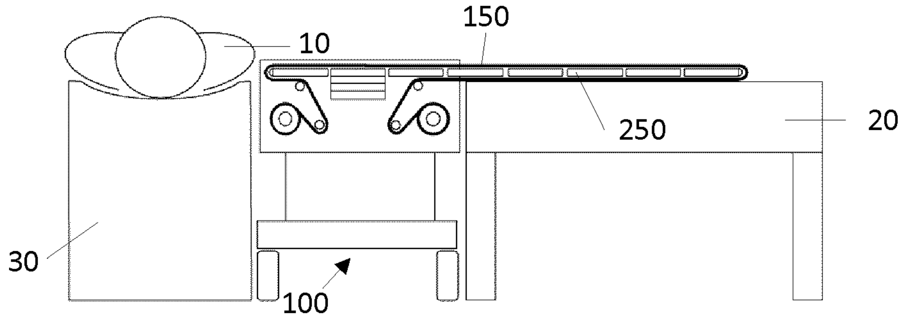
Figure 37H:
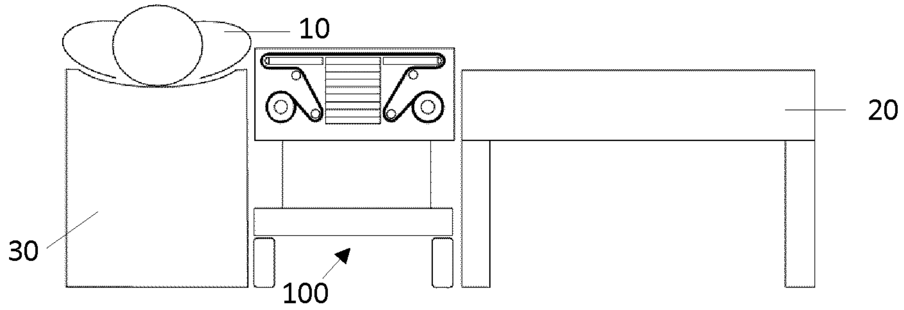

With reference to FIG. 37G, following the platform lateral actuators (e.g. platform drive pinions 382) may be used to retract the articulated transfer platform 250 from underneath the human body 10. As illustrated, the articulated transfer platform 250 may be shifted laterally while the distal platform segments and engaged intermediate platform segments are engaged to each other until clear of the patient, and then the articulated transfer platform 250 may be 'broken down' as it is retracted into a stowed position within the device body 110. Alternatively, the articulated transfer platform 250 may be 'broken down' and stowed as it is retracted from underneath the patent 10.

It will be appreciated that, in use, at least some, preferably most, and more preferably substantially all of the articulated transfer platform 250 is supported vertically by a surface onto which an object is to be transferred using the articulated transfer platform 250, or a surface from which an object to be transferred is resting. In the illustrated example, the articulated transfer platform 250 receives vertical support from the gurney 20 (FIGS. 37B-37F) and the bed 30 (FIG. 37F).

To transfer the patent 10 from the bed 30 to the gurney 20, the process illustrated in FIGS. 37A to 37H may be performed in reverse order.

In the illustrated example, the articulated transfer platform 250 is capable of extending outward in two directions. In other implementations, the segments 210, 220 and 230*a-h* include only one distal platform segment and is capable of extending outward in only one direction. For such implementations, upon moving the human body 10 onto the transfer device 100, the transfer device 100 can then be repositioned (e.g. turned around by 180 degrees) before moving the human body 10 onto the bed 30.

As noted above, there can be friction between the transfer belt 150 and the surface of the gurney 20. While low friction bed sheets can reduce or mitigate such friction, other implementations are possible in which such friction can be largely avoided, because contact between the transfer belt 150 and the surface of the gurney 20 can be mitigated or avoided completely. For example, in other implementations, the transfer device 100 has a second transfer belt (not shown) extending below a bottom surface of the articulated transfer platform 250 when the articulated transfer platform 250 is extended outward, such that the second transfer belt provides limited or zero relative motion between the bottom surface of the articulated transfer platform 250 and the surface of the gurney 20. Such an implementation is briefly described below with reference to FIGS. 74A-E.

With reference to FIGS. 74A-E, shown is another transfer device 200 transferring the human body 10 from the gurney 20 to the bed 30. The transfer device 200 of FIGS. 74A-E is similar to the transfer device 100 of FIGS. 37A-H, but includes a second transfer belt 170A in addition to the first transfer belt 150. When the articulated transfer platform 250 is being extended out the towards and under the human body 10 (FIGS. 74B-D), the second transfer belt 170A provides limited or zero relative motion between the bottom surface of the articulated transfer platform 250 and the surface of the gurney 20. Likewise, when the human body 10 is moved towards and on top of the transfer device 100 (FIG. 74E), the second transfer belt 170A provides limited or zero relative motion between the bottom surface of the articulated transfer platform 250 and the surface of the gurney 20.

Therefore, FIGS. 74A-E demonstrate the operation of the transfer device 200 where the lower guard belt 170A has been routed in such a way that extension of the platform also draws out lower guard material from within the middle of the platform to create a lower no-shear surface simultaneously along with the upper surface. The first transfer belt 150 interacts with the patient at rest and the lower guard belt 170A (or pair of lower guard belts 170A-B) interacts with the patient's support surface. Each belt is operatively terminated such that when the transfer platform extends, the belts are drawn out from the central cavity of the platform only, thereby unrolling under the patient and creating zero shear or relative velocity to the support surface or patient at rest. One or both the transfer belt 150 and lower guard belt 170A may be comprised of a low friction material in order to reduce forces on the object being transferred, relative friction between the transfer belt 150 and lower guard belt 170A, in addition to reducing reaction forces back to the transfer device 100 due to friction occurring during the act of transfer.

While the apparatus' and methods disclosed herein are described specifically in relation to and in use with transferring a human body (e.g. an individual with reduced, limited, or no mobility, an able bodied individual, an unconscious individual, an incapacitated individual, etc.), it will be appreciated that the apparatus' and methods may alternatively be used to transfer other objects, such as those that may be bulky, cumbersome, delicate, and/or difficult to grasp and move. For example, the apparatus' and methods disclosed herein may be suited and/or adapted for use to transfer livestock or domestic animals, undomesticated animals (e.g. in a zoo or wildlife care facility), human corpses (e.g. in a funeral home of a mortuary), inanimate objects (e.g. in courier, cargo, and/or logistical operations), and the like.

Example Implementation Details

Example implementation details of the transfer device 100 are provided in this section with reference to the drawings. As noted above, it is to be understood at the outset that the transfer device 100 is shown with very specific features for exemplary purposes only. Other implementations are possible and are within the scope of the disclosure.

Figure 6:
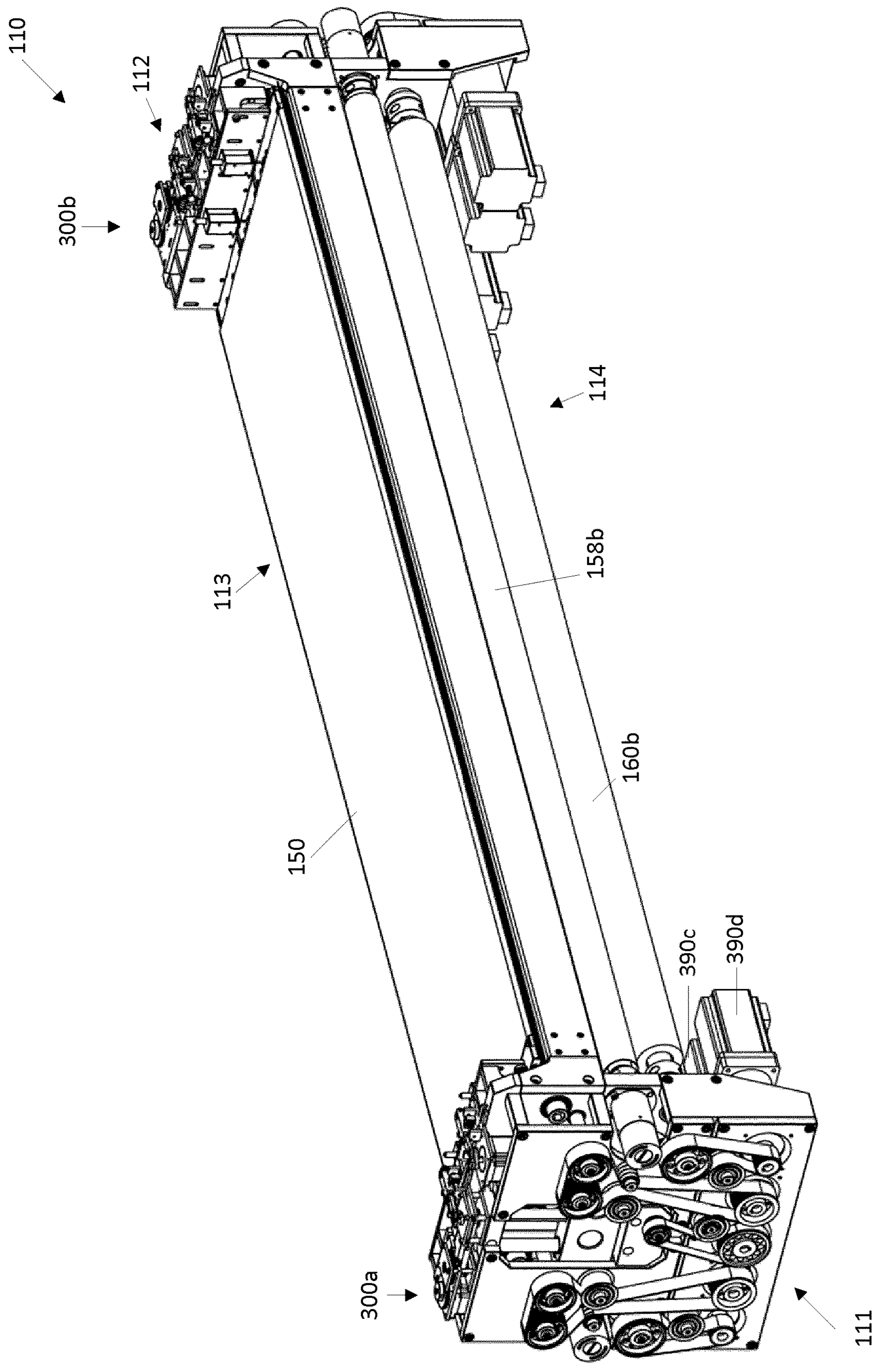
FIG. 6 is a perspective view of the transfer device of FIG. 5, with a support base omitted for clarity.

With reference to FIG. 6, the transfer device 100 includes a first end drive assembly 300*a* and a second end drive assembly 300*b*. The end drive assemblies are connected to each other by lateral support members, such that the end drive assemblies are on opposite ends of the transfer device 100.

With reference to FIGS. 10, details of the second end drive assembly 300*b* can be seen. In some implementations, the transfer belt 150 has a fixed length, and a first end of the transfer belt 150 is secured to a first driven roller 160*a*, and a second end of the transfer belt 150 is secured to a second driven roller 160*b*. Accordingly, the transfer belt 150 may be characterized as a discontinuous belt 150.

Utilizing a discontinuous transfer belt 150 may have one or more advantages. For example, this may facilitate the removal and/or replacement of the transfer belt 150 (e.g. by removing a driven roller with the transfer belt attached). This may result in the transfer device 100 being relatively easy to clean and/or maintain, which may result in reduced downtime. This may be of particular importance in use cases where cross-contamination is of concern (e.g. in hospitals, care homes, etc.).

Additionally, or alternatively, using a discontinuous belt with driven rollers on both ends may also have a mechanical advantage, in that the transfer belt's tension can be controlled from both ends of the belt. For example, this may assist in providing a desired tension level, and/or a desired level of 'slack' (or a lack thereof) in transfer belt 150.

As shown schematically in FIG. 10, the transfer belt 150 extends from the first driven roller 160*a* and passes around a tensioner 165*a*. From there, the transfer belt 150 extends around a roller 440*a*, the leading edge 213 of the first distal platform segment 210, along the upper surface 216 of first distal platform segment 210, the upper surface 236 of one or more intermediate platform segments 230, and the upper surface 226 of second distal platform segment 220, and around the leading edge 224 of second distal platform segment 220. Transfer belt 150 then passes around a roller 440*d*, a tensioner 165*b*, and terminates at the second driven roller 160*b*.

In the illustrated example, the transfer belt 150 is guided around two passive (i.e. non-driven) rollers 165*a* and 165*b* to maintain tension and to avoid potentially interfering interactions with other components located within the housing (e.g. control systems, motors and motor drivers, gears, and the like). It will be appreciated that fewer, more, or no tensioners 165 may be provided in alternative embodiments.

Figure 12:
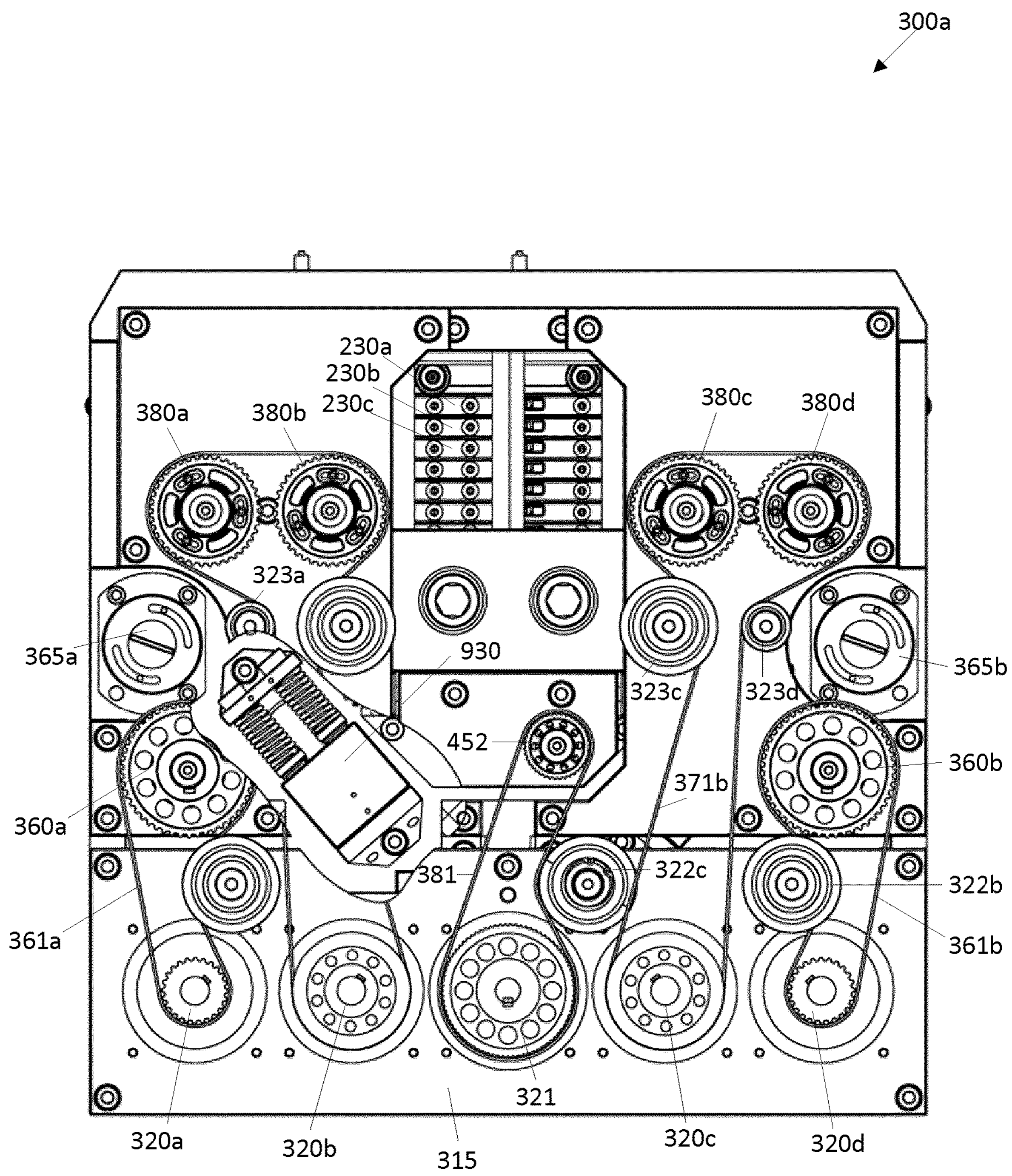
FIG. 12 is an end plan view of the transfer device of FIG. 7, with portions of the support plates removed to show a transfer belt tensioner assembly.
Figure 14:
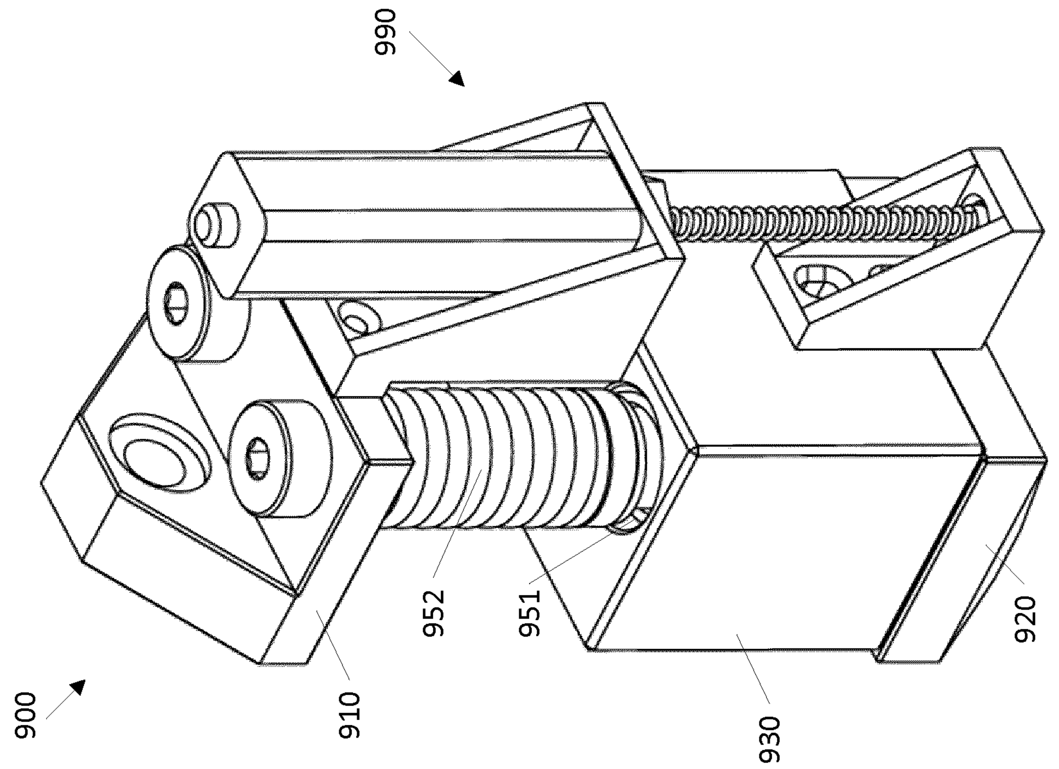
FIG. 14 is a second perspective view of the belt tensioner assembly of FIG. 13, shown with an example linear displacement sensor.
Figure 13:
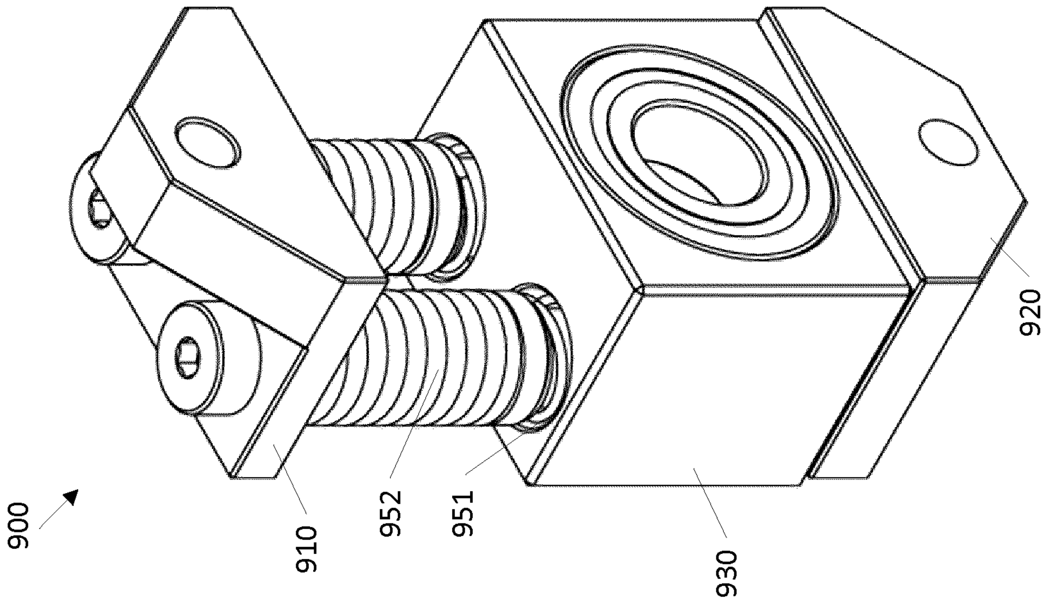
FIG. 13 is a first perspective view of a belt tensioner assembly in accordance with one embodiment.

An example belt tensioner assembly will now be described with reference to FIGS. 12 to 15C. As illustrated in FIG. 12, a belt tensioner assembly 900 may be positioned between structural plates of an end drive assembly 300*a-b* (discussed further below). With reference to FIG. 13, the belt tensioner assembly 900 includes a first frame member 910 secured in fixed relation to a second frame member 920 by shafts 940*a* and 940*b*. A movable frame member 930 can translate along shafts 940*a* and 940*b*. As illustrated in FIG. 14, a linear displacement sensor 990 is attached to provide an output signal based on the relative position of the movable frame member 930.

Figure 15C:
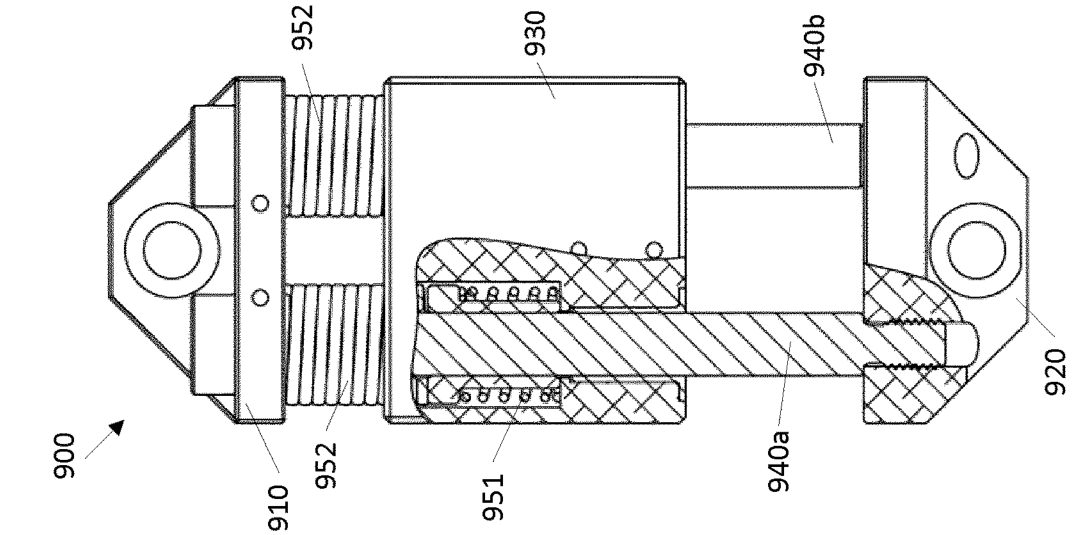
FIG. 15C is a partial section view of the belt tensioner assembly of FIG. 13, with the movable frame member in a compressed position.
Figure 15B:
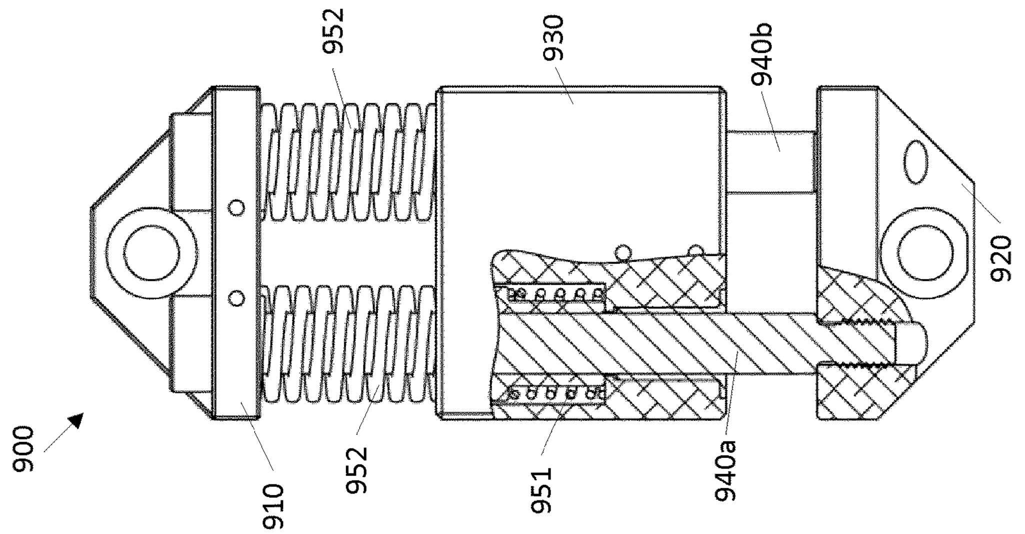
FIG. 15B is a partial section view of the belt tensioner assembly of FIG. 13, with the movable frame member in a partially compressed position.
Figure 15A:
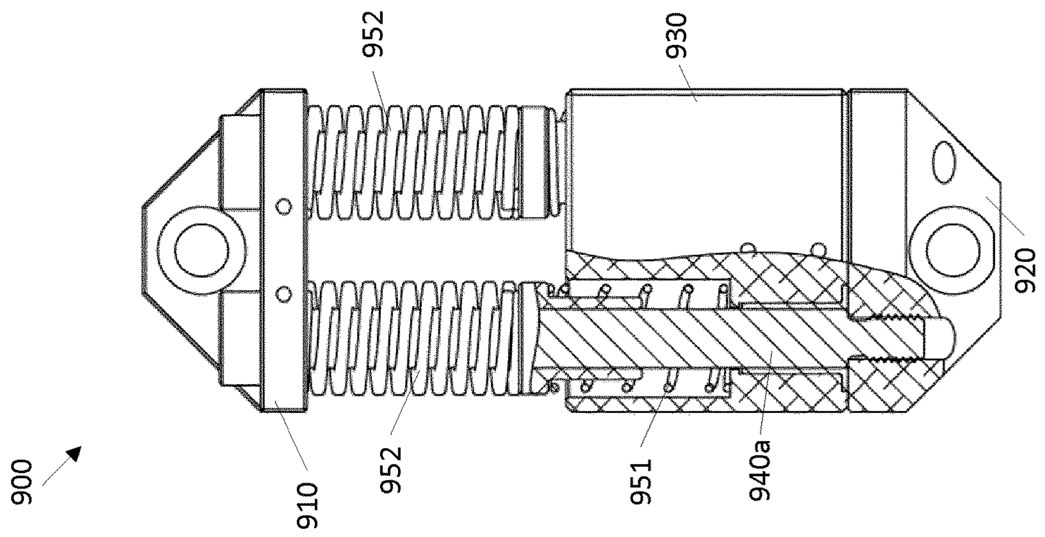
FIG. 15A is a partial section view of the belt tensioner assembly of FIG. 13, a the movable frame member in an extended position.
Figure 16:
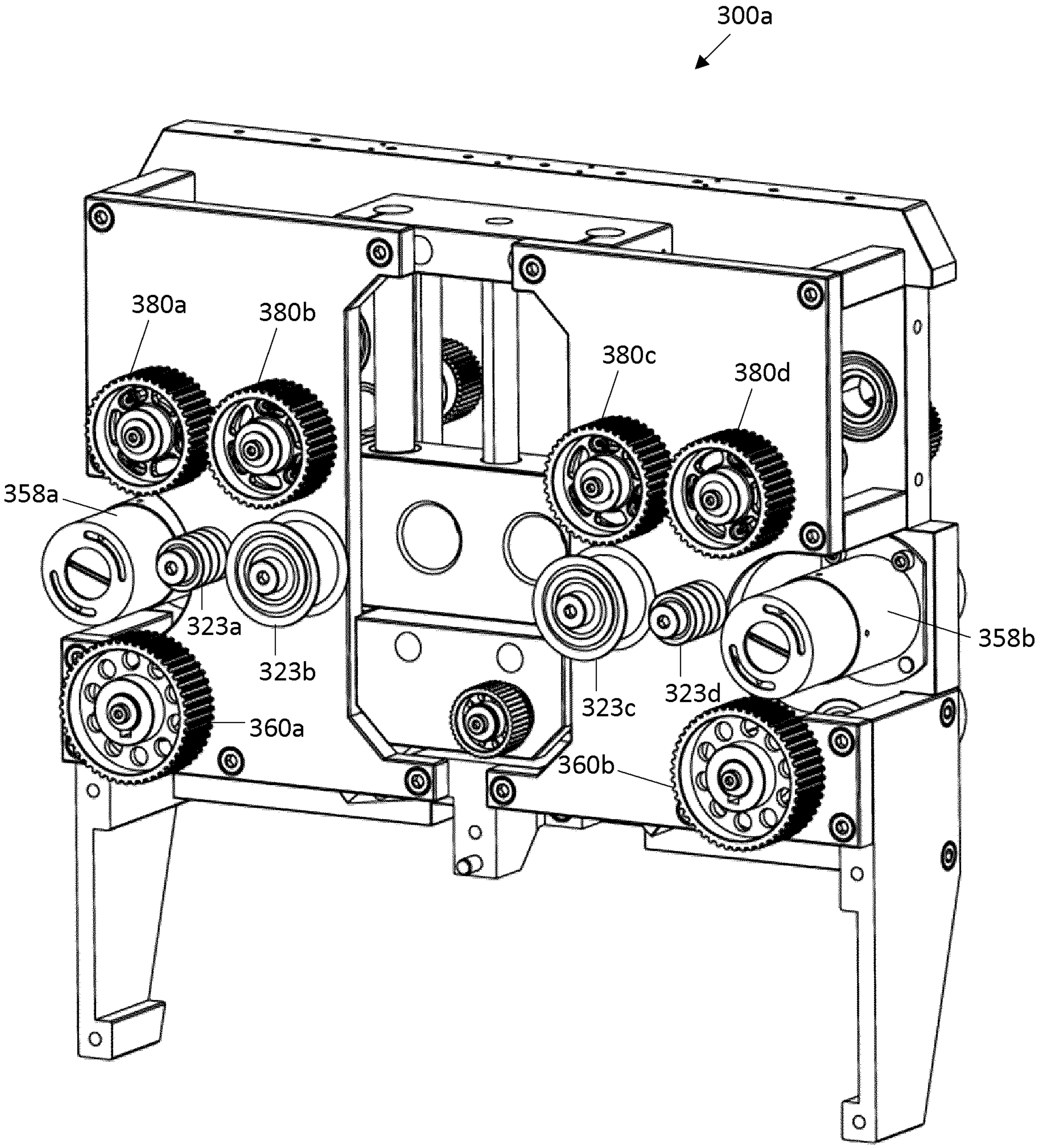
FIG. 16 is a perspective view of an outer side of an end drive assembly of the transfer device of FIG. 7, with a motor assembly and drive belts omitted for clarity.

Turning to FIGS. 15A to 15C, in the illustrated example, the movable frame member 930 is biased towards second frame member 920. In the illustrated example, this bias is applied by first springs 951 and second springs 952 arranged in series, where the first and second springs have different stiffnesses or spring rates. As a result, during a first travel range of the movable frame member 930 (e.g. between the positions shown in FIGS. 15A and 15B), only springs with a lower relative spring rate (e.g. spring 951 in this example) will be deformed, while during a second travel range of the movable frame member 930 (e.g. between the positions shown in FIGS. 15B and 15C), both springs will be deformed, including springs with a higher relative spring rate (e.g. spring 952 in this example).

An advantage of this design is that it may allow the linear displacement sensor 990 to provide a high resolution signal both at relatively low transfer belt tensions (e.g. when no objects are in contact with transfer belt 150 and/or articulated transfer platform 250), and at relatively high transfer belt tensions (e.g. when a patient is being transferred on the articulated transfer platform 250).

In the illustrated example, each tensioner 165*a* and 165*b* is passively sprung. Alternatively, each tensioner 165*a* and 165*b* may be actively actuated, e.g. by providing a linear actuator instead of, or in addition to, one or more passive springs. Additionally, or alternatively, each tensioner 165*a* and 165*b* may be actively dampened, e.g. using ferro-dampening fluids or the like. In some embodiments, the relative position of each tensioner 165*a* and 165*b* may be determined by a positioning sensor (not shown) such as a Time of Flight (TOF) or linear potentiometer, for example. This determined tensioner position may be used e.g. by the transfer device controller to measure and/or infer tension within the transfer belt 150.

As shown in FIGS. 5 and 6, each driven roller 160*a*, 160*b* is driven using a corresponding motor 310. It will be appreciated that any suitable motor type (e.g. stepper motors, DC or AC motors, brushless DC (BLDC) motors, pneumatic rotary motors, direct electrical motors, and the like) may be used in one or more variant embodiments. Additionally, or alternatively, other gearing (e.g. two or more stages, planetary gearing) may be used. During operation, it will be appreciated that corresponding motors or actuators may be driven independently or synchronously to suit the required function(s).

As discussed above, the transfer belt 150 passes around the leading edge 213 of first distal platform segment 210 and around the leading edge 224 of second distal platform segment 220. Optionally, some or all of leading edges 213 and 224 may be provided with one or more friction-reducing features. With reference to FIG. 7, in the illustrated example a number of rollers 255 are positioned along the leading edge 224 of second distal platform segment 220. Alternatively, or additionally, some or all surfaces proximate the leading edges 213 and 224 may be made from a low-friction material (e.g. Polytetrafluoroethylene (PTFE), Polyamides, Graphite, Acetol, Ultra High Molecular Weight Polyethylene (UHMW PE),) and/or have a low-friction coating applied thereto. Alternatively, or additionally, friction may be reduced via a controlled application of compressed air, one or more lubricants, captive ball bearings, or other suitable systems.

In some implementations, with reference to FIG. 10, flexible guard layers 155*a* and 155*b* are provided below the transfer belt 150 to inhibit or prevent direct contact between the transfer belt 150 and the surface on which the object being transferred to or from using the articulated transfer platform 250. For example, as illustrated in FIG. 10, a first guard layer 155*a* may be formed from a textile and/or flexible material with a first end 156*a* secured to the ends 221 and 222 of the second distal platform segment 220, and a second end 157*a* secured to a take-up roller 158*a*, which may be spring-biased and/or actively driven to take up the first guard layer 155*a* as the articulated transfer platform 250*b* moves towards a retracted position. In the illustrated example, the first guard layer 155*a* passes over guide member 159*a*, which is secured to the end drive assembly 300*a*, such that guard layer 155*a* remains proximate the underside of the articulated transfer platform 250*a* when the articulated transfer platform 250*a* is in an extended position. A second guard layer 155*b* has a first end 156*b* secured to the ends 211 and 212 of the first distal platform segment 210, and a second end 157*b* secured to a take-up roller 158*b*, which may be substantially similar to the take-up roller 158*a*. Optionally, the flexible guard layers 155*a* and 155*b* may be formed from a low-friction material, e.g. Polytetrafluoroethylene (PTFE), Polyamides, Graphite, Acetol, Ultra High Molecular Weight Polyethylene (UHMW PE), and the like.

Figure 75:
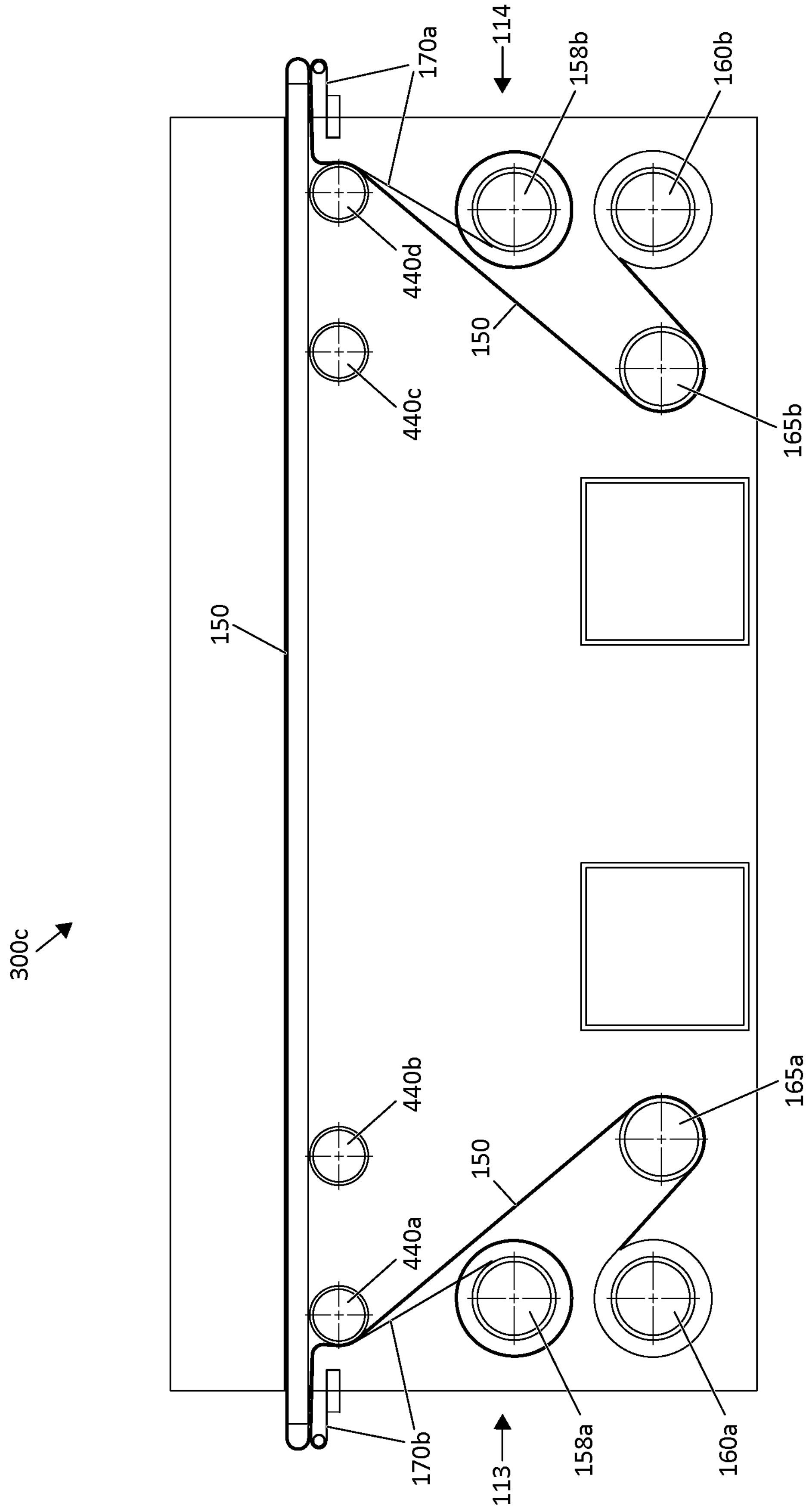
FIG. 75 is a schematic view of a transfer belt path of the transfer device of FIGS. 74A-E.

With reference to FIG. 75, shown is a schematic view of a transfer belt path of the transfer device of FIGS. 74A-E. An end drive assembly 300*c* has a belt path for the first transfer belt 150 that is similar to what is shown in FIG. 10. Much like in FIG. 10, the transfer belt 150 extends from the first roller 160*a* around idlers 165*a* and 166*a*, around a top surface of the transfer platform, around idlers 165*b* and 166*b*, and onto a second roller 160*b*. However, note that the first transfer belt 150 is not routed between the shafts 440*a* and 440*b* and the platform segments 210, 220 and 230*a-h*. Also note that there is a second transfer belt 170A and a third transfer belt 170B. The second transfer belt 170A extends from roller 158*b*, and the third transfer belt 170B extends from roller 158*a*. In some implementations, the second transfer belt 170B and the third transfer belt 170C are both passive (e.g. spring loaded, using multi-rotation torsion springs) and are not connected to any actuator or device controller. In other implementations, the second transfer belt 170B and the third transfer belt 170C are coupled to actuators that are operably coupled to the transfer device controller.

Figure 11:
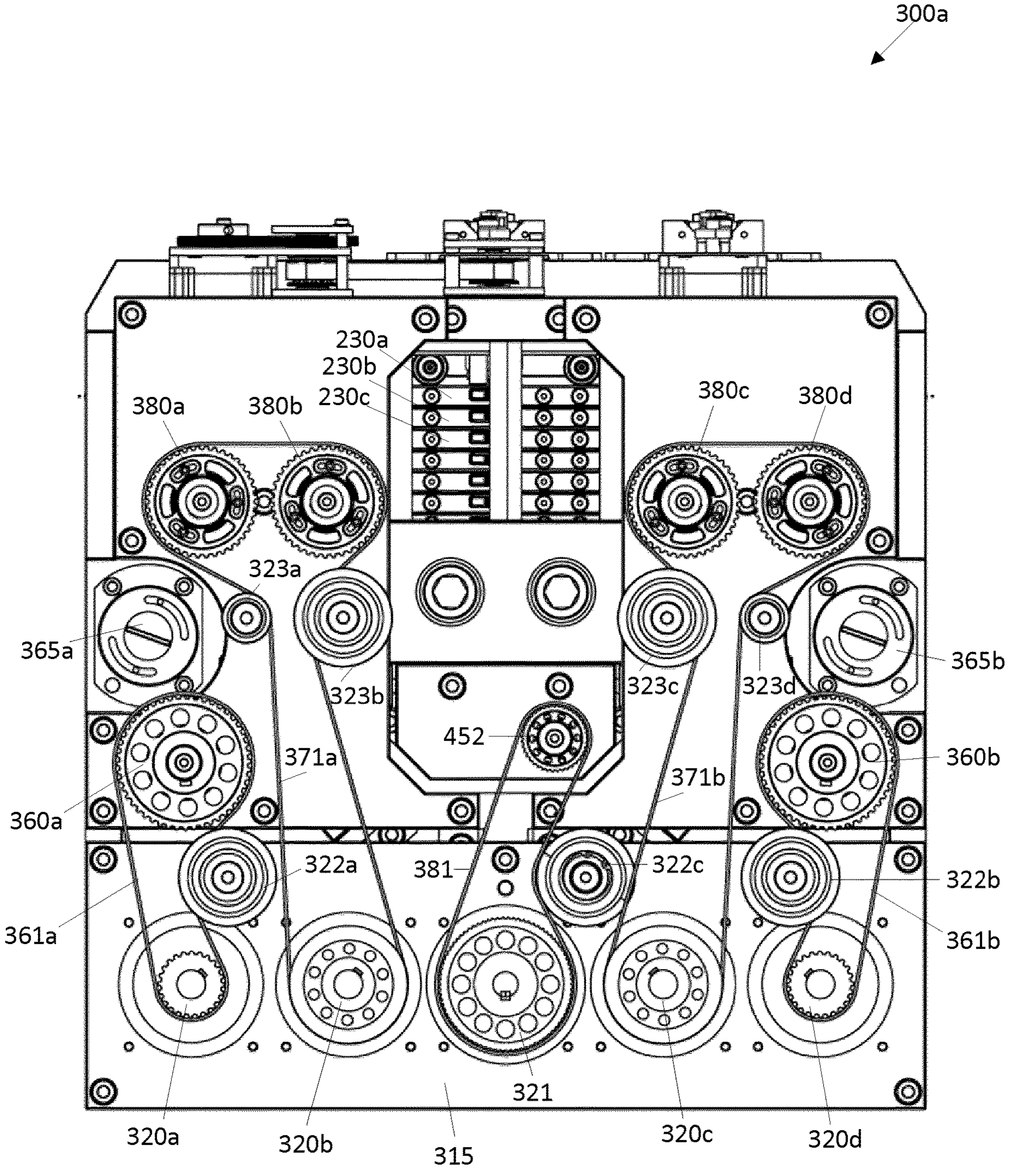
FIG. 11 is an end plan view of the transfer device of FIG. 7.

FIG. 11 illustrates an example implementation of the first end drive assembly 300*a*. As noted above, the end drive assemblies 300*a* and 300*b* are provided at the ends 101 and 102 of the transfer device 100. The end drive assemblies 300*a* and 300*b* are substantially mirror images of each other, and are preferably operated in concert with each other to control opposite ends of the articulated transfer platform 250, the transfer belt 150, optional guard layer(s) 155*a* and 155*b*, etc. substantially simultaneously.

In the illustrated example, the end drive assembly 300*a*, first and second belt drive sprockets 320*a* and 320*d* are driven by motors 390*a* and 390*d*, respectively. The belt drive sprockets 320*a* and 320*d* are connected to transfer belt roller sprockets 360*a* and 360*b* by drive belts 361*a* and 361 *b*, respectively. Rotation of the transfer belt roller sprockets 360*a* and 360*b* results in rotation of the transfer belt rollers 165*a* and 165*b*, respectively. In the illustrated example, tension idlers 322*a* and 322*b* are also provided to control the tension of drive belts 361*a* and 361 *b*, respectively. It will be appreciated that the tension idlers 322*a* and 322*b* are optional.

Also shown are platform drive sprockets 320*b* and 320*c*, which are driven by motors 390*b* and 390*c*, respectively. The platform drive sprocket 320*b* is connected via a drive belt 371*a* to a first series of segment drive sprockets 380*a* and 380*b*. The platform drive sprocket 320*c* is connected via a drive belt 371*b* to a second series of segment drive sprockets 380*c* and 380*d*. Idlers 323*a* and 323*b* are provided in order to control tension on the drive belt 371*a*, and idlers 323*c* and 323*d* are provided in order to control tension on the drive belt 371*b*.

Figure 17:
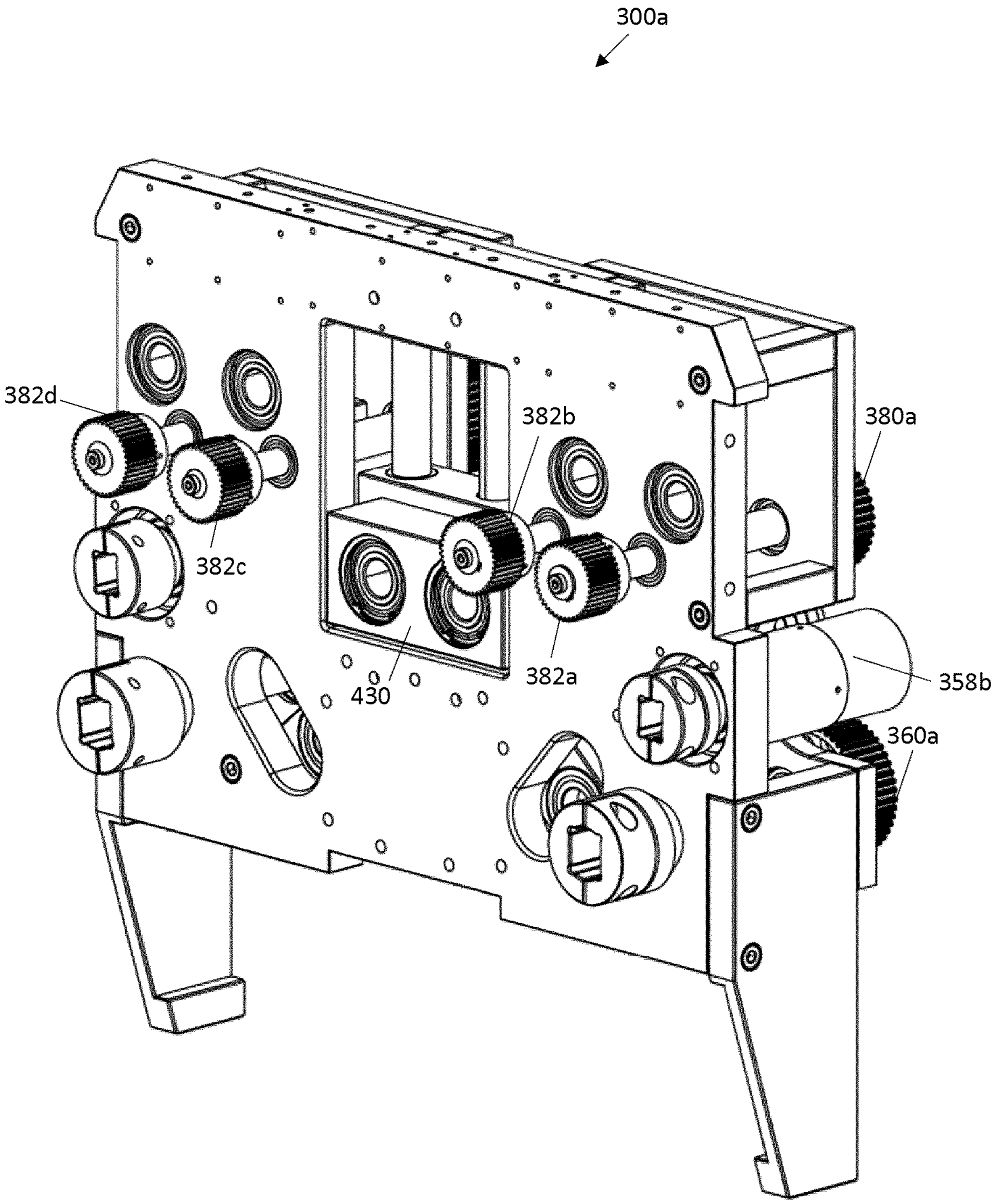
FIG. 17 is a perspective view of an inner side of the end drive assembly of FIG. 16.

FIG. 17 illustrates an inner side of the end drive assembly 300*a*. In the illustrated example, platform drive pinions 382*a*, 382*b*, 382*c* and 382*d* are provided at an upper end of the platform. These drive pinions 382*a*, 382*b*, 382*c* and 382*d* are connected to segment drive sprockets 380*a*, 380*b*, 380*c* and 380*d*, respectively (see e.g. FIG. 11).

In the illustrated example, teeth of platform drive pinions 382*a*, 382*b*, 382*c* and 382*d* engage platform rack segments (not shown) provided on the undersides of the ends 211, 212, 221 and 222 of the distal platform segments 210 and 220, and on the undersides of the ends 231 and 232 of the intermediate platform segments 230*a-h*. It will be appreciated that in one or more alternative embodiments, the engagement between the end drive assembly 300*a* and the platform segments 210, 220 and 230*a-h* may not include a rack and pinion arrangement. For example, platform drive rollers may have a compressible elastomer configured to provide a sufficiently high frictional coefficient between themselves and the undersides of the ends of the platform segments 210, 220 and 230*a-h*.

Figure 18:
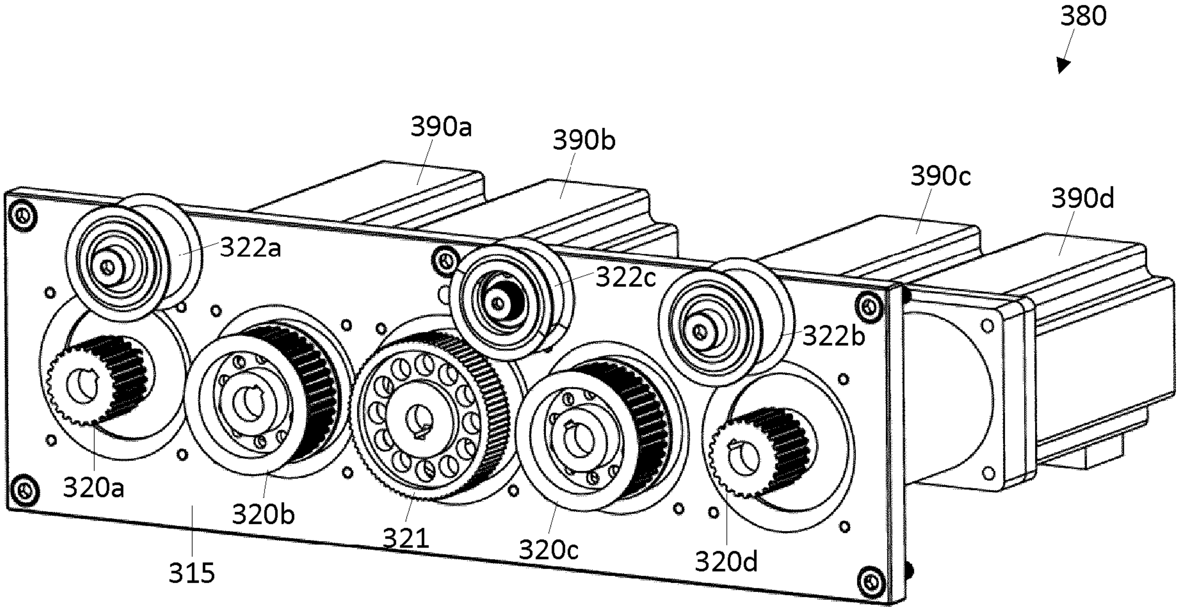
FIG. 18 is a perspective view of a motor assembly for the end drive assembly of FIG. 11.
Figure 19:
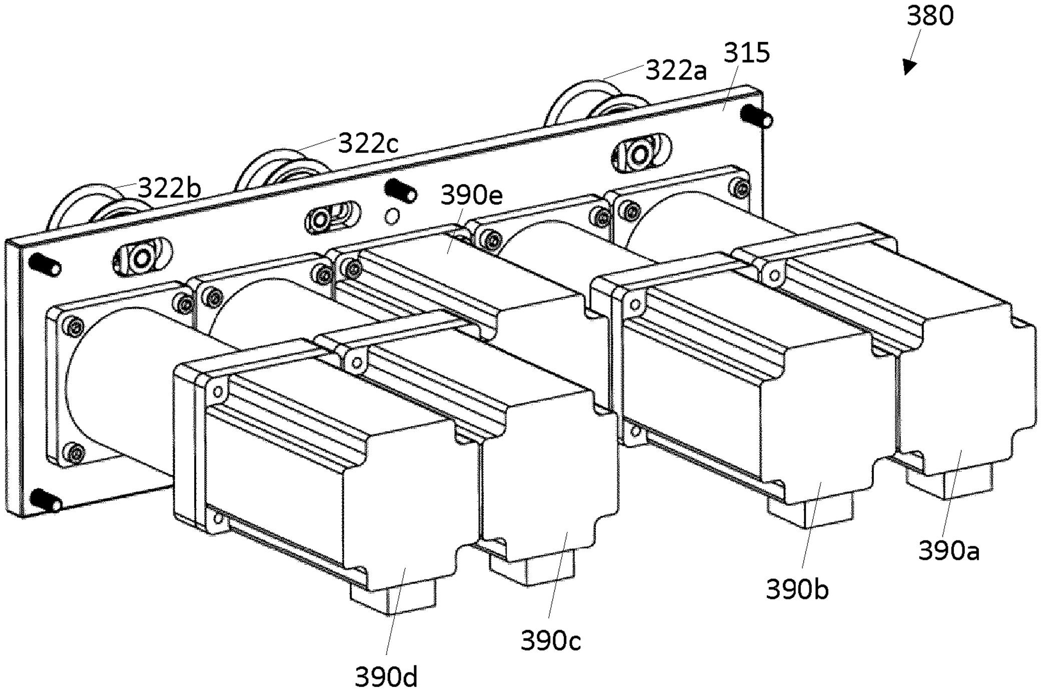
FIG. 19 is another perspective view of the motor assembly of FIG. 18.

FIGS. 18 and 19 illustrate an example of a motor hub assembly 380. In the illustrated example, a motor baseplate 315 supports motors 390*a-e*. Two of the motors 390*a* and 390*e* are connected to the belt drive sprockets 320*a* and 320*d* and via one or more linear driveshafts, and two of the motors 390*b* and 390*d* are connected to the platform drive sprockets 320*b* and 320*c* in a similar manner. Also, the tension idlers 322*a* and 322*b* are illustrated as being mounted on the motor base plate 315.

Enabling the motor hub assembly 380 to be modular may have one or more advantages. For example, allowing an entire set of motors and drive wheels to be ‘swapped out’ may facilitate easier maintenance and/or service of the transfer device 100, which may lead to reduced downtime of the transfer device 100.

Figure 21:
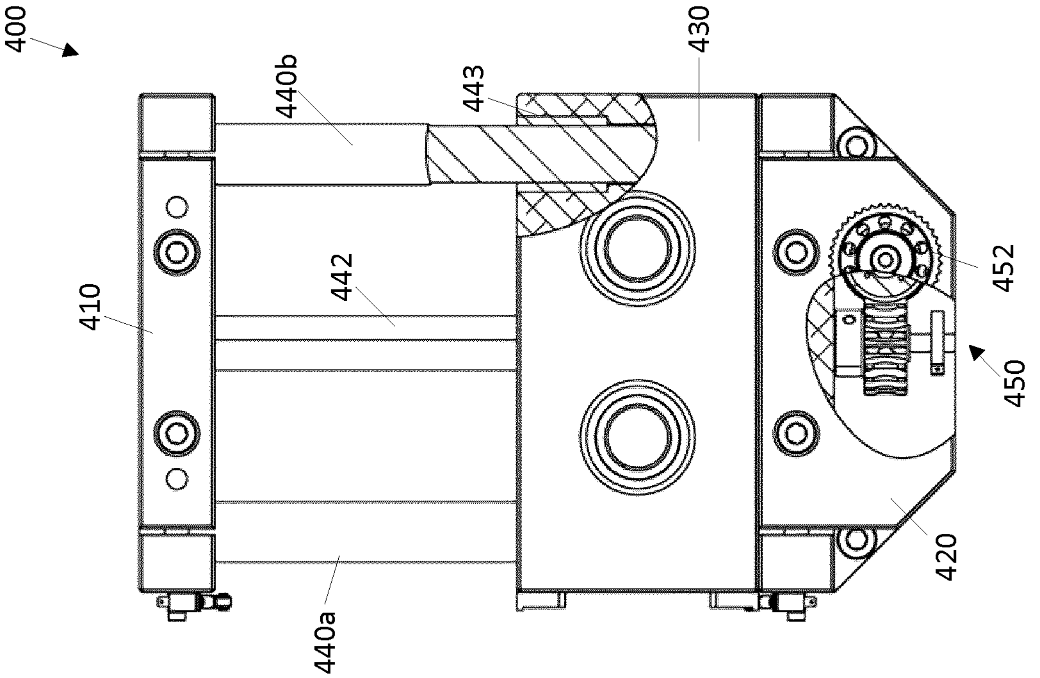
FIG. 21 is an end plan view of the intermediate platform segment support assembly of FIG. 20, with portions shown in partial section for clarity.
Figure 20:
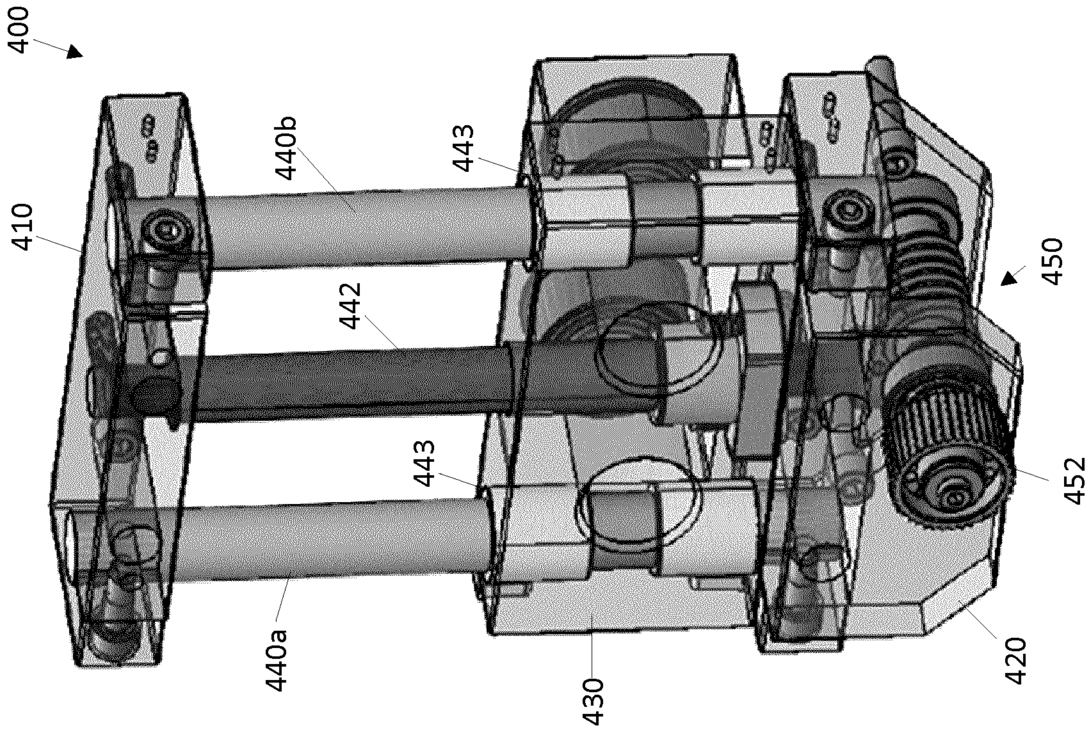
FIG. 20 is a perspective view of an intermediate platform segment support assembly for the end drive assembly of FIG. 16, with some components shown as translucent for clarity.

FIGS. 20 and 21 illustrate an example of an intermediate platform segment support assembly 400. As will be discussed further below, the intermediate platform segment support assembly 400 is configured to selectively raise and lower the intermediate platform segments 230*b-h* in order to bring the engagement mechanisms of adjacent intermediate platform segments 230*b-h* into alignment with one another.

Figure 34:
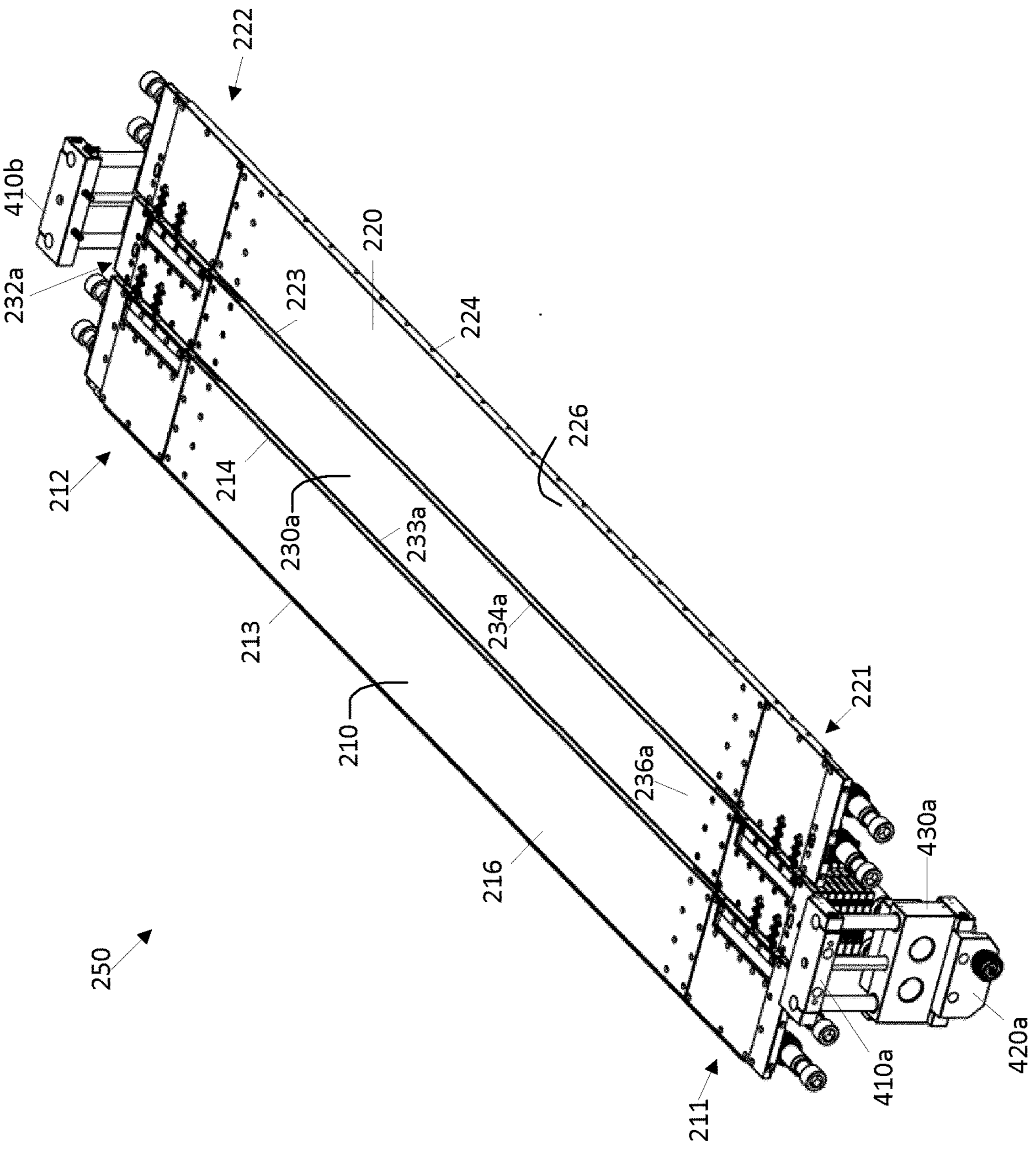
FIG. 34 is a perspective view of the platform segments, intermediate platform segment supports, and platform drive pinions of the transfer device of FIG. 1, with the platform segments in a stowed position.
Figure 36:
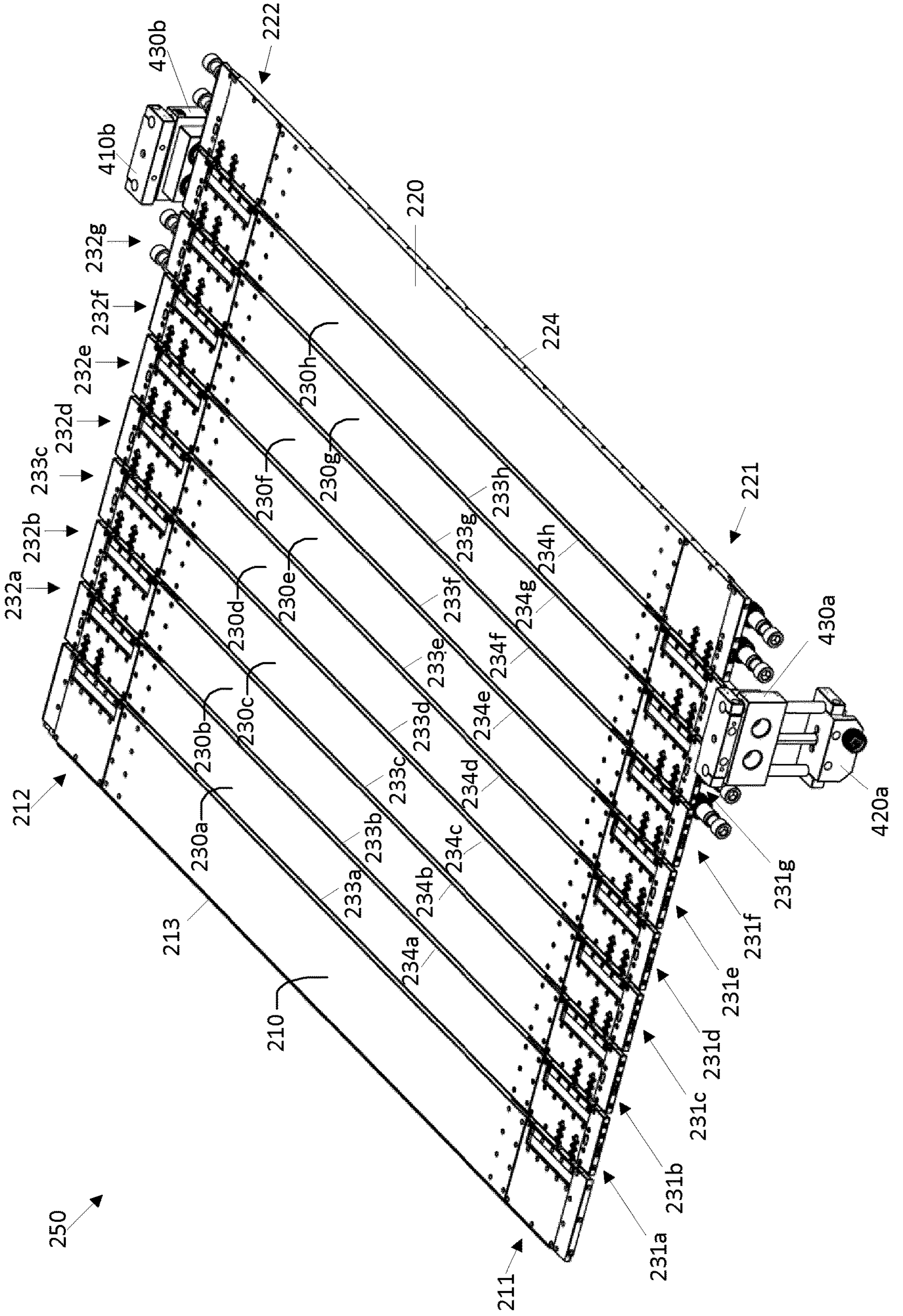
FIG. 36 is a perspective view of the platform segments, intermediate platform segment supports, and platform drive pinions of FIG. 34, with the platform segments in a fully extended position.

In the illustrated example, the intermediate platform segment support assembly 400 includes an upper frame member 410 and a lower frame member 420. The frame members 410 and 420 are connected in fixed relation to each other via shafts 440*a* and 440*b*. A translating frame member 430 may be moved vertically along the shafts 440*a* and 440*b* between a lowered position proximate the lower frame member 420 (e.g. as shown in FIGS. 20, 21, and 34) and a raised position proximate the upper frame member (e.g. as shown in FIG. 36). In the illustrated example, optional sleeve bushings 445 facilitate movement of the translating frame member 430 along shafts 440*a* and 440*b*.

In the illustrated example, a reduction worm gear assembly 450 is provided to drive the central shaft 442. Such a configuration may allow for precise control of the speed and/or position of the translating frame member 430. Another advantage of this design is that, when not driven, positional slippage or drift of the translating frame member 430 may be reduced or eliminated.

Returning to FIG. 11, in the illustrated example, an actuator sprocket 452 is connected to a drive sprocket 321 by a drive belt 381. Rotation of the drive sprocket 321 results in vertical translation of the translating frame member 430, thereby resulting in vertical translation of any of the intermediate platform segments 230*b-h* supported by the translating frame member 430. In the illustrated example, the drive sprocket 321 is driven directly by the motor 390*e*.

In the illustrated example, a tension idler 322*c* is also provided to control the tension of the drive belt 381. It will be appreciated that the tension idler 322*c* is optional.

In the illustrated example, actuation of the intermediate platform segment support assembly 400 is mechanically separate from the lateral actuation of the transfer platform 250. For example, the drive sprocket 321 and the motor 390*e* are not mechanically integrated with the belt drive sprockets 320*a* and 320*d*, the platform drive sprockets 320*b* and 320*c*, or with any of the motors 390*a-d*. In one or more alternative embodiments, a mechanical linkage system, gearing system, or the like may be provided to mechanically synchronize the operation of the platform segment support assembly 400 with the articulated transfer platform drive systems and/or the transfer belt drive systems.

In the examples illustrated in FIGS. 1 to 36, the articulated transfer platform 250 is provided as a series of the platform segments 210, 220 and 230*a-h* whose edges can be secured to and/or released from each other ‘on the fly’ in order to extend or retract the articulated transfer platform 250 to one side or the other side of the transfer device 100. The selective connection/disconnection (which may be characterized as engagement/disengagement) of adjacent platform segments 210, 220 and 230*a-h* will be discussed with reference to FIGS. 22 to 36.

Figure 22:
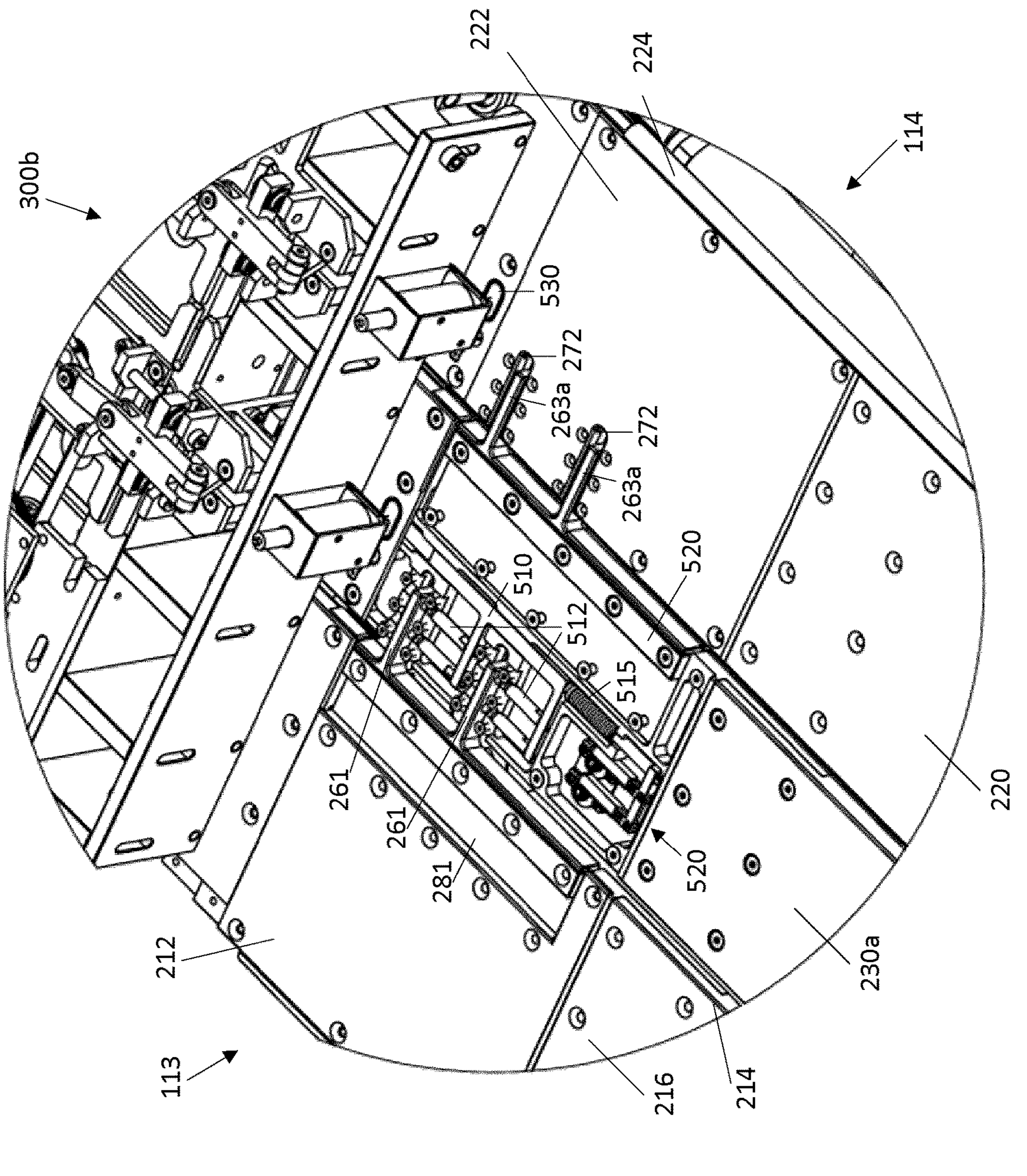
FIG. 22 is a top perspective view of an end of an intermediate platform segment positioned between the ends of distal platform segments, with a cover plate for an engagement mechanism removed for clarity.

FIG. 22 illustrates ends of the platform segments 210, 220 and 230*a* adjacent to the end drive assembly 300*b*. In the illustrated example, the first and second distal platform segments 210 and 220 are in a retracted position proximate the sides 113 and 114 of the device body 110. Positioned between them is the lead intermediate platform segment 230*a*.

Figure 23:
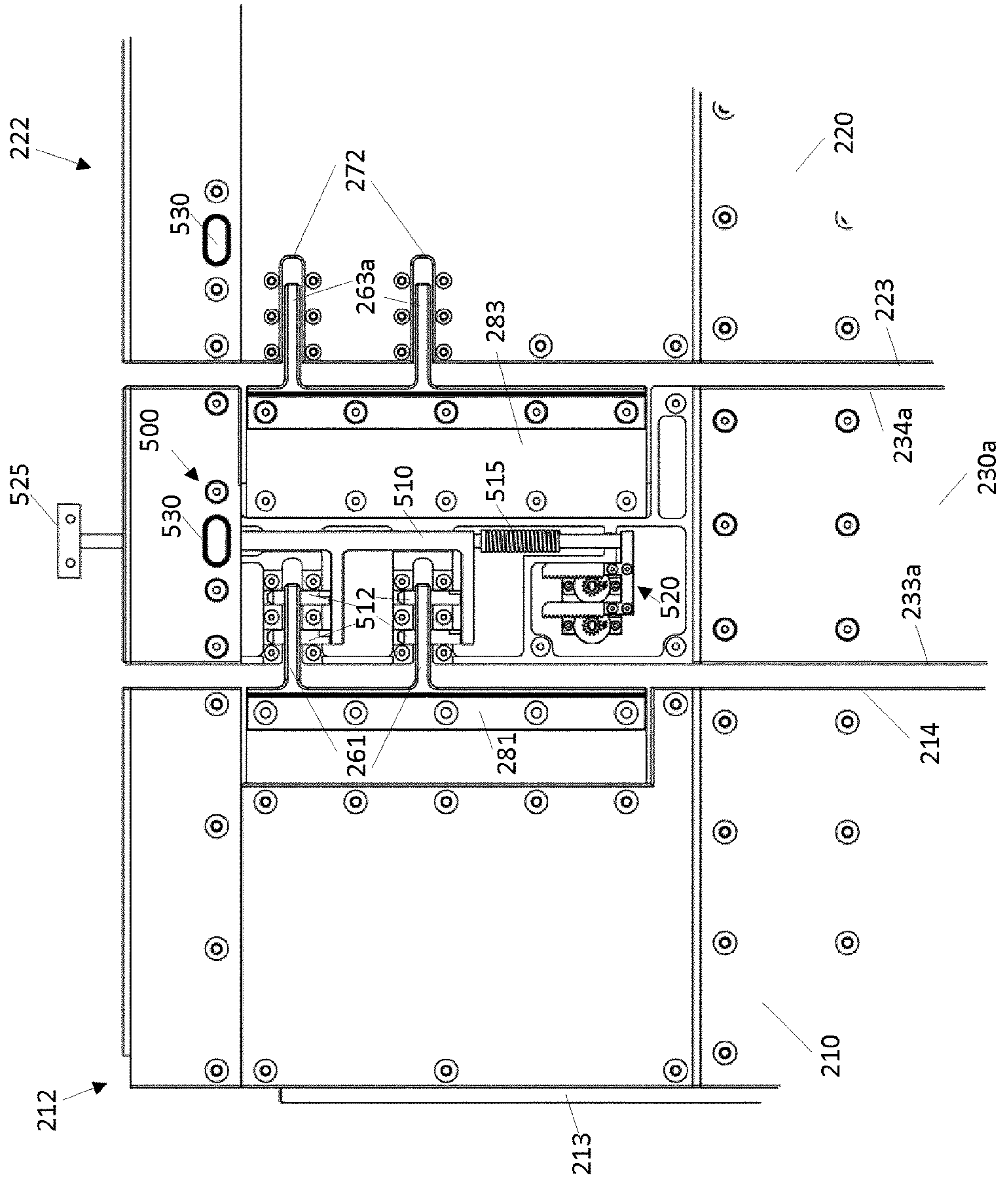
FIG. 23 is a top plan view of an engagement mechanism of an intermediate platform segment, with portions shown in section for clarity.

With reference to FIG. 23, the first distal platform segment 210 has a series of projections 261 that extend inwardly from trailing edge 214. These projections 261 are configured to engage recesses 273*a* of intermediate platform segment 230*a*. The second distal platform segment 220 has a series of recesses 272 that extend inwardly from trailing edge 223. These recesses 272 are configured to engage projections 263*a* of intermediate platform segment 230*a*.

Each intermediate platform segment 230*a-h* also includes a locking mechanism, referred to generally as 500, at each end 231 and 232. In the illustrated example, the locking mechanism 500 includes a slidable pin assembly 510 that can be translated axially along the intermediate platform segment 230*a*. Locking pins 512 extend through corresponding transverse apertures in the projections 261 of the first distal platform segment 210. By engaging and disengaging the locking pins 512 with the projections 261, the intermediate platform segment 230*a* can be selectively connected and disconnected to the first distal platform segment 210.

In the illustrated example, the locking mechanism 500 is spring biased via a compression spring 515 towards a locked position (e.g. as shown in FIG. 23). Also shown in an optional drag assembly 520 to buffer motion of the pin assembly 510.

Preferably, the platform segments 210, 220 and 230*a-h* are secured to each other in a manner that allows for degree of flexion between adjacent platform segments. This may facilitate articulation of transfer platform 250 during use. Such degree of flexion for the articulated transfer platform 250 may have one or more advantages, for example the articulated transfer platform 250 may be able to conform to an object that has a curved lower surface (e.g. a patient) and/or to a surface on which the object may be resting (e.g. a soft mattress).

In the illustrated example, the projections 261 are mounted on a resilient plate 281. An edge of the resilient plate 281 is secured to the first distal platform segment 210, providing a cantilevered-type connection between adjacent connected platform segments. Similarly, the projections 263*a* are mounted on a resilient plate 283. An edge of the resilient plate 283 is secured to the intermediate platform segment 230*a*.

Preferably, the dimensions, thickness and/or material of the resilient plates 281 and 283 are selected in order to provide a desired degree of bias force directing adjacent platform segments into an aligned (or neutral) position in which the adjacent segments are generally planar. It will be appreciated that the resilient plate 281 and one or more of the resilient plates 283 may be configured to provide a different degree of bias force.

In one or more alternative embodiments (not shown), the articulated transfer platform 250 may be configured to provide selective tensioning between adjacent platform segments.

Figure 24:
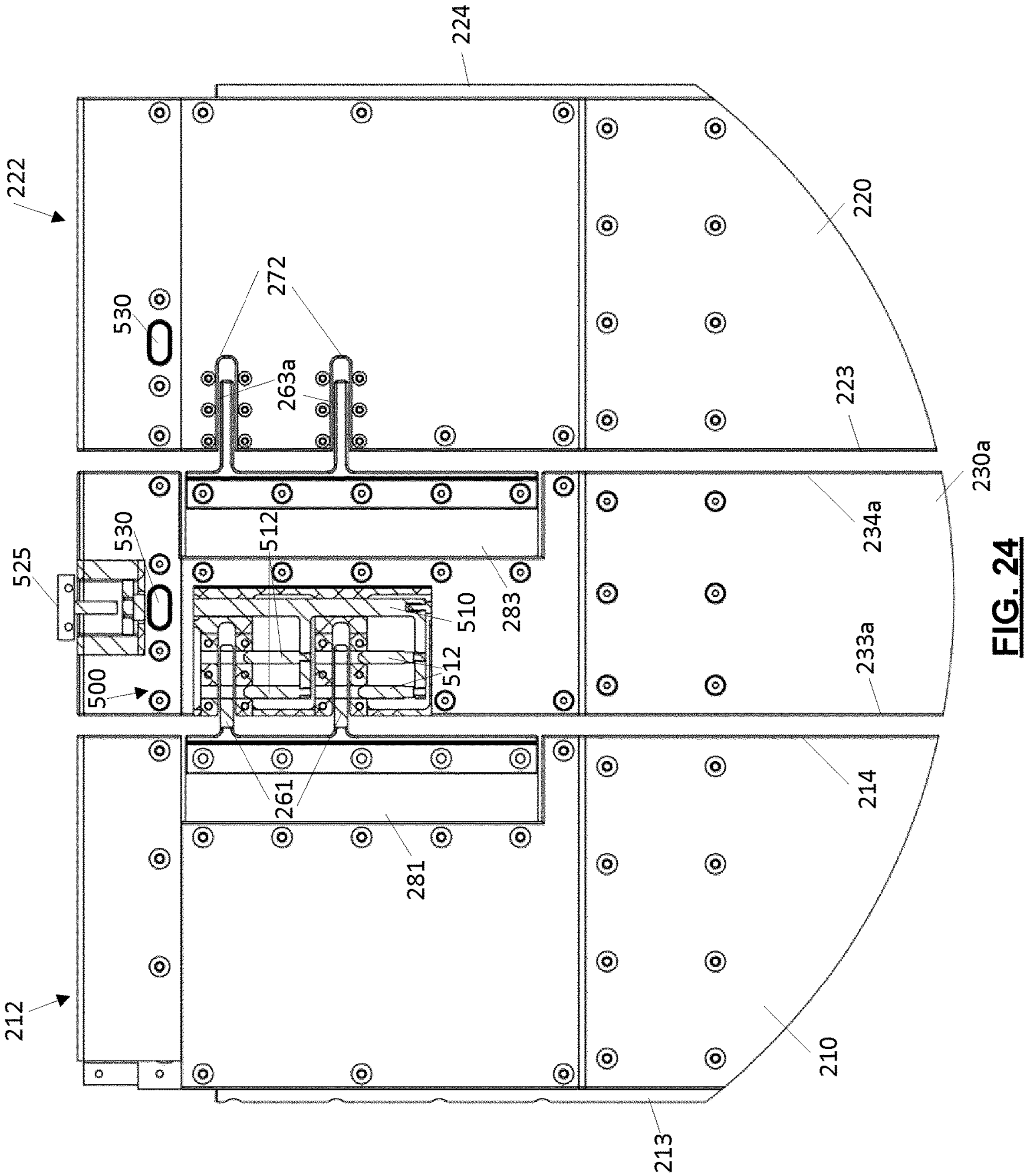
FIG. 24 is a top plan view of an engagement mechanism of an intermediate platform segment, with portions shown in section for clarity, and with the platform segment disengaged from an adjacent distal platform segment.
Figure 25:
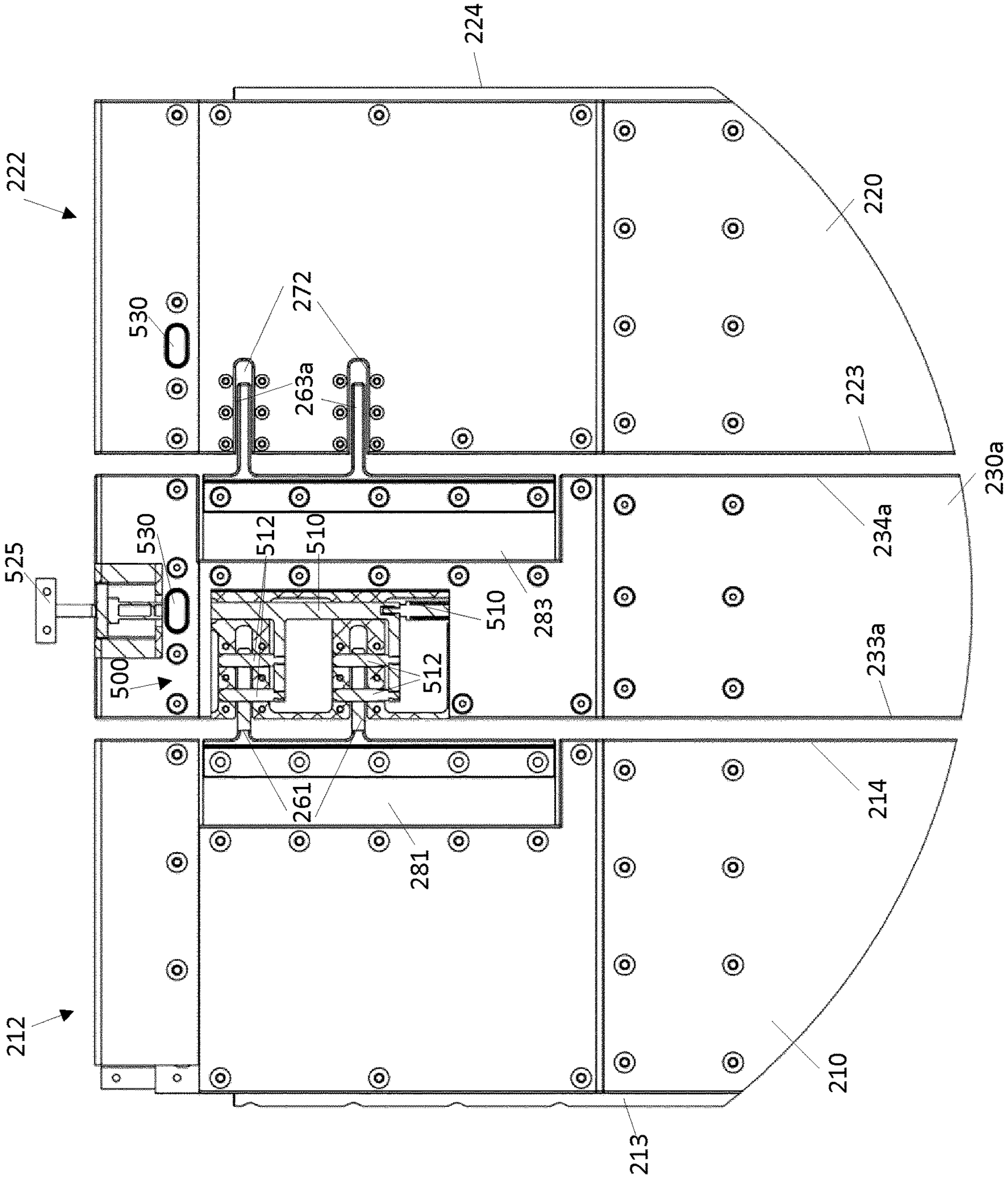
FIG. 25 is a top plan view of the engagement mechanism of FIG. 24, with the platform segment engaged with the adjacent distal platform segment.

Turning to FIG. 24, in this example the slidable pin assembly 510 is shown in a disengaged or unlocked position, in which the locking pins 512 are disengaged from apertures within the projections 261. In FIG. 25, the slidable pin assembly 510 is shown in an engaged or locked position, in which the spring 515 has driven the locking pins 512 into apertures within the projections 261.

Returning to FIG. 23, the optional drag assembly 520 may buffer (e.g. smooth out) motion of the slidable pin assembly 510 as it translates from a retracted position to an engaged position, and from an engaged position to a retracted position.

In illustrated example, the locking pins 512 may be disengaged with projections of an adjacent transfer platform via an actuator connected to the end drive assembly 300*a-b*. For example, an actuator may be selectively actuated to press a plunger 525 inwardly towards intermediate platform segment 230*a*, translating the slidable pin assembly 510 and driving the locking pins 512 out of engagement with apertures within the projections 261, thereby decoupling the platform segments 210, 220 and 230*a-h* from each other. In order to secure adjacent segments, a release button 530 may be depressed to disengage the slidable pin assembly 510 from a latching mechanism (not shown), allowing the spring 515 to drive the locking pins 512 into engagement with apertures within the projections 261.

In the illustrated example, the slidable pin assembly 510 includes four of the locking pins 512. However, it will be appreciated that more or fewer pins may be provided, and that they may be provide in any suitable configuration. Also, while the locking pins 512 are cylindrical, it will also be appreciated that the locking pins 512 may have one or more other geometries (e.g. a single pin with a square profile, or multiple pins with geometries that are the same or different from each other). For example, this may assist in achieving different mechanical performance for the articulated transfer platform 250.

Figure 26:
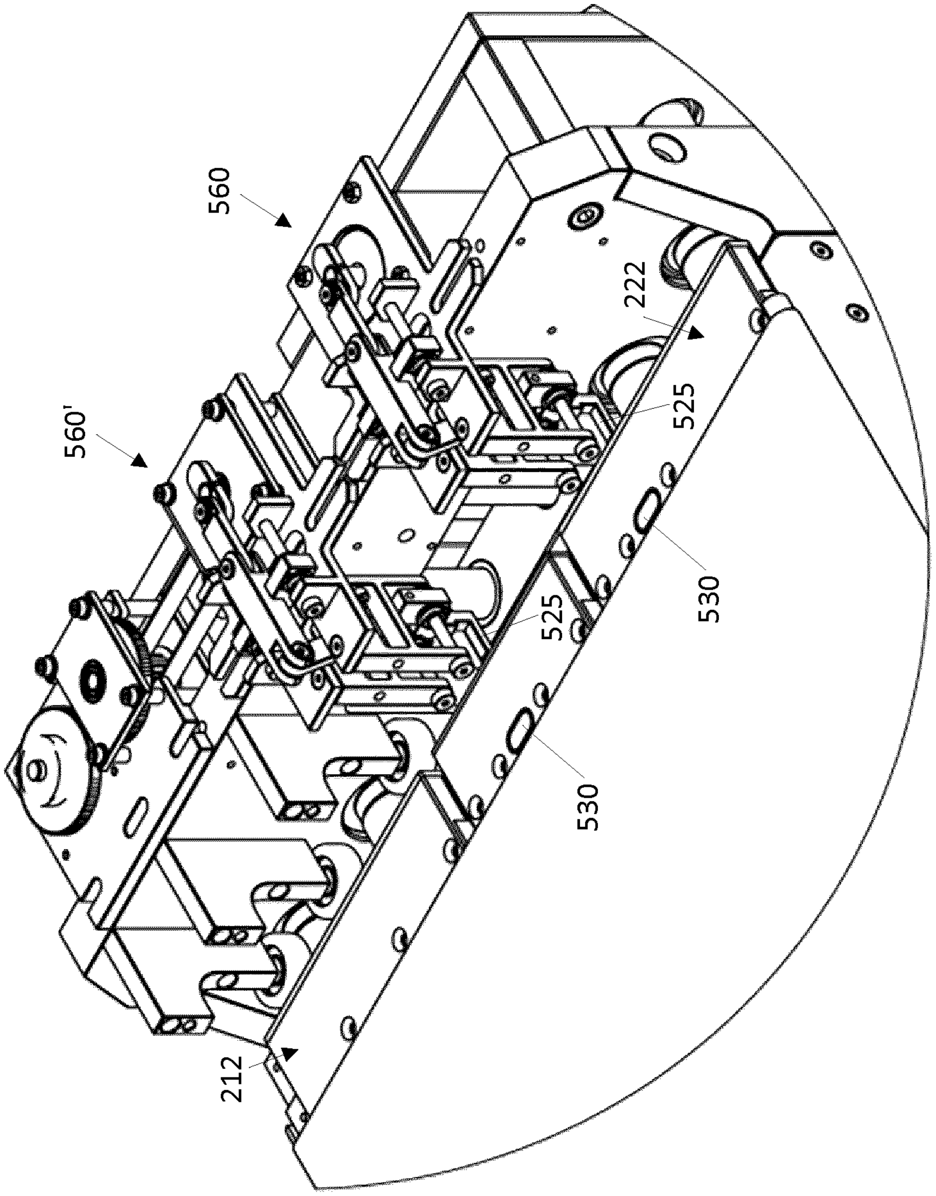
FIG. 26 is a top perspective view of an end of a transfer device, with housing portions and other components removed for clarity.
Figure 27:
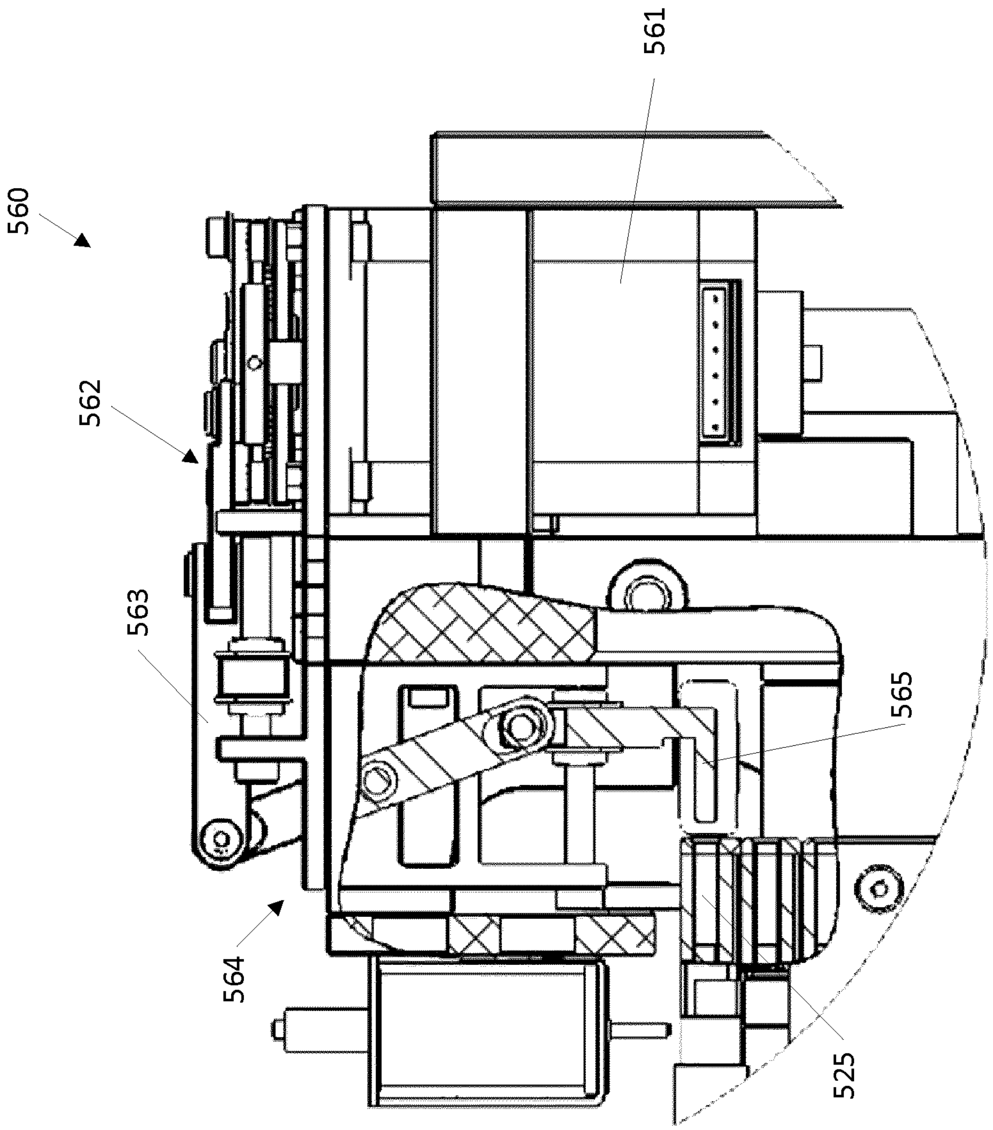
FIG. 27 is a side plan view of the end of a transfer device of FIG. 26, with housing portions and other components removed or shown in partial section for clarity.
Figure 28:
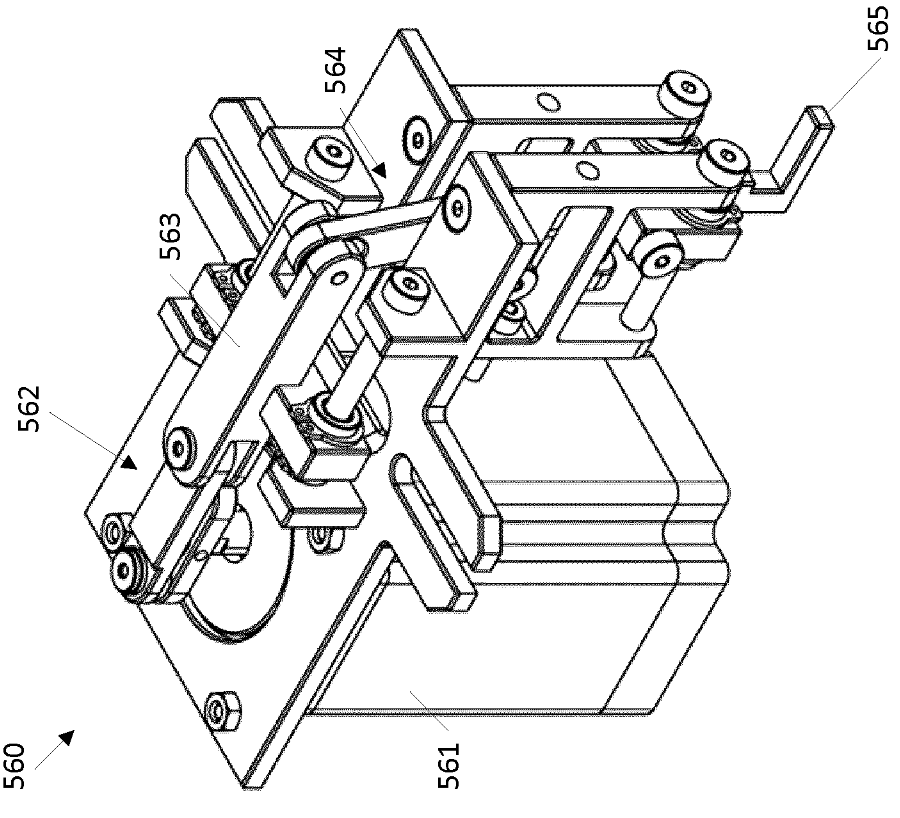
FIG. 28 is a perspective view of an engagement actuator, in accordance with one embodiment.
Figure 29:
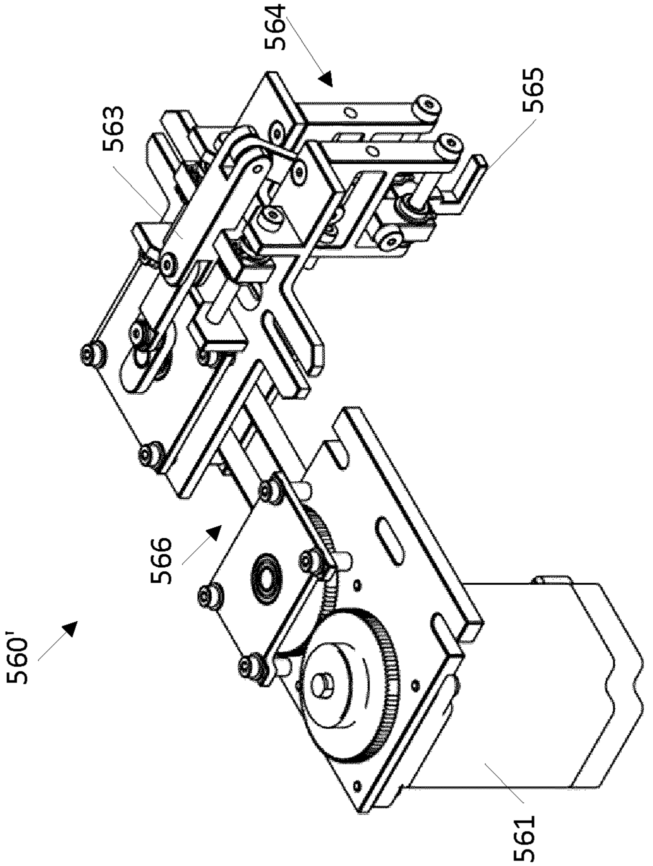
FIG. 29 is a perspective view of an offset engagement actuator, in accordance with one embodiment.
Figure 31:
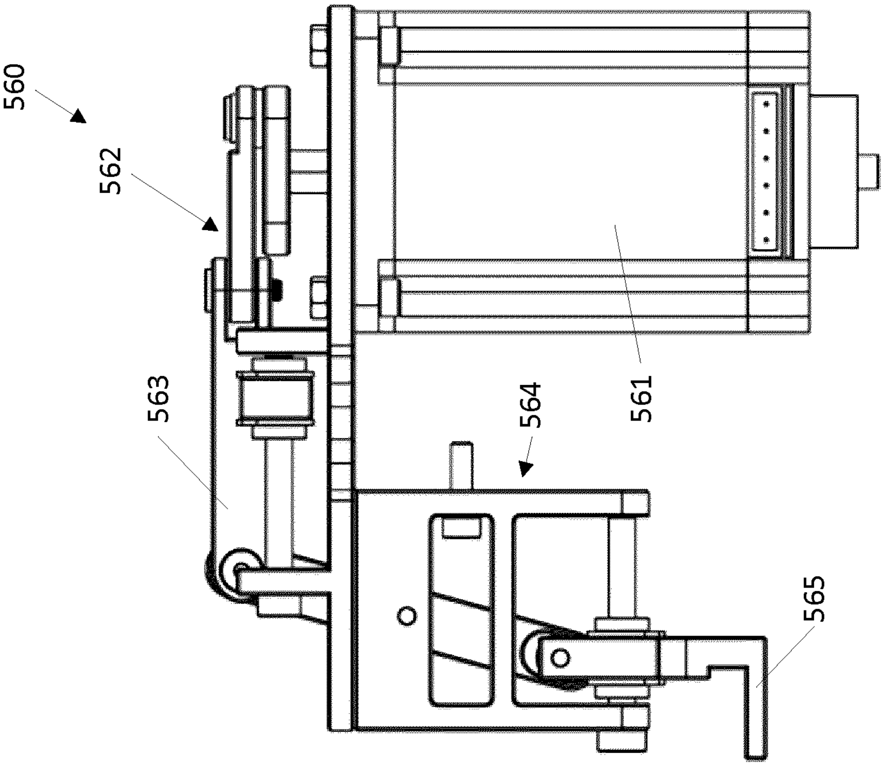
FIG. 31 is a side plan view of the engagement actuator of FIG. 28, with the engagement arm in a second position.
Figure 30:
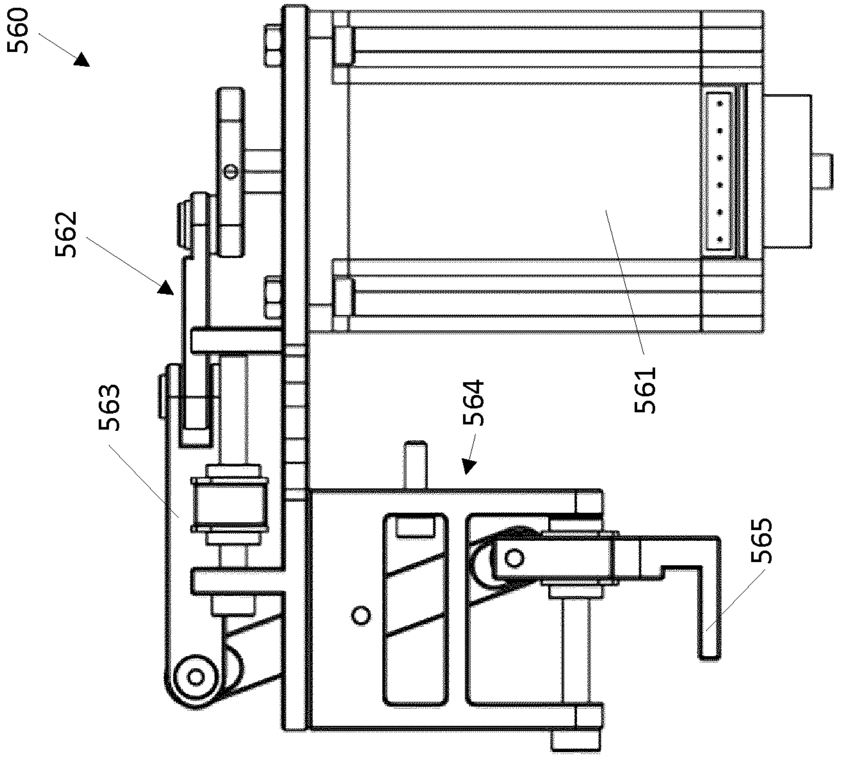
FIG. 30 is a side plan view of the engagement actuator of FIG. 28, with the engagement arm in a first position.

FIGS. 26 to 31 illustrate examples of an engagement actuator 560 that may be used to press the plunger 525 inwardly towards the intermediate platform segment 230*a*. With reference to FIG. 28, the engagement actuator 560 includes a rotary motor 561, a reciprocating linkage 562 that translates rotary motion of the rotary motor 561 to linear motion of an arm 563, and an engagement end 565 that is connected to the arm 563 through a linkage 564. With reference to FIGS. 30 and 31, by selectively retaining the rotary motor 561, the engagement end 565 can be reciprocated between a first position (e.g. as shown in FIG. 30) and a second position (e.g. as shown in FIG. 31).

FIG. 29 illustrates an offset engagement actuator 560' with the rotary motor 561 offset from the reciprocating linkage 562, and connected via a gear and belt drive system 566.

Returning to FIGS. 26 and 27, in the illustrated example, the engagement actuator 560 and the offset engagement actuator 560' are secured to an upper end of the end drive assembly 300*a-b*. With reference to FIG. 27, engagement ends 565 are aligned so they can engage and press the plunger 525 inwardly towards the intermediate platform segment 230*a*.

As can be seen in FIG. 26, the offset arrangement of the engagement actuator 560' allows the engagement actuator 560' to be mounted centrally with respect to the end drive assembly 300*a-b*, while allowing clearance for the intermediate platform segment support assembly 400.

Figure 32:
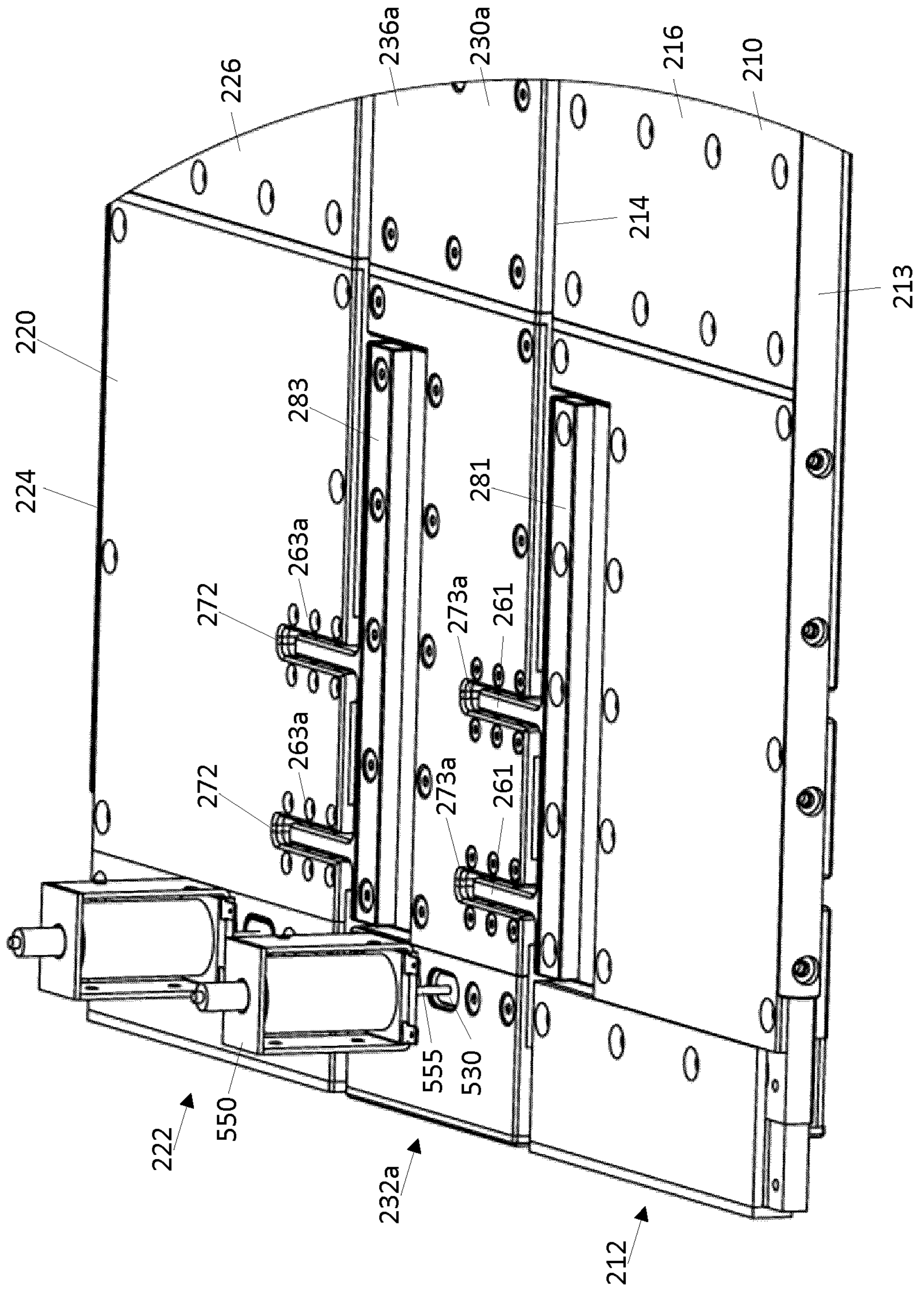
FIG. 32 is a top perspective view of the engagement mechanism of FIG. 24, with a release actuator in a depressed position.
Figure 33:
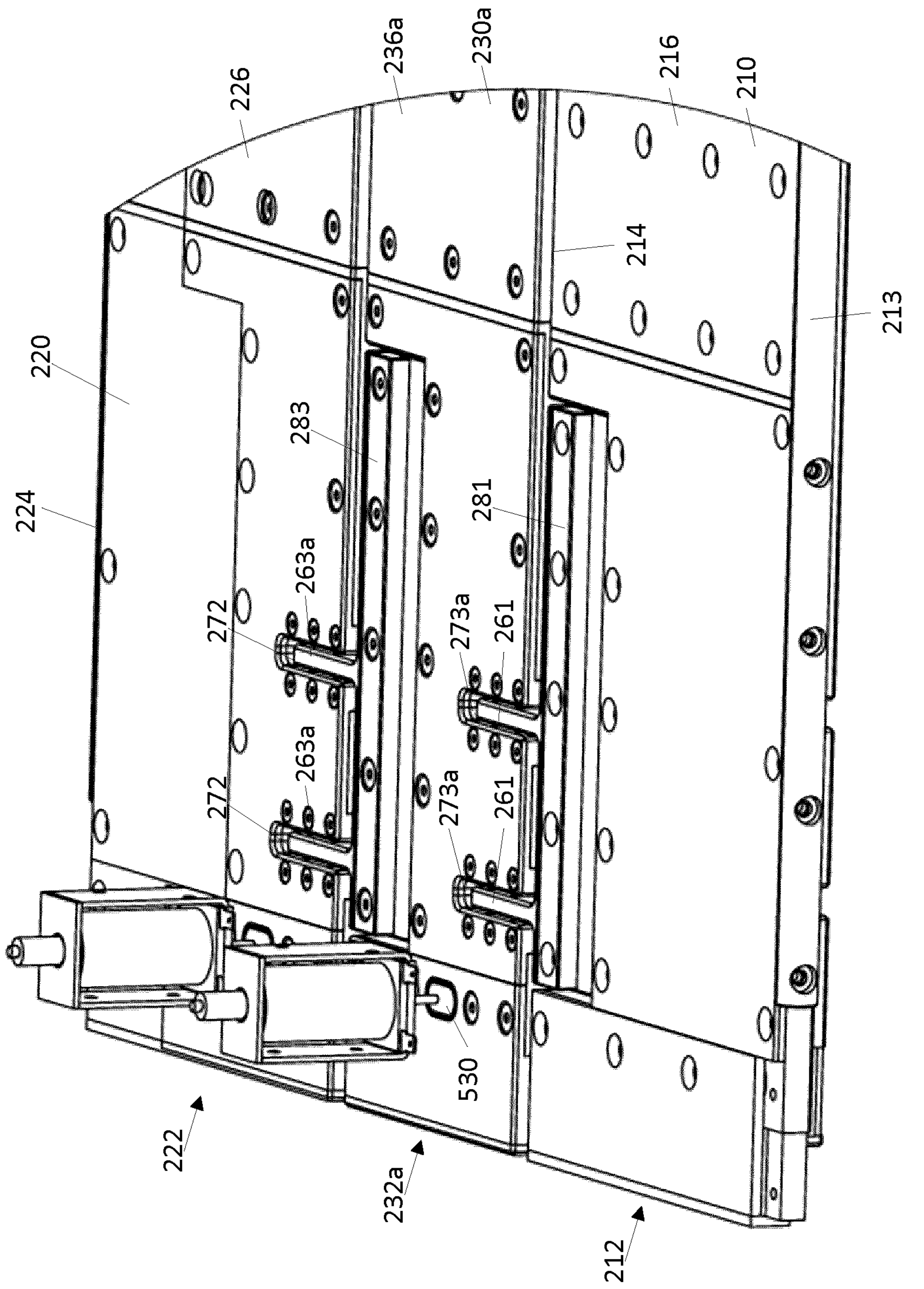
FIG. 33 is a top perspective view of the engagement mechanism of FIG. 24, with the release actuator in a retracted position.

FIG. 32 illustrates an example of release actuators 550 which may be selectively actuated to drive rods 555 downwards to depress release buttons 530, thereby allowing the slidable pin assembly 510 to engage adjacent transfer platforms.

In the illustrated example, the slidable pin assembly 510 is biased into a locked position. It will be appreciated that the slidable pin assembly 510 may alternatively be biased into an unlocked position.

A schematic example of a 'build out' of transfer platform 250 will be now be described with reference to FIGS. 34 to 36.

As shown in FIG. 34, in a retracted position, the distal platform segments 210 and 220 and the lead intermediate platform segment 230*a* are generally aligned with each other and provide a support platform of transfer device 100.

Figure 35:
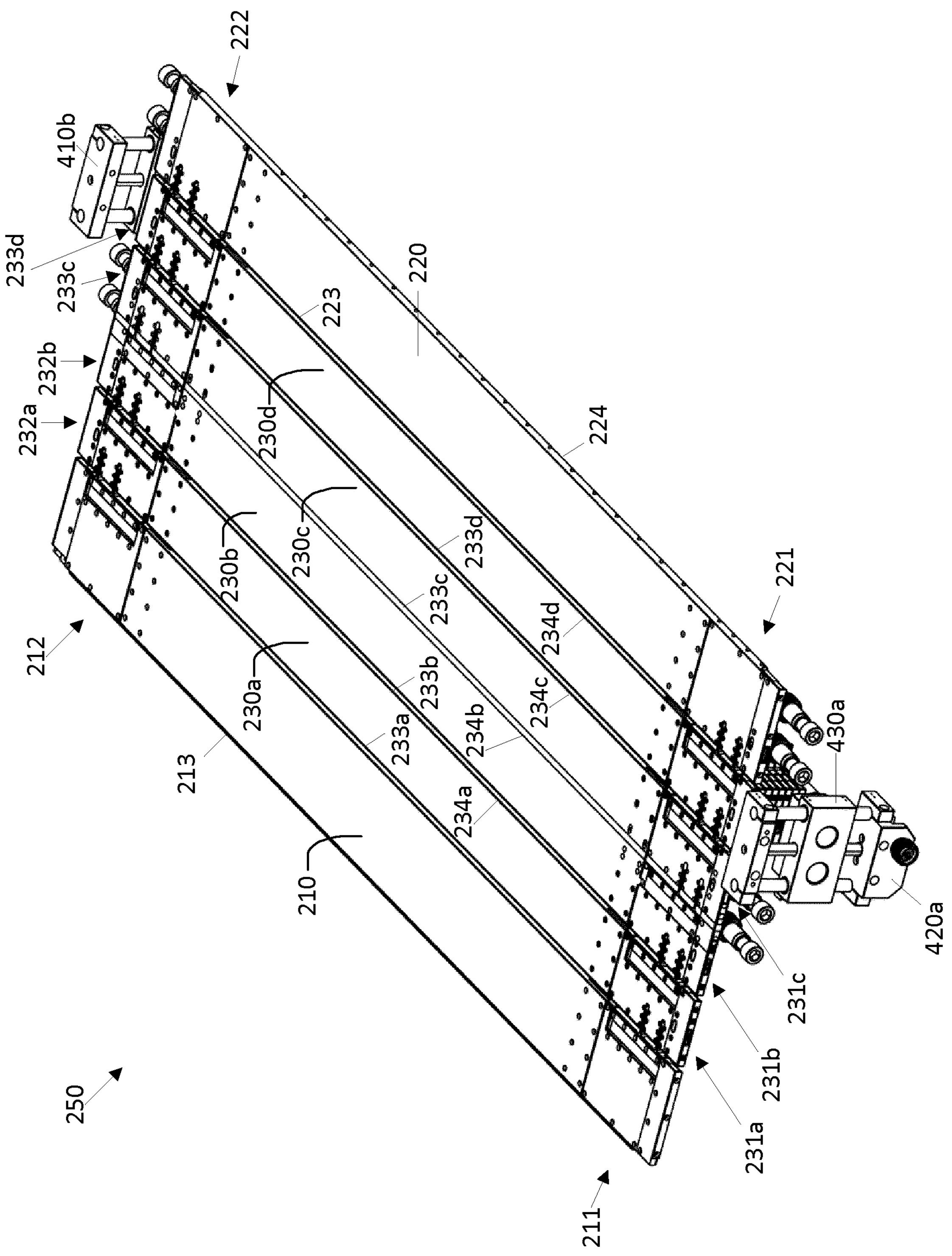
FIG. 35 is a perspective view of the platform segments, intermediate platform segment supports, and platform drive pinions of FIG. 34, with the platform segments in a partially extended position.

Turning FIG. 35, the first distal platform segment 210 and the successive intermediate platform segments 230*a-d* have been driven outwardly by the rotating pinions 382 of the end drive assembly 300, extending the transfer platform 250. As a second edge of a given "nth" intermediate platform segment (e.g. segment 230*b*) has been moved outwardly into a position where it overlies a first edge of a subsequent "n+1" intermediate platform segment (e.g. segment 230*c*), the translating frame member 430 has been raised in order to raise the "n+1" intermediate platform segment (e.g. segment 230*c*), thereby aligning the edges of the "nth" and "n+1" adjacent intermediate segments (e.g. segments 230*b* and 230*c*), at which point the actuator 550 may be used to connect the "n" and "n+1" adjacent intermediate segments to each other. This process may be repeated until all of the intermediate platform segments 230*a-h* have been secured to each other and the transfer platform 250 is fully extended outward as shown in FIG. 36 for example.

In order to retract the transfer platform 250, the transfer device 100 may be operated in substantially the same way, but in reverse. For example, an "n+1" intermediate platform segment (e.g. segment 230*d*) may be disengaged from an adjacent "n" intermediate platform segment (e.g. segment 230*c*), for example by depressing the release buttons 530 using the release actuators 550, and then lowered into the volume V of the device body 110, for example via the translating frame member 430. Once the disengaged "n+1" platform segment (e.g. segment 230*d*) has been displaced vertically below the platform segment to which it was formerly attached, the pinions 382 may be driven in order to retract the transfer platform 250 towards the device body 110, until the "n" intermediate platform segment (e.g. segment 230*c*) is in a central position where it can be disengaged from an adjacent platform segment. This process may be repeated until transfer platform 250 is fully retracted.

In addition to 'building out' the transfer platform 250 from only one side of the device body 110, transfer platforms may be extended (at least partially) from both sides of the device body 110. For example, the first distal platform segment 210 and one or more intermediate platform segments 230*a-h* may be driven outwardly, and after a second edge of an intermediate segment 230*a-h* has been connected, the second distal platform segment 220 and one or more intermediate platform segments 230*a-h* may be driven outwardly, and another intermediate segment 230*a-h* may be raised and connected.

In the examples illustrated in FIGS. 1 to 36, the articulated transfer platforms 250 are supported by the device body 110 when in a retracted position, and are cantilevered from the device body 110 when extended (partially or fully). For example, with reference to FIG. 10, the first and second distal platform segments 210 and 220 are supported by the rollers 440*a-d* when in a retracted position, and the intermediate platform segments 230*a-h* are supported by the rollers 440*e* and 440*f* (which extend between the movable frame members 430*a* and 430*b*).

FIGS. 38 to 41 illustrate an example embodiment of the transfer device 100 that includes platform extension supports 570*a-b* that can be used to increase the width of the supported (i.e. non-cantilevered) surface. Such a design may have one or more advantages. For example, it may provide increased patient comfort and or safety when using the transfer device 100 to move a patient resting on the platform from one room to another.

Figure 38:
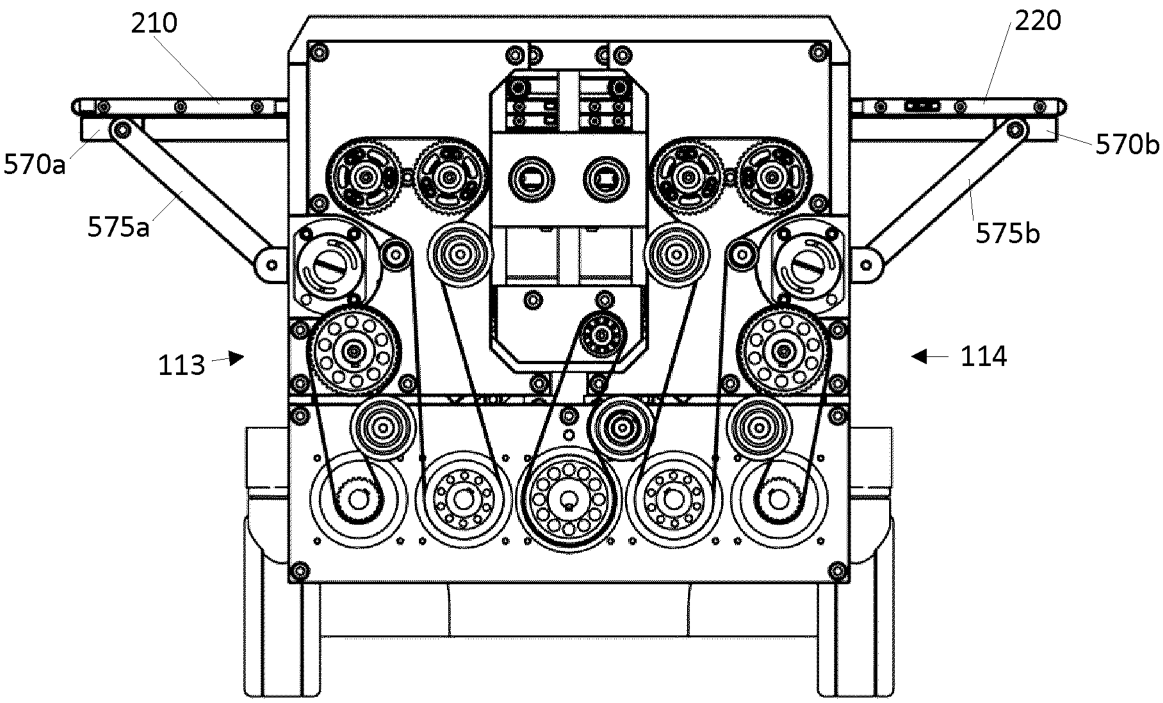
FIG. 38 is an end plan view of a transfer device in accordance with another embodiment, with housing portions omitted for clarity, and with platform extension supports in an extended position.
Figure 40:
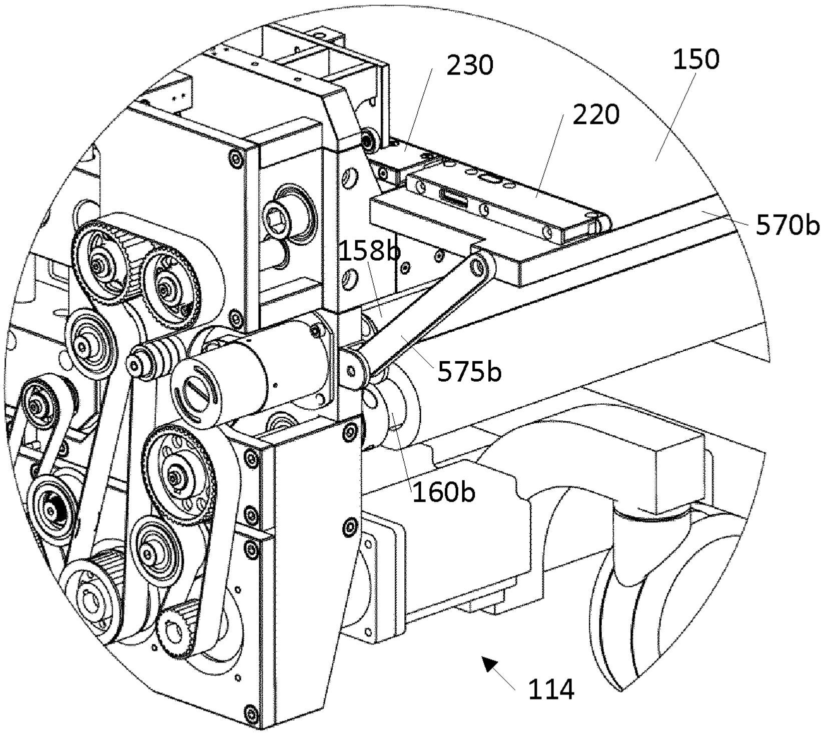
FIG. 40 is a perspective view of a portion of the transfer device of FIG. 38.

With reference to FIGS. 38 and 40, a first platform extension support 570*a* extends outwardly from the first side 113 of the device body 110, and a second platform extension support 570*b* extends outwardly from the second side 114 of the device body 110. In the illustrated example, each platform extension support 570*a-b* is supported by one or more support arms 575. The support arms 575 are connected to the device body 110 below their respective platform extension supports 570, and provide vertical support for the platform extension supports 570 and the articulated transfer platforms 250 resting thereon.

Figure 39:
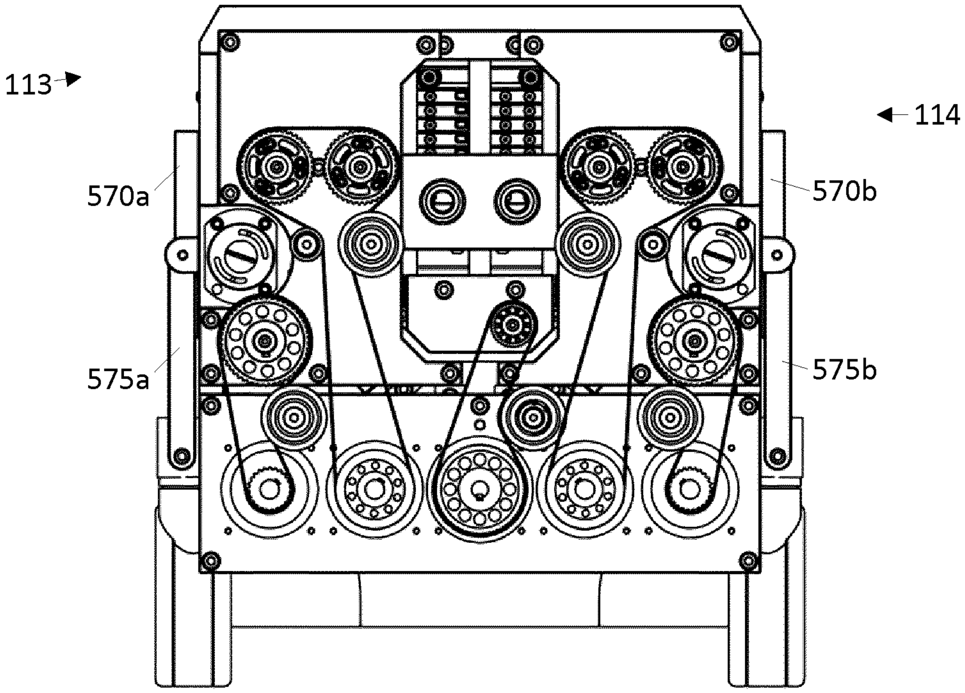
FIG. 39 is an end plan view of the transfer device of FIG. 38, with platform extension supports in a stowed position.
Figure 41:
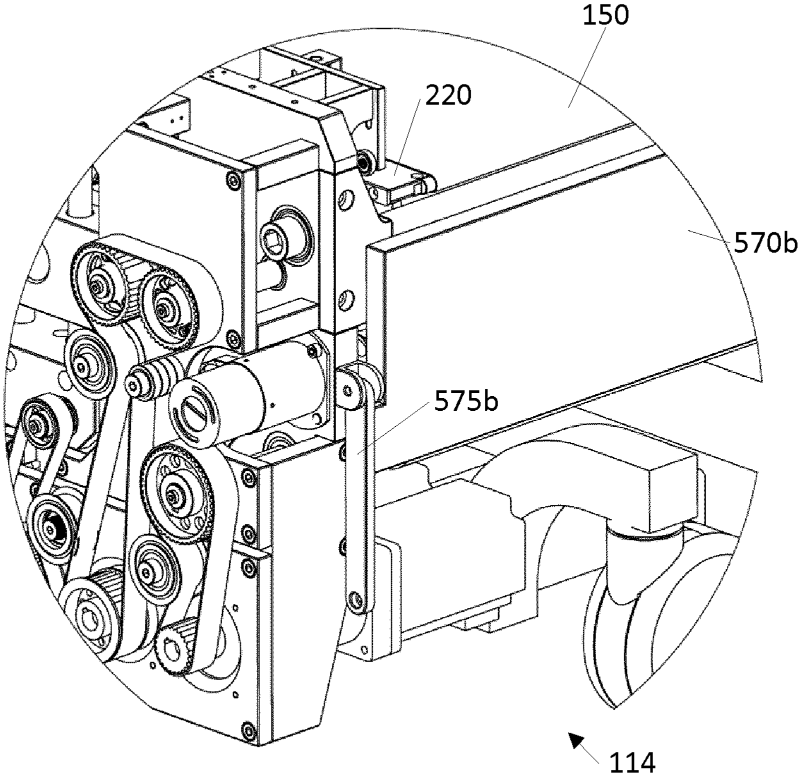
FIG. 41 is a perspective view of a portion of the transfer device of FIG. 39.

With reference to FIGS. 39 and 41, in the illustrated example each platform extension support 570*a-b* is pivotally connected to the device body 110 (e.g. using a hinge or other suitable connection) and each support arm 575 is pivotally connected to the device body 110 and releasably securable to the platform extension support 570*a-b*. An advantage of this design is that the platforms extension supports 570*a-b* can be folded inwardly when not needed, for example as shown in FIGS. 39 and 41, to provide a smaller storage footprint for the transfer device 100.

In the illustrated example, the platform extension supports 570*a-b* are generally rectangular planar support surfaces. It will be appreciated that in one or more alternative embodiments, platform extension supports may be of different shapes and/or may have different surface features. For example, one or more rollers may be provided on an upper surface of a platform extension support.

Also, in the illustrated example, the platform extension supports 570*a-b* may be manually moved between the positions shown in FIGS. 38 and 40, and the positions shown in FIGS. 39 and 41. In one or more alternative embodiments, one or more platform extension support actuators (either 'passive' actuators, such as gas springs, hydraulic drag cylinders, and the like, or 'active' actuators, such as linear, pneumatic, or hydraulic actuators) may be provided to extend and/or retract platform extension supports automatically, e.g. via a control system of the transfer device 100.

In the example embodiments illustrated in FIGS. 1 to 41, the articulated transfer platforms 250 are "built out" using the intermediate platform segments 230 that are selectively secured and released from engaging with distal platform segments 210 and 220 and with each other. In one or more alternative embodiments, an articulated transfer platform may include a series of platform segments that are permanently coupled to each other.

FIGS. 42 through 69 illustrate an example of the transfer device 100 with one or more articulated transfer platforms that include a series of transfer platform segments that remain coupled to each other during extension and retraction of the articulated transfer platform.

Figure 42:
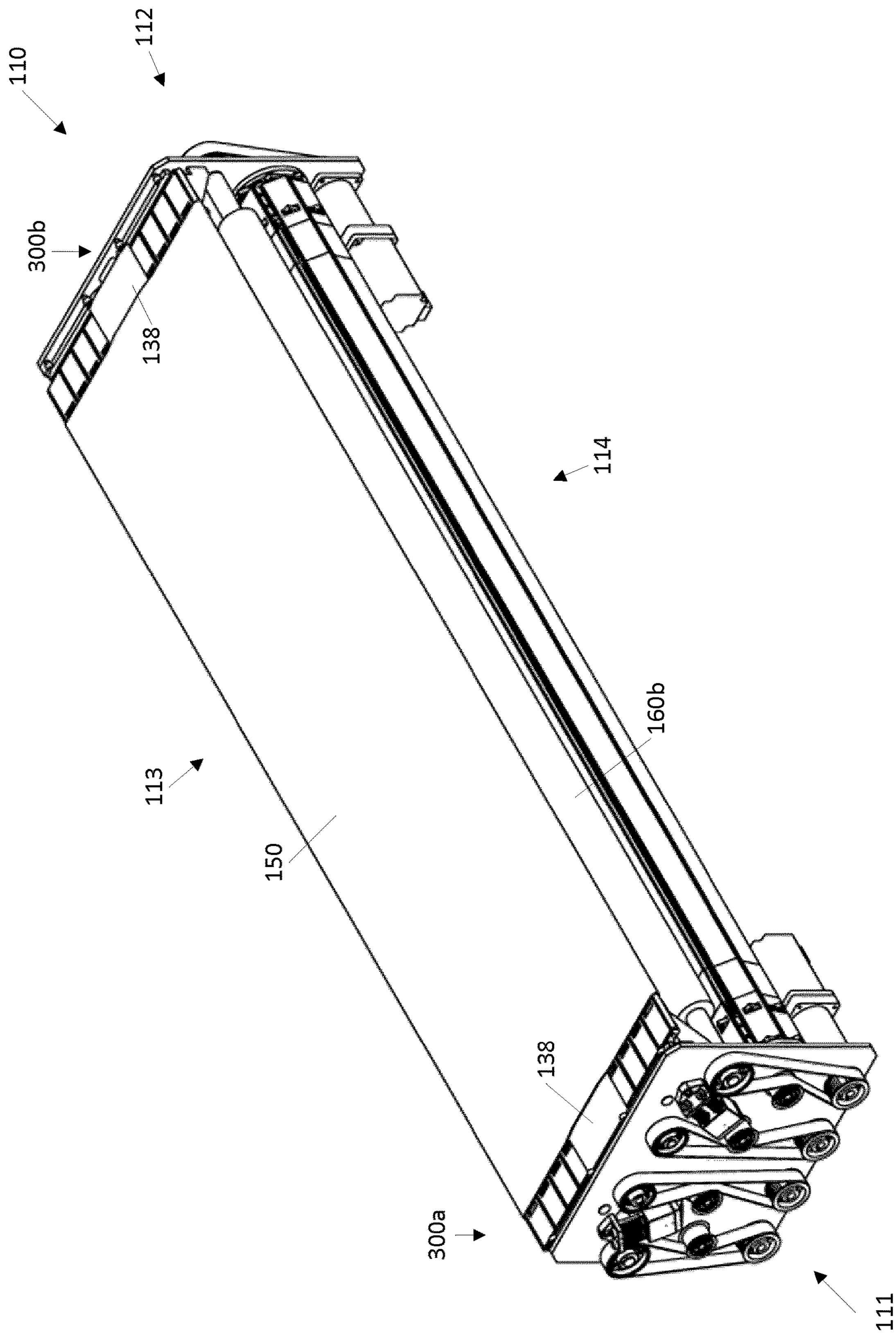
FIG. 42 is a perspective view of a transfer device in accordance with another embodiment, with housing portions and a support base omitted for clarity.
Figure 43:
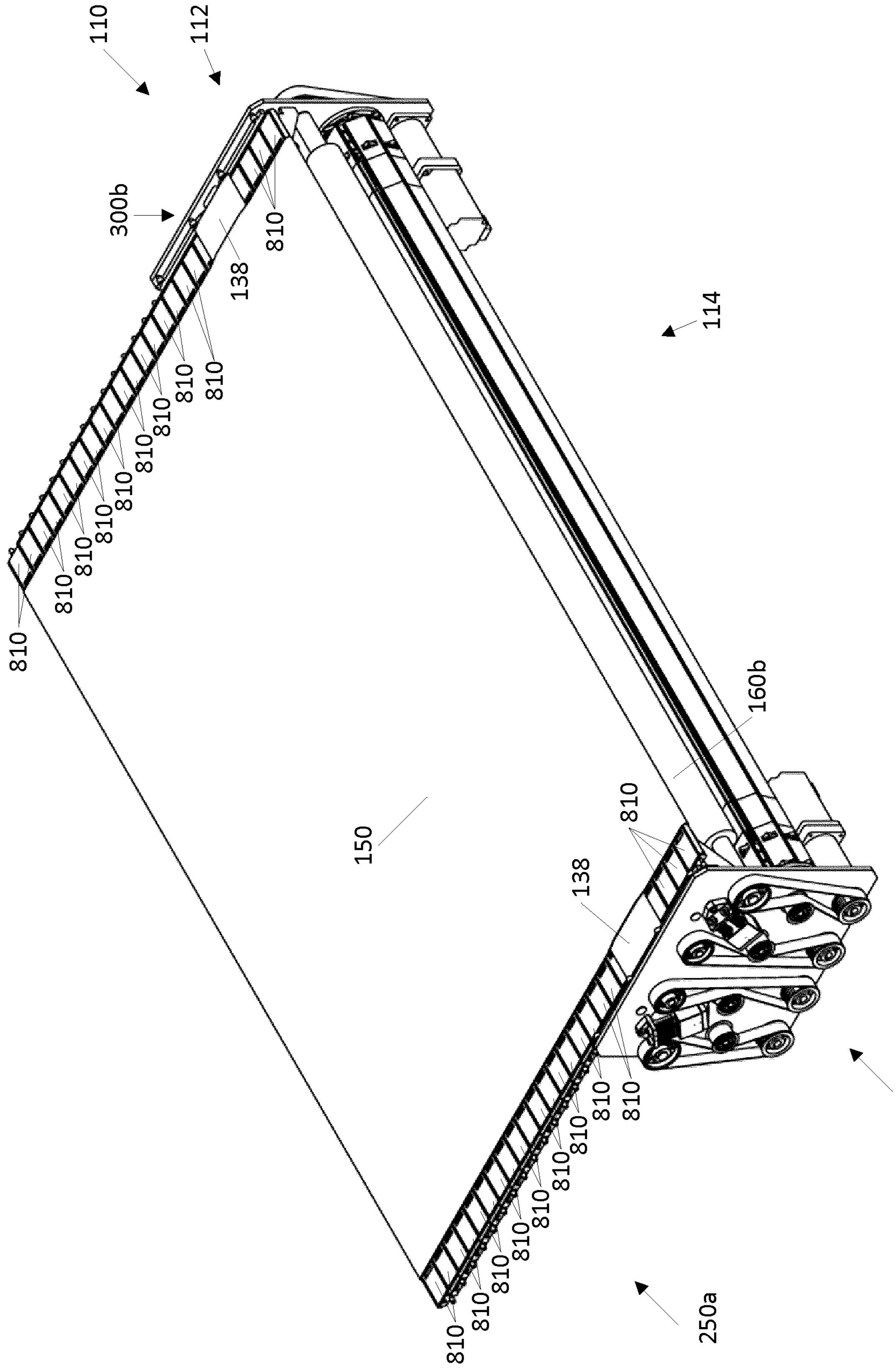
FIG. 43 is a perspective view of the transfer device of FIG. 42, with a first articulated transfer platform in an extended position.
Figure 44:
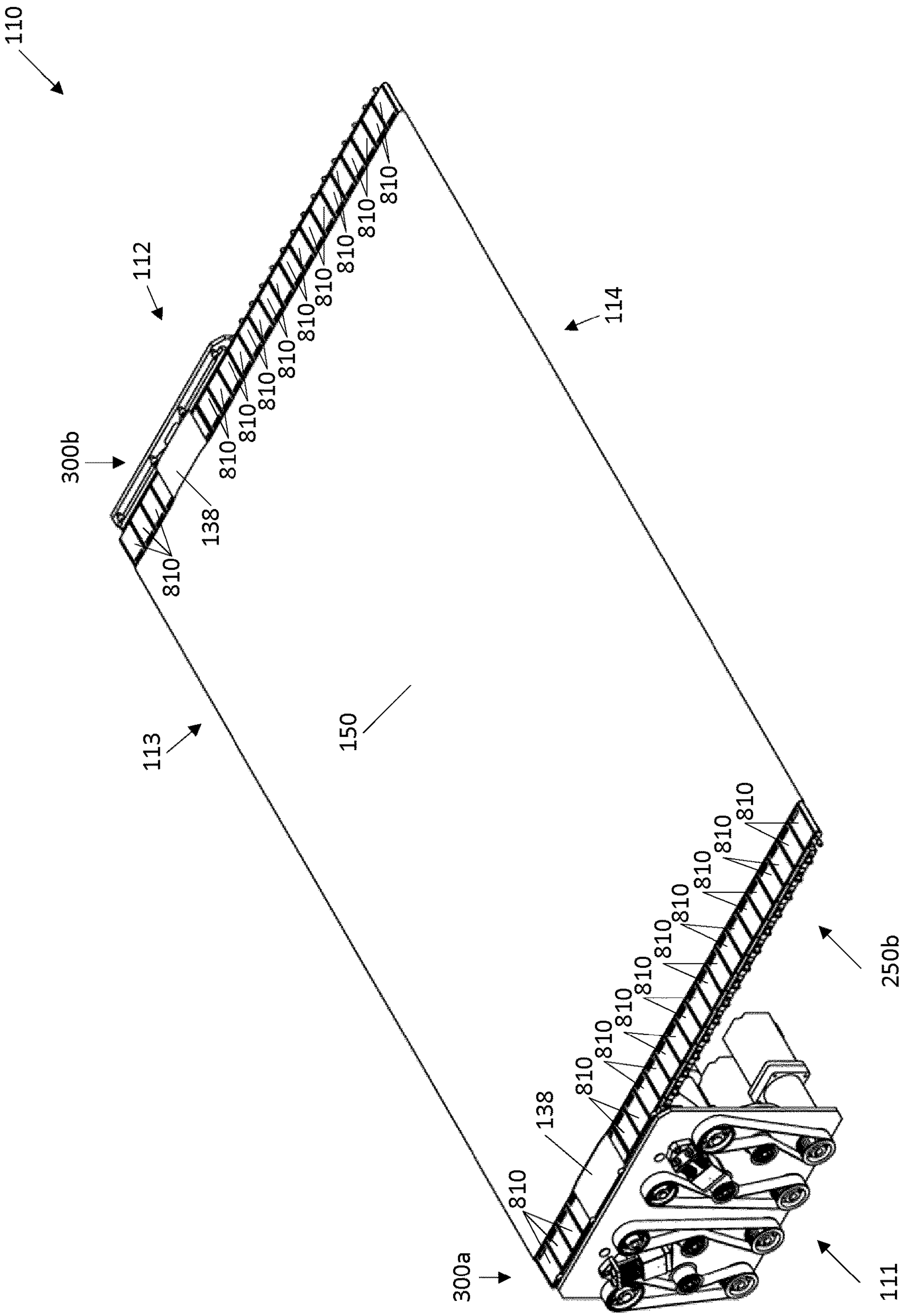
FIG. 44 is a perspective view of the transfer device of FIG. 42, with a second articulated transfer platform in an extended position.
Figure 45:
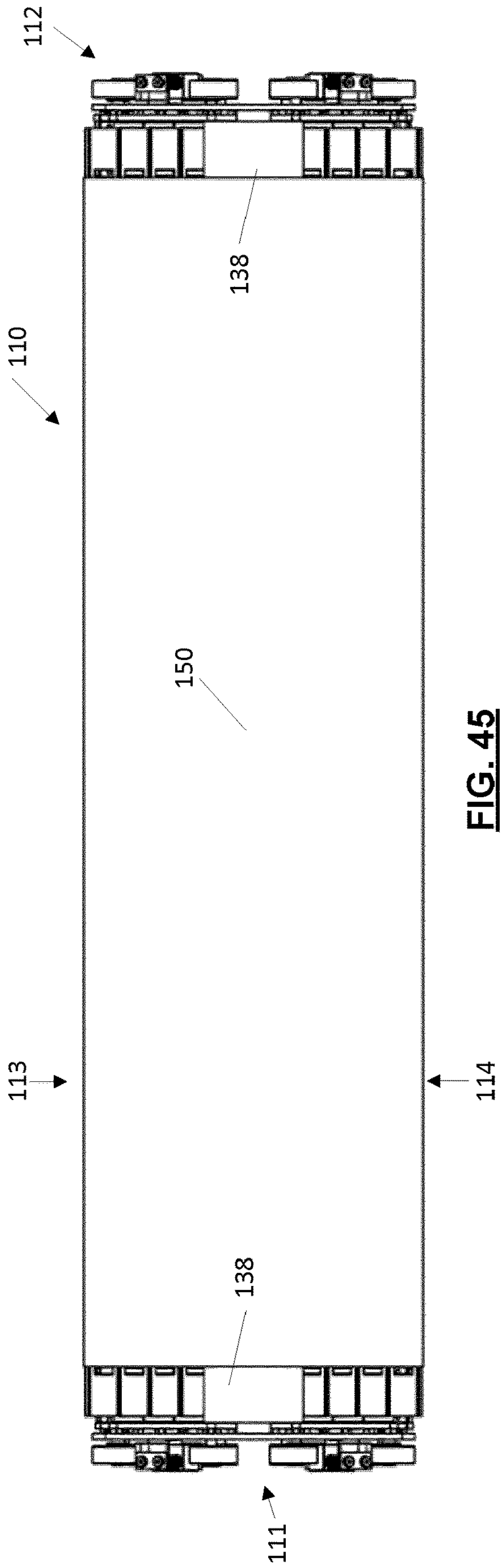
FIG. 45 is a top plan view of the transfer device of FIG. 42.

FIG. 42 illustrates an example of the device body 110 with two articulated transfer platforms, each in a retracted position. In FIG. 43, a first articulated transfer platform 250*a* has been extended outwardly from the first side 113 of the device body 110 to an extended position. The second articulated transfer platform 250*b* is in a retracted position. In FIG. 44, the first transfer platform 250*a* is in a retracted position, and a second transfer platform 250*b* has been extended outwardly from the second side 114 of the device body 110 to an extended position.

Each transfer platform 250 includes a series of platform segments 290. Each platform segment 290 has a first end 291, a second end 292, and a segment link 810 at each end. As discussed further below, the segment links of adjacent platform segments are pivotally coupled to each other, and can selectively be restrained or 'locked' in an aligned position (e.g. in which the platform segments are generally coplanar) to form a relatively rigid articulated transfer platform, and can also be selectively unrestrained or 'unlocked' from an aligned position to allow the platform segments to be stored in a relatively compact arrangement when the articulated transfer platform is retracted.

Figure 46:
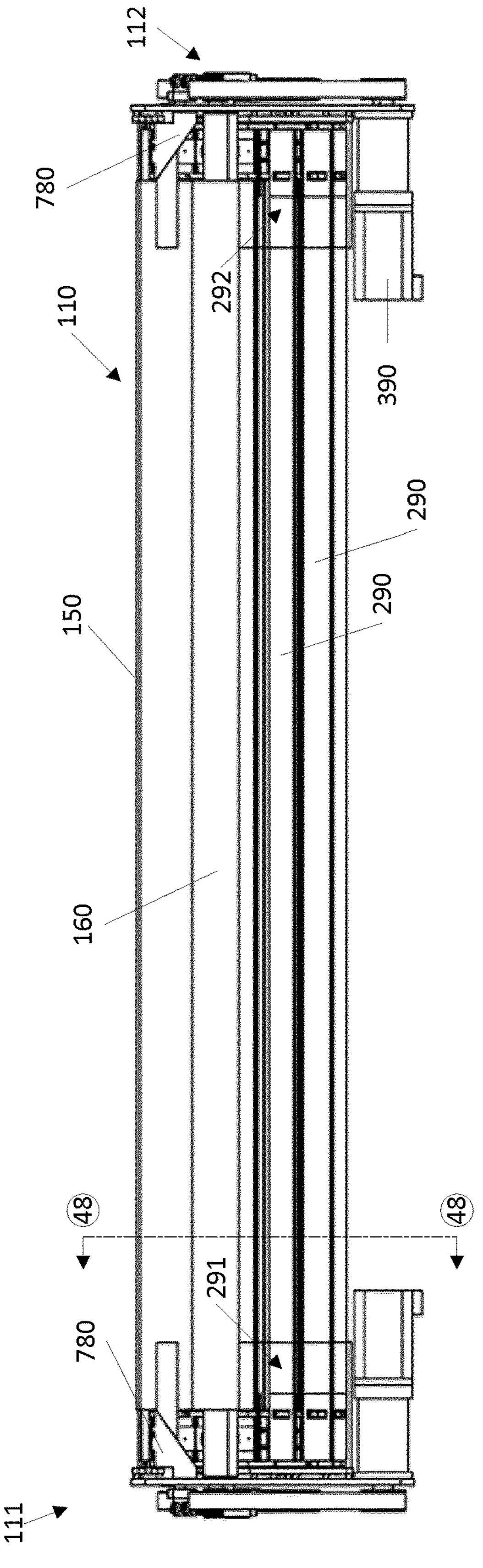
FIG. 46 is a side plan view of the transfer device of FIG. 42.
Figure 47:
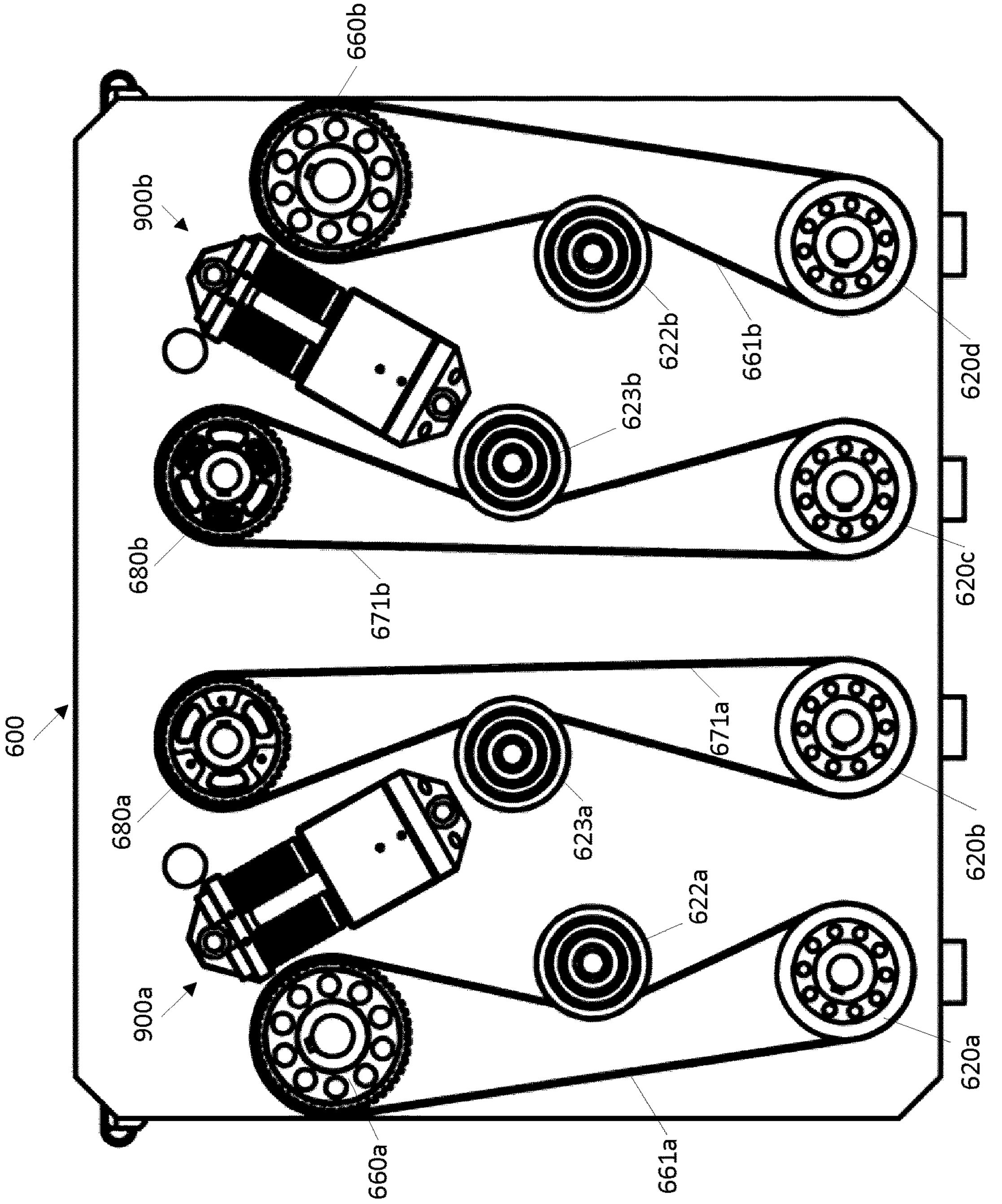
FIG. 47 is an end plan view of the transfer device of FIG. 42.

FIG. 47 illustrates an end view of an outer side of an end drive assembly 600 of the transfer platform of FIGS. 42 to 69. In the illustrated example, first and second belt drive sprockets 620*a* and 620*d* are driven by motors 390*a* and 390*d*, respectively. Belt drive sprockets 620*a* and 620*d* are connected to transfer belt roller sprockets 660*a* and 660*b* by drive belts 661*a* and 661 *b*, respectively. Rotation of transfer belt roller sprockets 660*a* and 660*b* results in rotation of transfer belt rollers 165*a* and 165*b*, respectively. In the illustrated example, tension idlers 622*a* and 622*b* are also provided to control the tension of drive belts 661*a* and 661 *b*, respectively. It will be appreciated that tension idlers 622 are optional.

Also shown are platform drive sprockets 620*b* and 620*c*, which are driven by motors 390*b* and 390*c*, respectively. The platform drive sprocket 620*b* is connected via a drive belt 671*a* to a first drive sprocket 680*a*. The platform drive sprocket 620*c* is connected via a drive belt 671*b* to a second drive sprocket 680*b*. Idlers 623*a* and 623*b* are provided in order to control tension on belts 671*a* and 671*b*, respectively.

Figure 48:
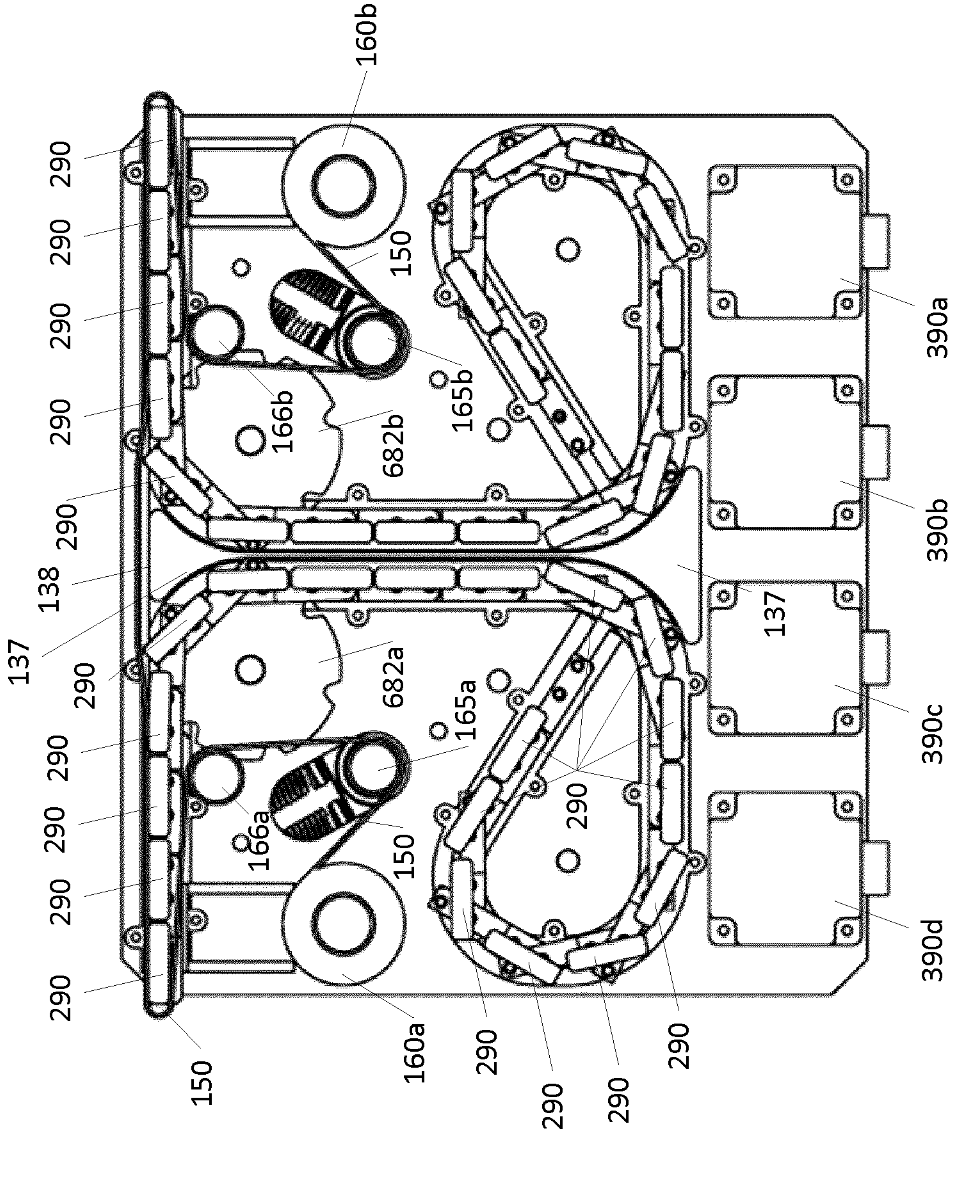
FIG. 48 is a plan section view of an end drive assembly and transfer platforms of the transfer device of FIG. 42, taken along line 48-48 in FIG. 46.

FIG. 48 illustrates an end view of an inner side of the end drive assembly 300*a-b*, taken along line 48-48 in FIG. 46. In the illustrated example, platform drive pinions 682*a* and 682*b* are provided at an upper end of the platform. In the illustrated example, teeth of platform drive pinions 682*a* and 682*b* engage platform segment links 810.

Figure 49:
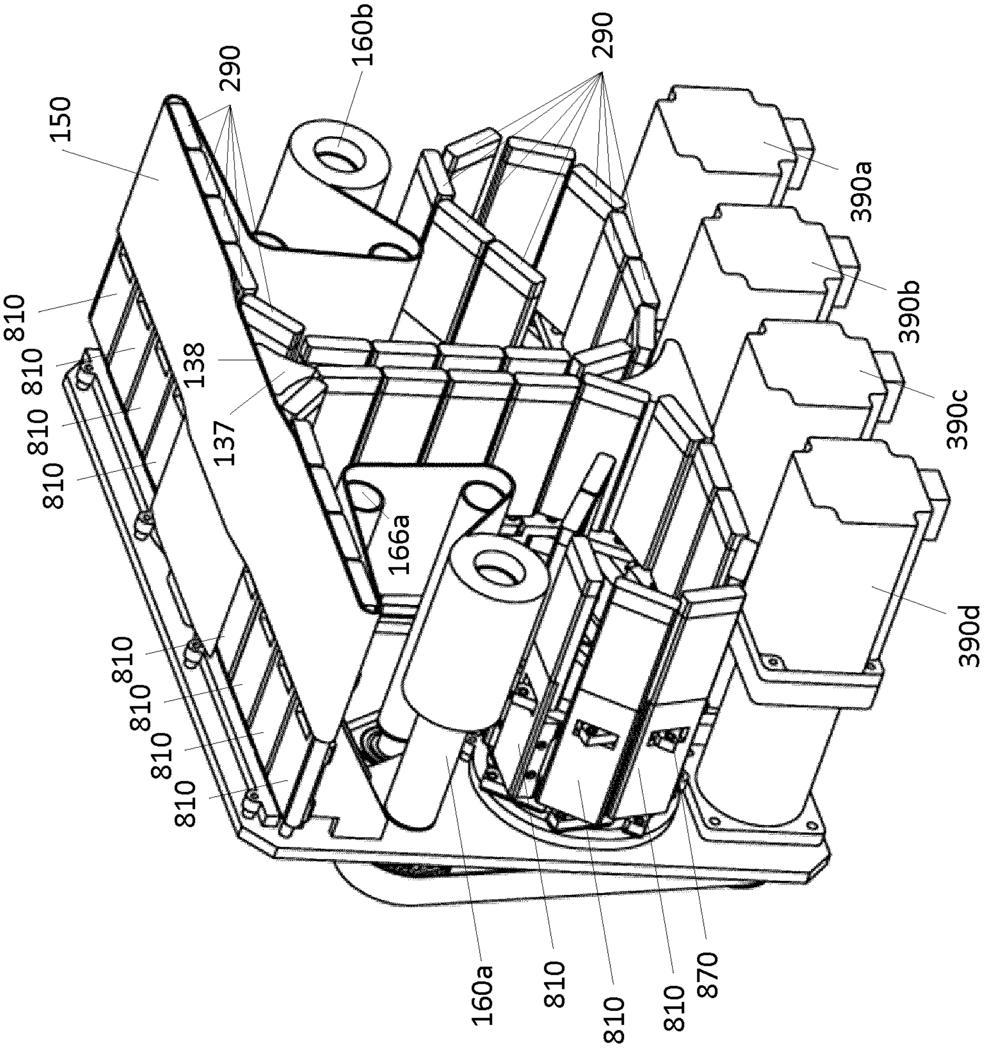
FIG. 49 is a perspective section view of the end drive assembly and transfer platforms of the transfer device of FIG. 42, taken along line 48-48 in FIG. 46, with first and second articulated transfer platforms in stowed positions.

With reference to FIGS. 48 and 49, each articulated transfer platform is guided along an internal track 710 when within the device body 110. Preferably, the segment links of adjacent platform segments are restrained or 'locked' in an aligned position, and unrestrained or 'unlocked' from the aligned position as the platform segments exit and enter the internal track. For example, segment links may be locked or unlocked concurrently with entering/exiting the track, or shortly before entering or exiting the track.

As shown in FIG. 48, the transfer belt 150 extends from a first roller 160*a* around idlers 165*a* and 166*a*, around a leading edge of the first transfer platform, across an upper surface of the first transfer platform, across an upper surface 138 of a central support member 137, across an upper surface of the second transfer platform, around the leading edge of the second transfer platform, around idlers 165*b* and 166*b*, and onto a second roller 160*b*.

Figure 50:
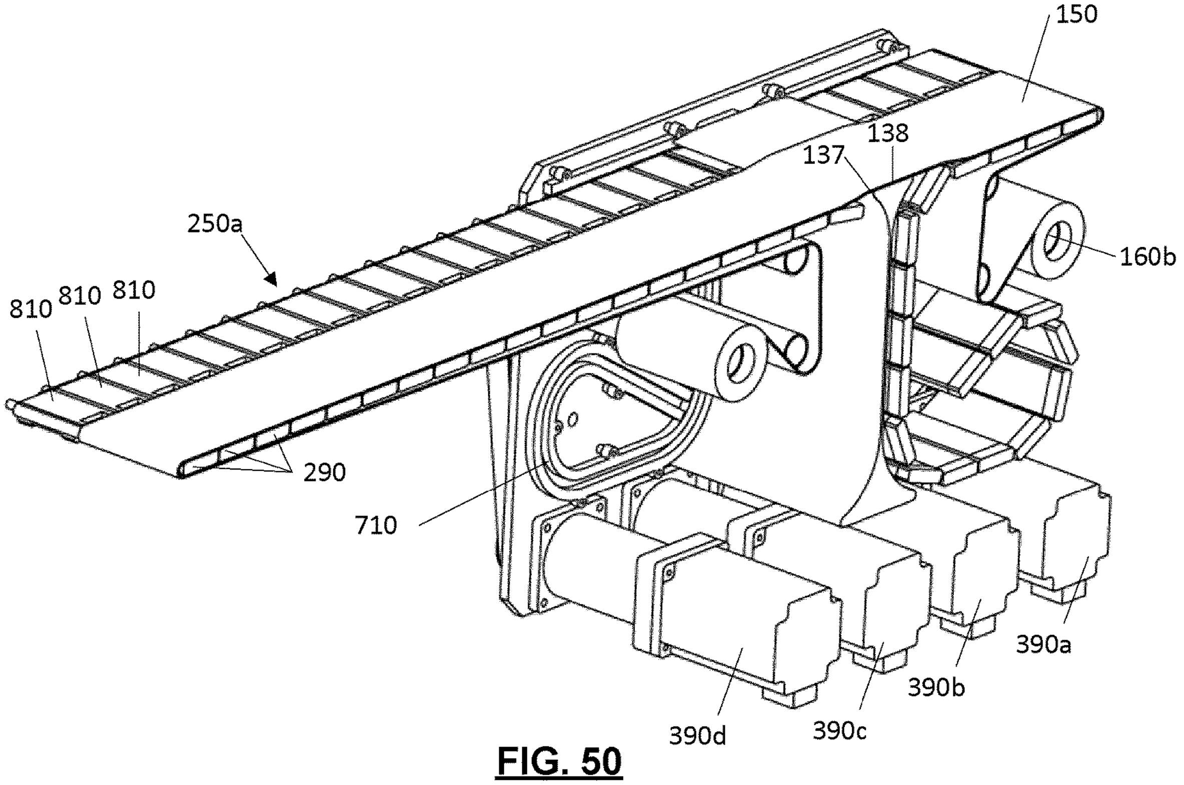
FIG. 50 is a perspective section view of the end drive assembly and transfer platforms of the transfer device of FIG. 42, taken along line 48-48 in FIG. 46, with the first articulated transfer platform in an extended position, and the second articulated transfer platform in a stowed position.
Figure 51:
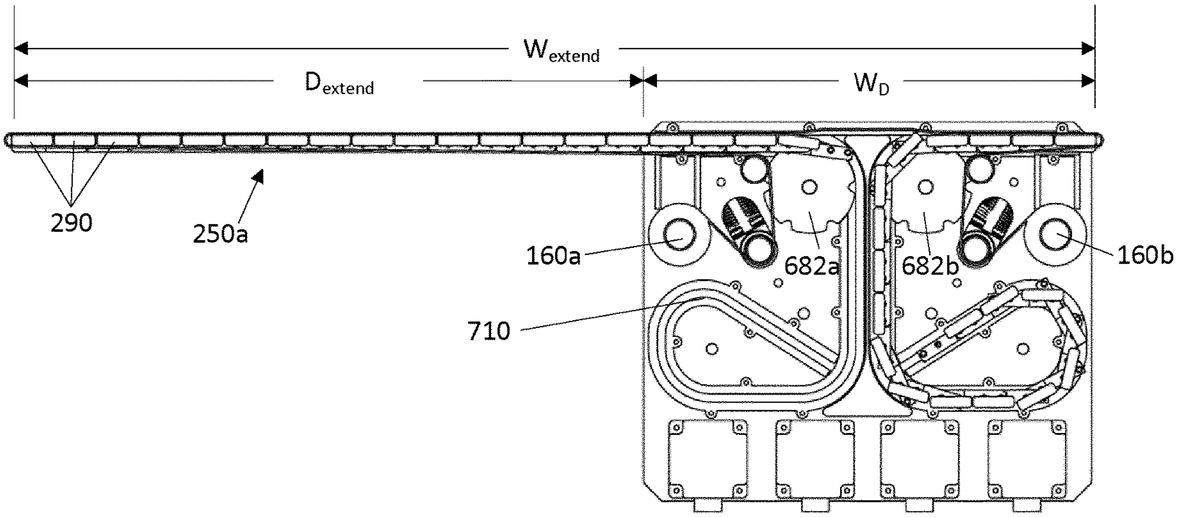
FIG. 51 is a plan section view of the end drive assembly and transfer platforms of FIG. 50.

With reference to FIGS. 50 and 51, the first articulated transfer platform 250*a* can be extended outwardly from the first side 113 of the device body 110. During this extension, the first roller 160*a* and/or the second roller 160*b* may be rotated in order to provide a desired degree of tension along the transfer belt 150.

Figure 52:
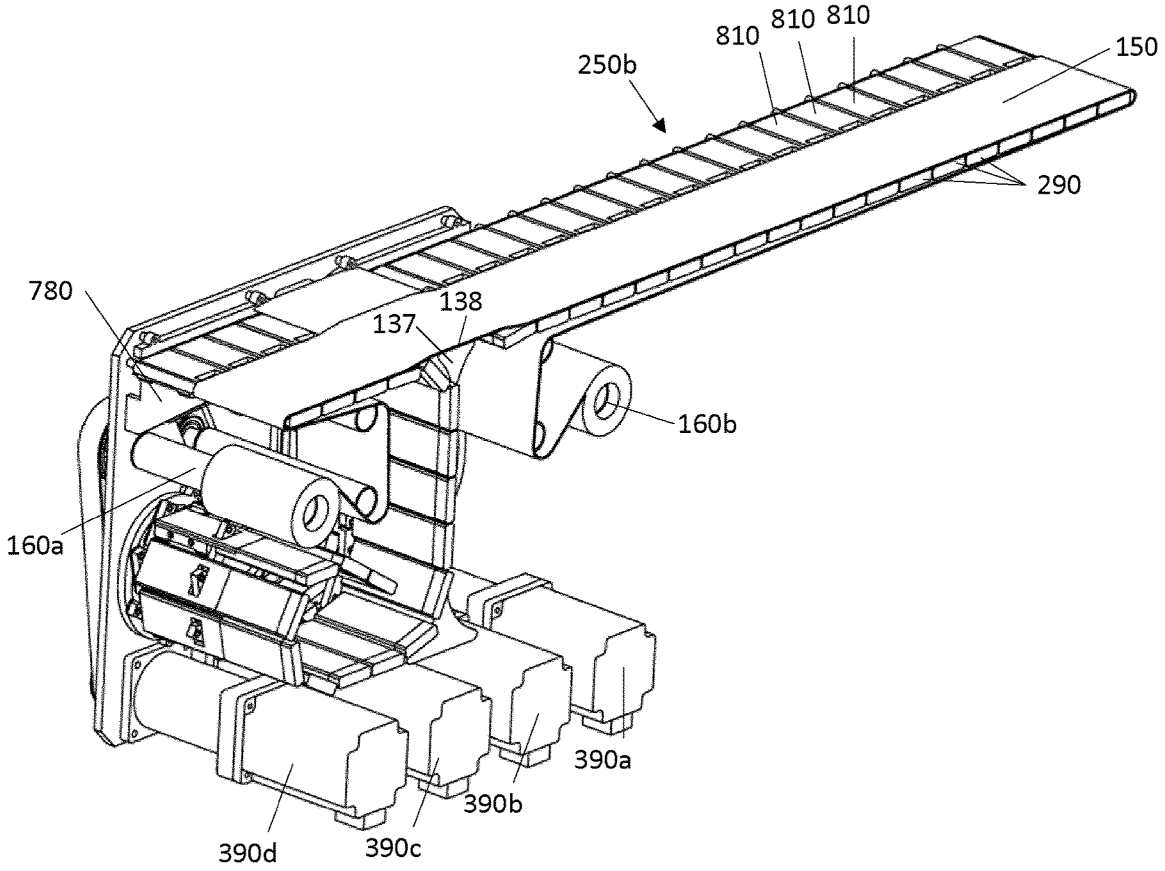
FIG. 52 is a perspective section view of the end drive assembly and transfer platforms of the transfer device of FIG. 42, taken along line 48-48 in FIG. 46, with the first articulated transfer platform in a stowed position, and the second articulated transfer platform in an extended position.
Figure 53:
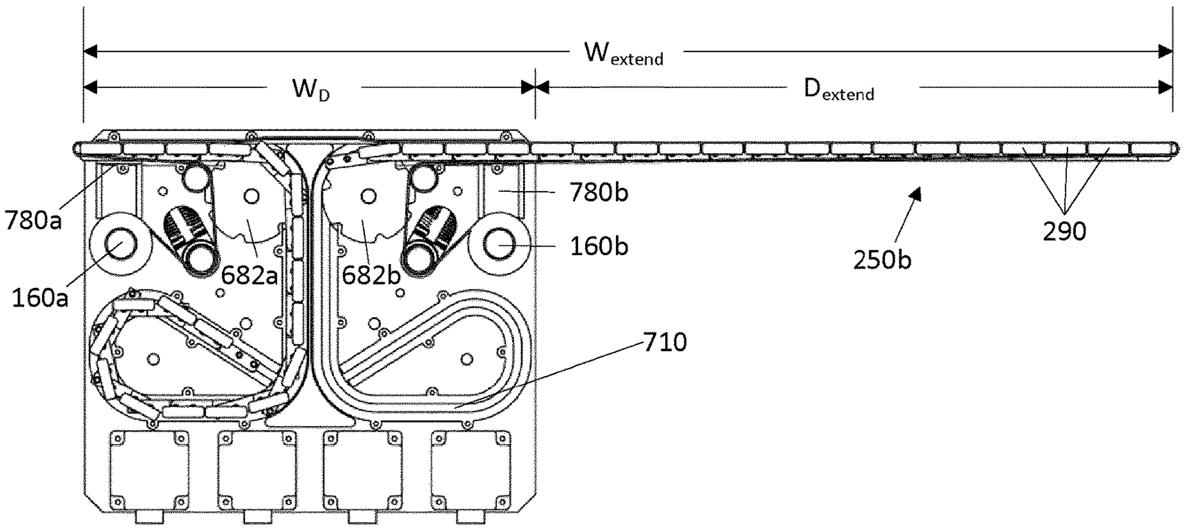
FIG. 53 is a plan section view of the end drive assembly and transfer platforms of FIG. 52.
Figure 54:
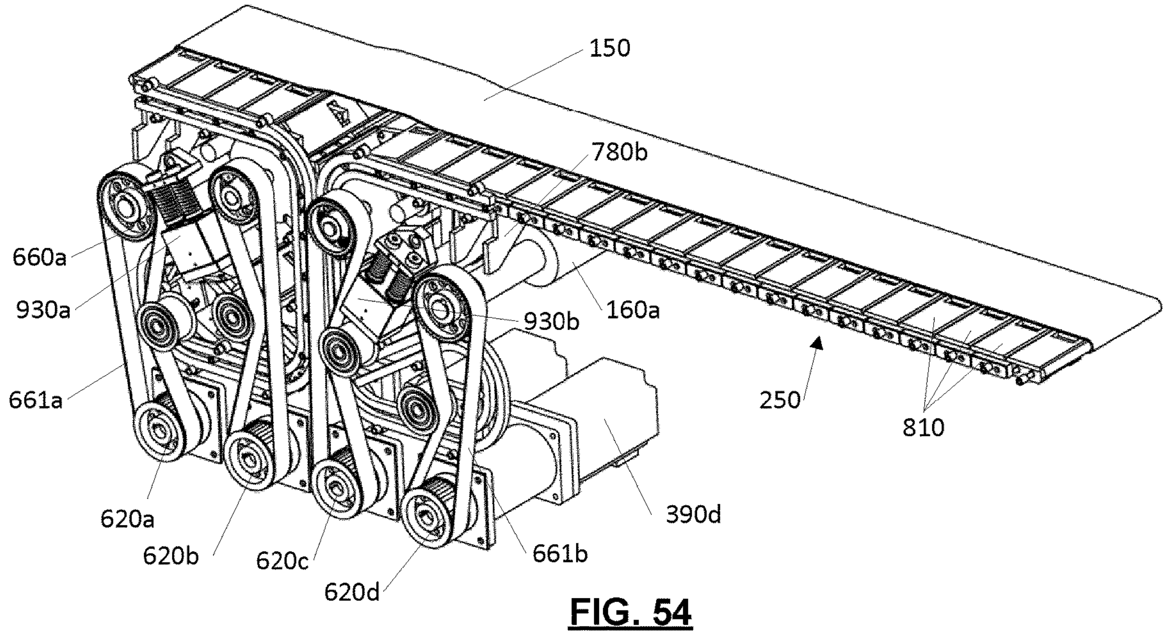
FIG. 54 is another perspective view of the end drive assembly and transfer platforms of FIG. 50, with a base plate of the end drive assembly removed for clarity.
Figure 55:
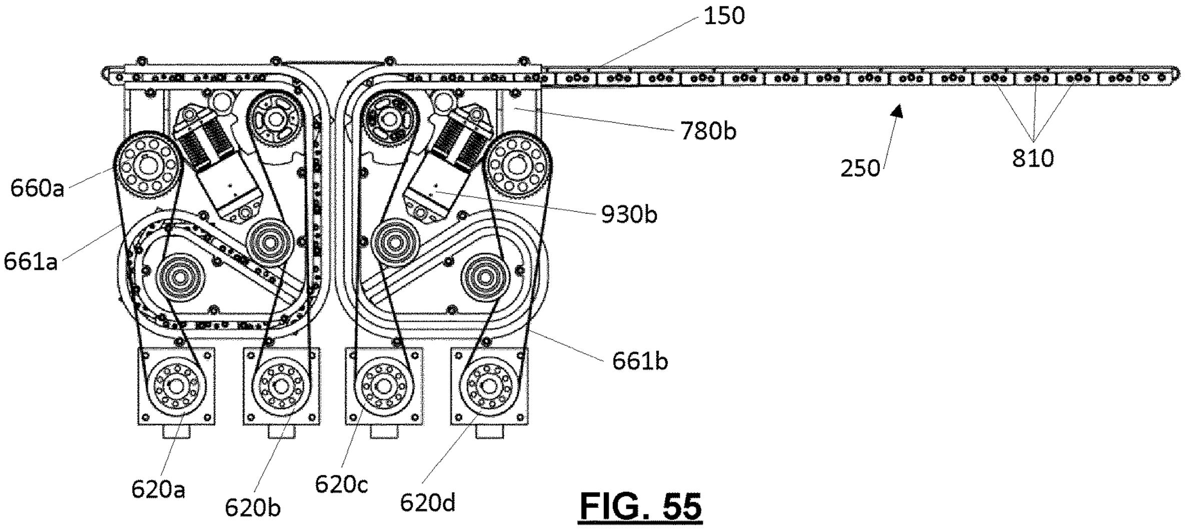
FIG. 55 is a plan end view of the end drive assembly and transfer platform of FIG. 54.
Figure 56:
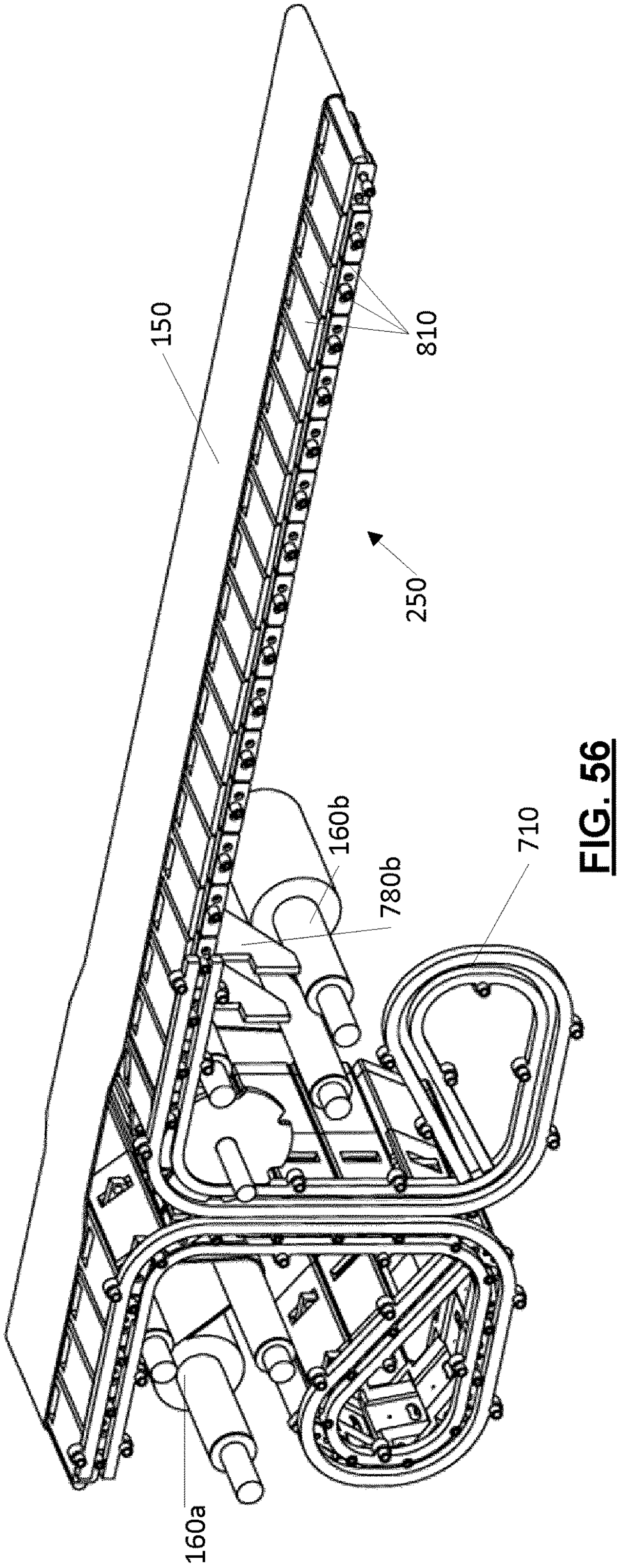
FIG. 56 is a perspective view of the end drive assembly and transfer platforms of FIG. 54, with portions of the end drive assembly removed for clarity.
Figure 57:
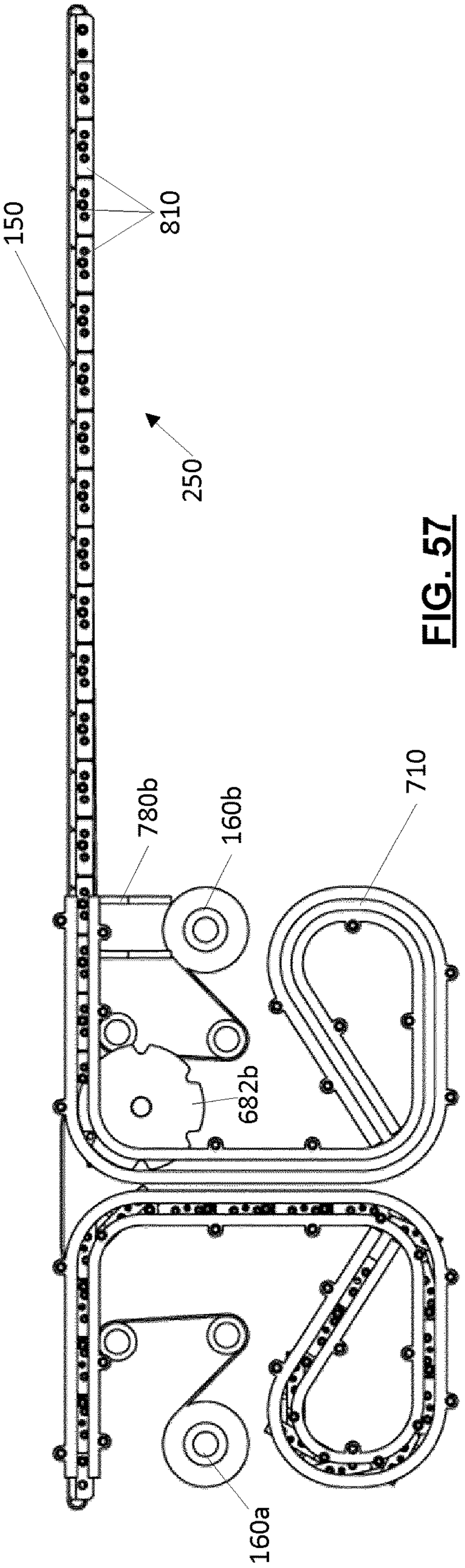
FIG. 57 is an end plan view of the end drive assembly and transfer platforms of FIG. 56.
Figure 58:
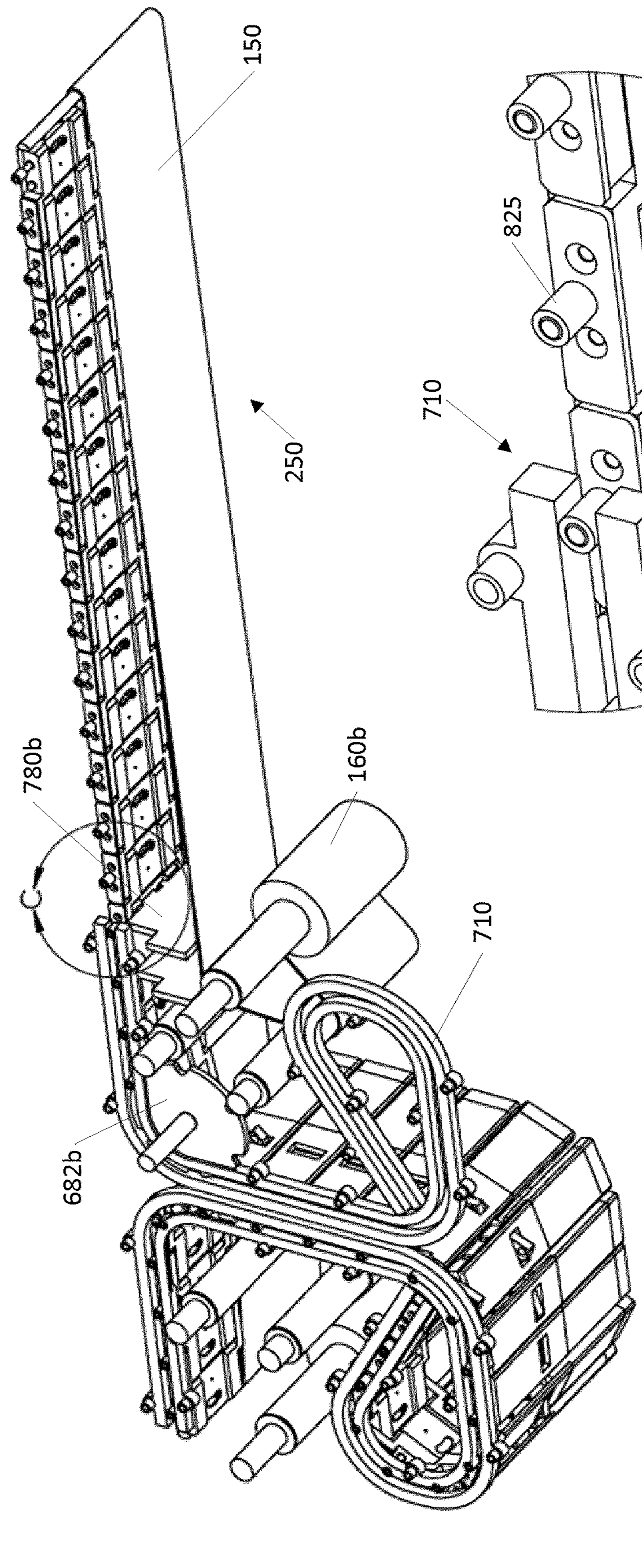
FIG. 58 is another perspective view of the end drive assembly and transfer platform of FIG. 56.

In FIGS. 52 and 53, the second transfer belt 250*b* has been extended outwardly from the second side 114 of the device body 110. Again, the first roller 160*a* and/or the second roller 160*b* may be rotated in order to provide a desired degree of tension along the transfer belt 150.

With reference to FIGS. 62A-C, 63A-C, and 65, in the illustrated example each segment link 810 includes fixed shaft members 820 that extend and project outwardly to engage apertures 880 in an adjacent segment link, providing a pivotable connection between the segment links. In some embodiments, a single shaft member 820 may extend through the segment link 810.

In the illustrated embodiment, an optional bushing or bearing 825 is provided at the end of the outer fixed shaft member 820. The bushing/bearing 825 may assist in guiding platform segments 290 along the internal track 710.

Each segment link 810 also includes movable shaft members 830 that can be selectively extended outwardly in order to engage apertures 870 in adjacent segment link and thereby restrain the segments in an aligned position (e.g. in which the platform segments are generally coplanar).

Figure 65:
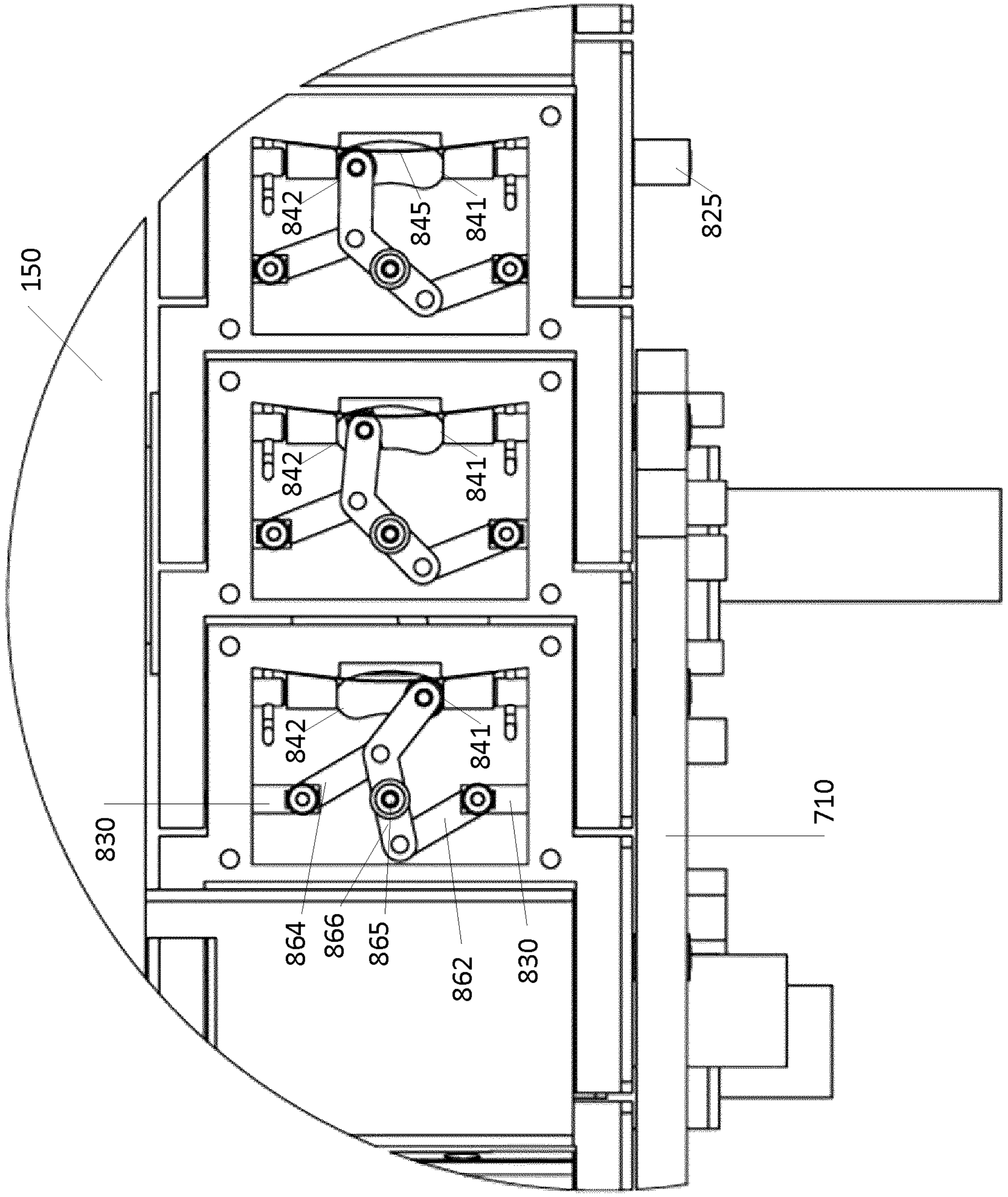
FIG. 65 is an enlarged view of area A in FIG. 64, with portions of the segment links removed for clarity.

In order to move the movable shaft members 830 between an engaged position and an unengaged position, in the illustrated example a pair of end linkage members 862 and 864, and a central linkage member 866 are provided (see e.g. FIG. 65). The central linkage member 866 has a fixed pivot point 865 that allows the linkage member 866 to pivot relative to the segment link 810. Central linkage member 866 is also pivotally connected to both end linkage members 862 and 864. The central linkage member 866 also includes a downwardly facing engagement projection 868.

Figure 62A:
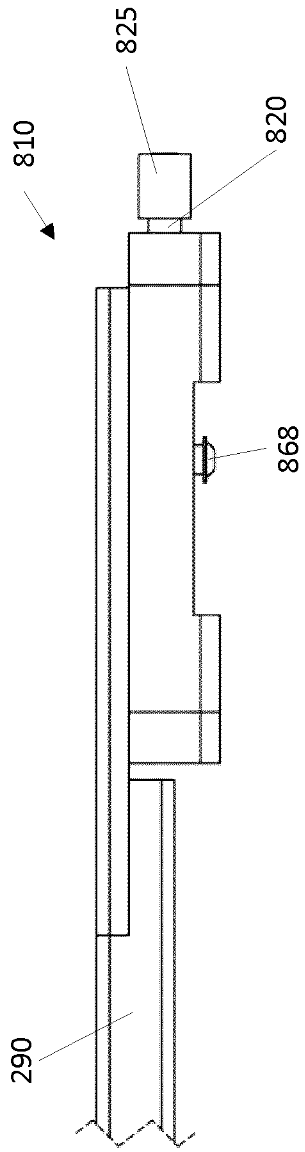
FIG. 62A is a side plan view of segment link of an articulated transfer platform segment, with the segment link in an unlocked configuration.
Figure 62B:
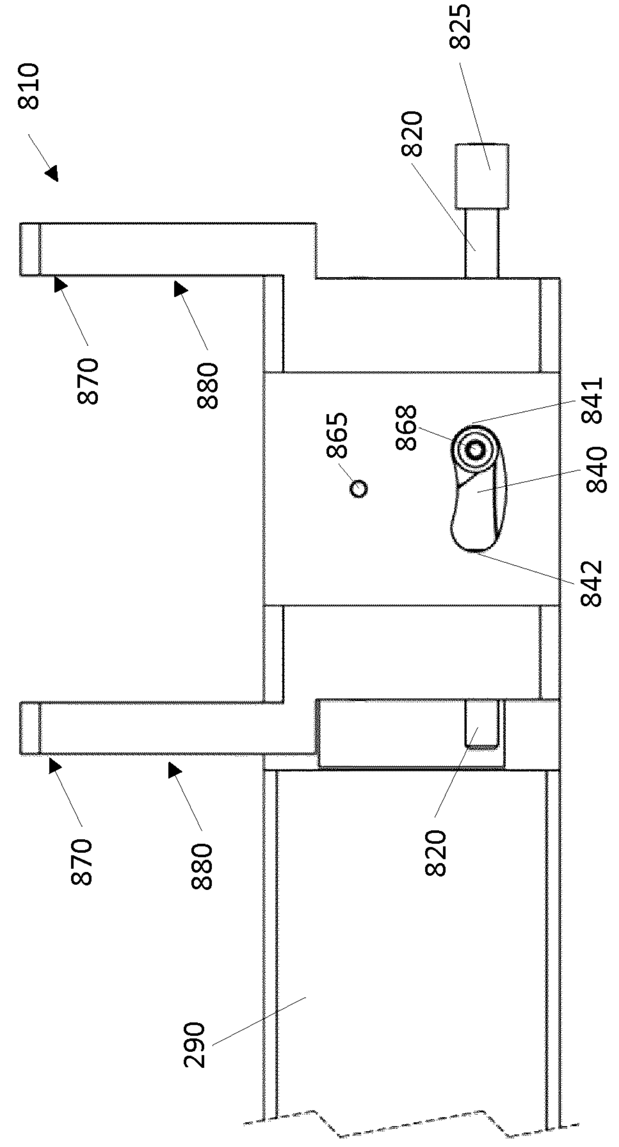
FIG. 62B is a bottom plan view of the segment link of FIG. 62A.
Figure 62C:
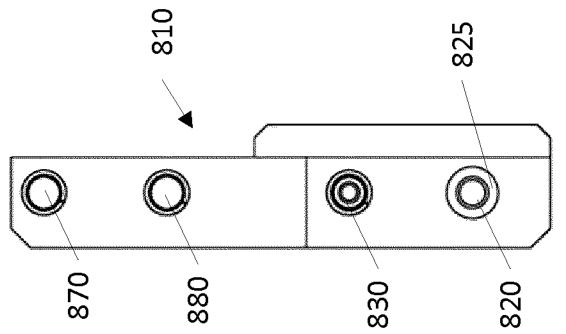
FIG. 62C is an end plan view of the segment link of FIG. 62A.
Figure 63C:
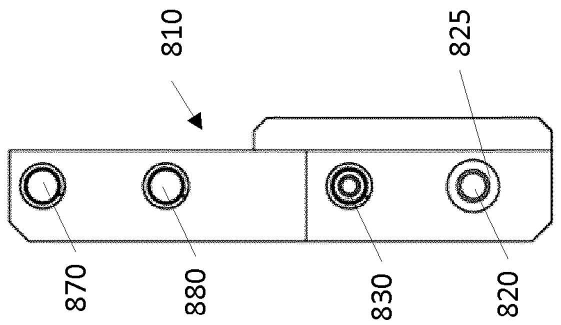
FIG. 63C is an end plan view of the segment link of FIG. 63A.
Figure 63A:
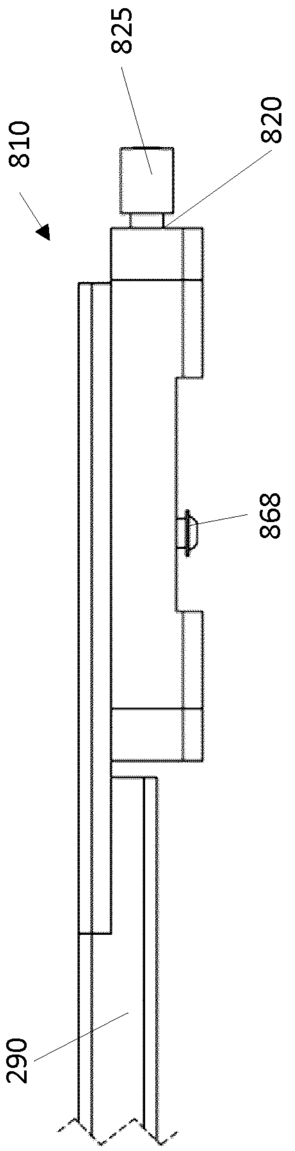
FIG. 63A is a side plan view of a segment link of an articulated transfer platform segment, with the segment link in a locked configuration.
Figure 63B:
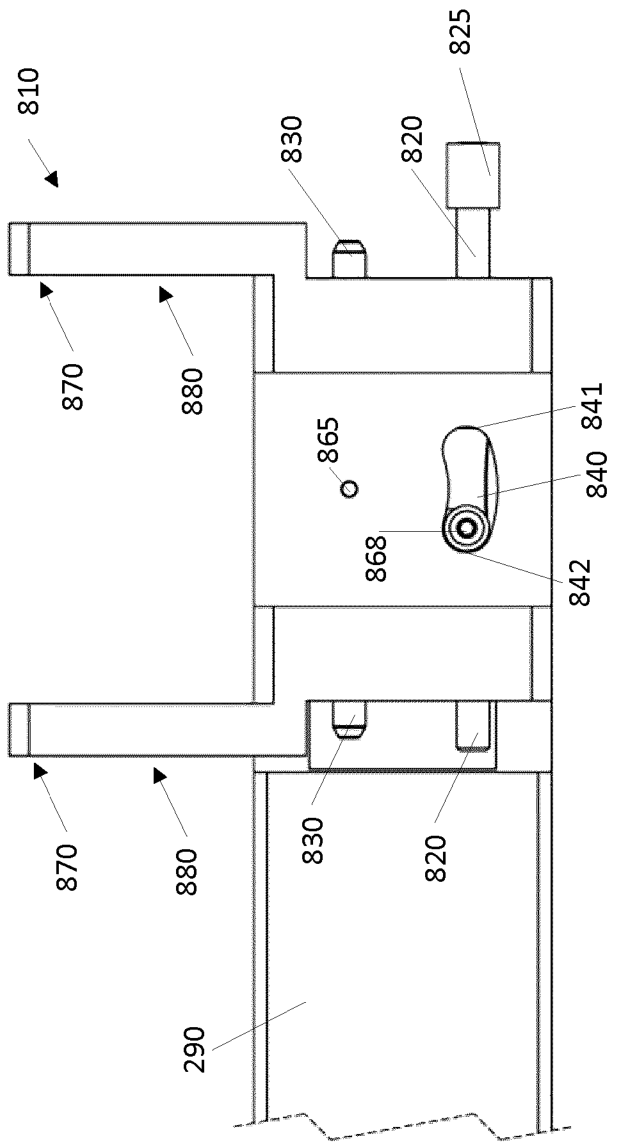
FIG. 63B is a bottom plan view of the segment link of FIG. 63A.
Figure 64:
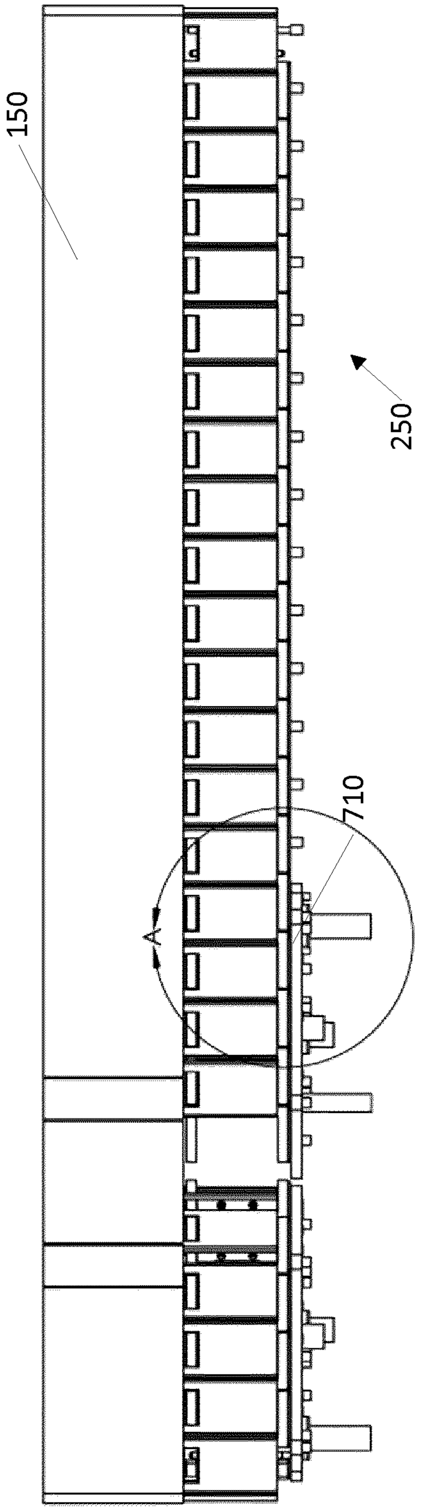
FIG. 64 is a top plan view of the end drive assembly and transfer platforms of FIG. 56.

With reference to FIGS. 62A and 62B, when the central linkage member 866 is in a first position, with the engagement projection 868 at a first end 841 of a curved slot 840, the movable shaft members 830 are in a retracted position. In FIGS. 63A and 63B, the central linkage member is in a second position, with the engagement projection 868 at a second end 842 of the curved slot 840. In this position, the movable shaft members 830 are in an extended position.

Also shown in the illustrated example is an optional biasing member 845, which in this case is an arced piece of resilient material, such as a steel spring, that biases the engagement projection 868 towards either the first end 841 or the second end 842 of the arcuate slot 840.

With reference to FIGS. 58 to 61, in the illustrated example an engagement plate 780 is provided in order to engage or 'lock' adjacent segment links in an aligned position (e.g. in which the platform segments are generally coplanar) as the articulated transfer platform is extended, and to release or 'unlock' adjacent segment links (i.e. to permit the platform segments to pivot relative to each other) as the articulated transfer platform is retracted.

Figure 59:
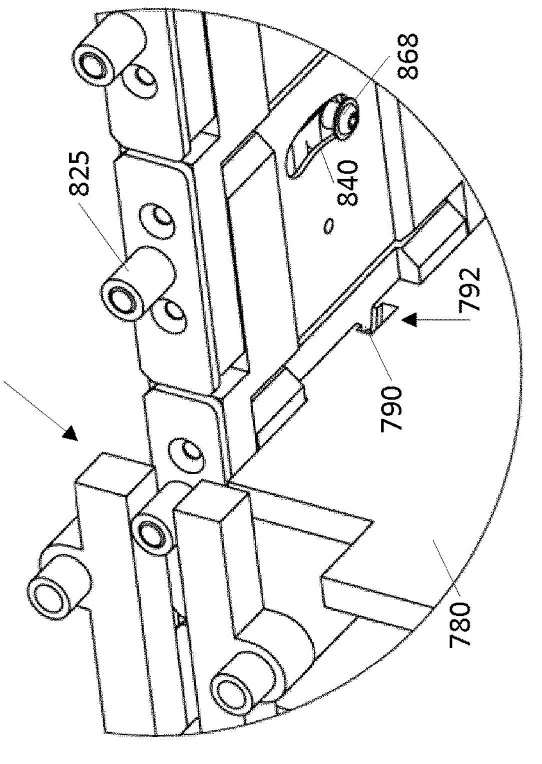
FIG. 59 is an enlarged view of area C in FIG. 58.
Figure 61:
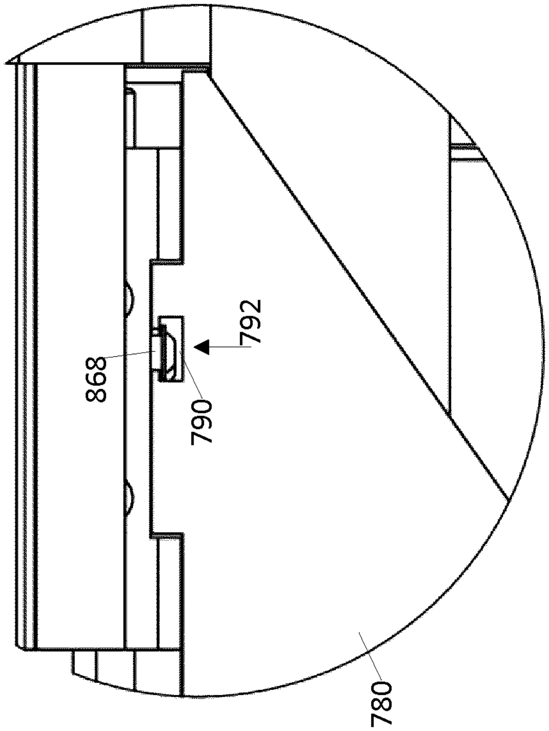
FIG. 61 is an enlarged view of area B in FIG. 60.
Figure 60:
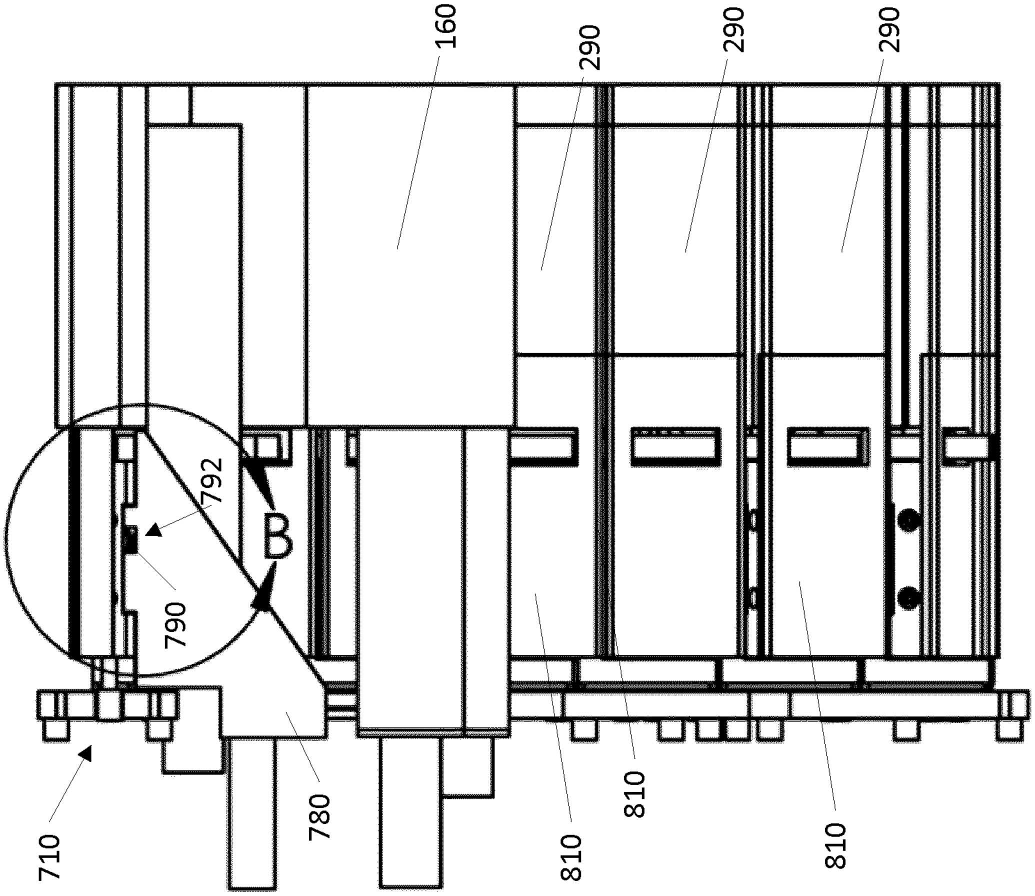
FIG. 60 is a side plan view of the end drive assembly and transfer platforms of FIG. 58.
Figure 66:
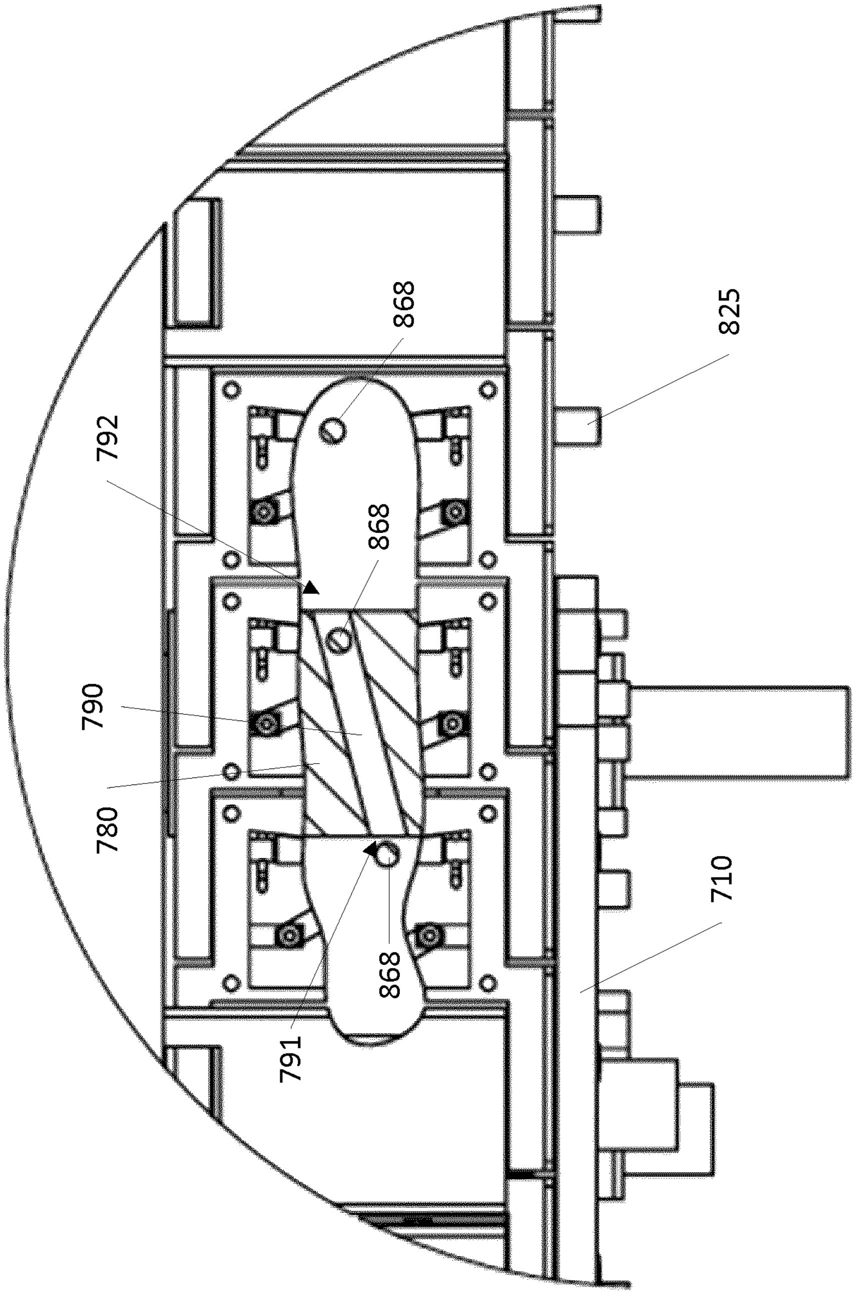
FIG. 66 is another enlarged view of area A in FIG. 64, with additional portions of the segment links cut away for clarity.
Figure 67:
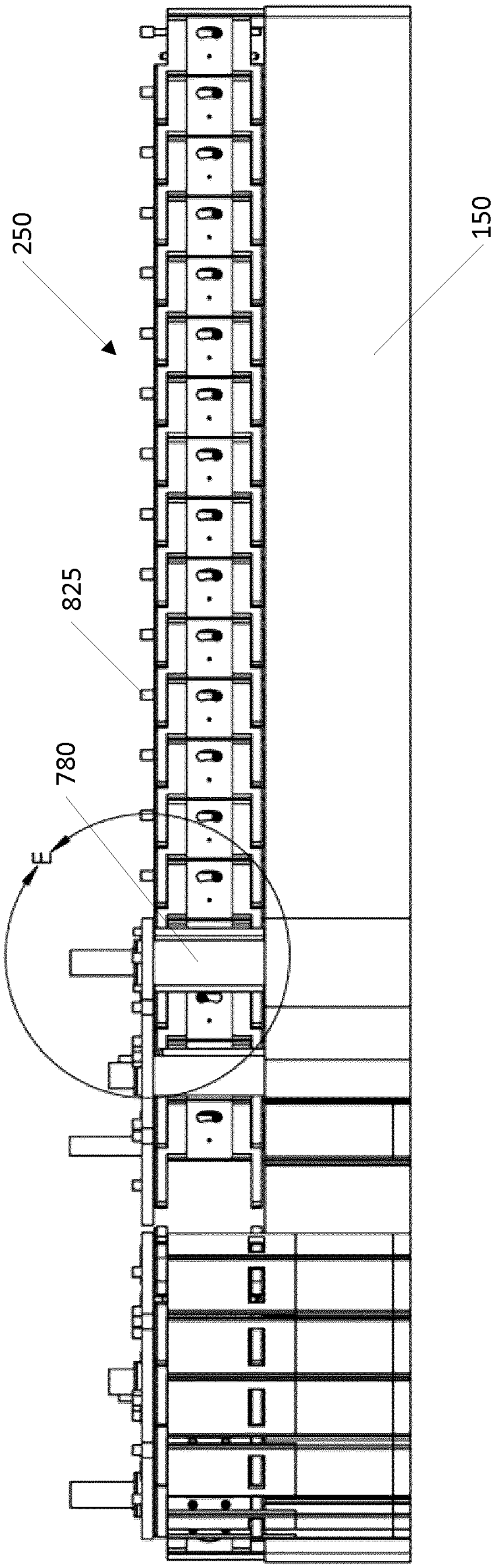
FIG. 67 is a bottom plan view of the end drive assembly and transfer platforms of FIG. 56.
Figure 68:
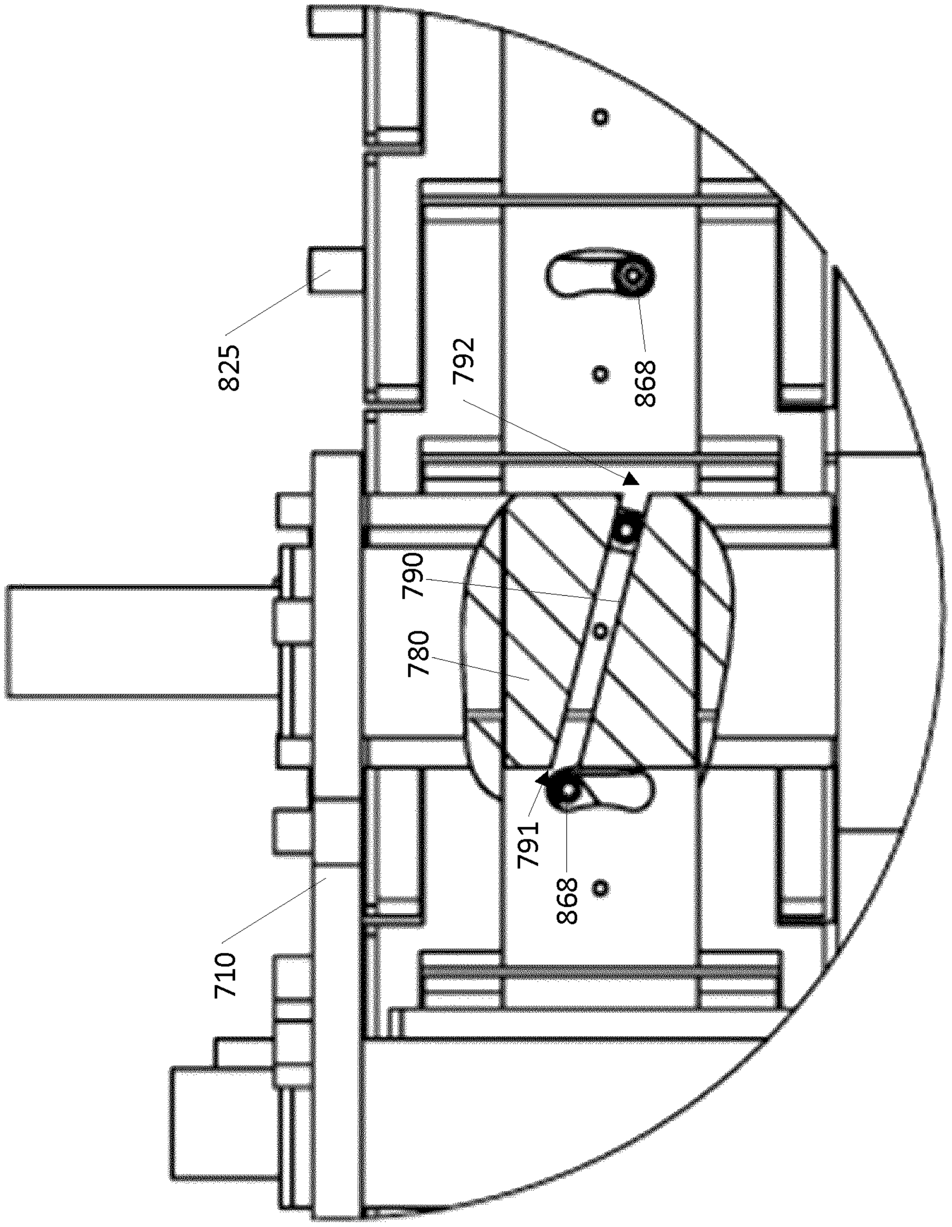
FIG. 68 is an enlarged view of area E in FIG. 67, with portions of an engagement plate shown in section for clarity.
Figure 69:
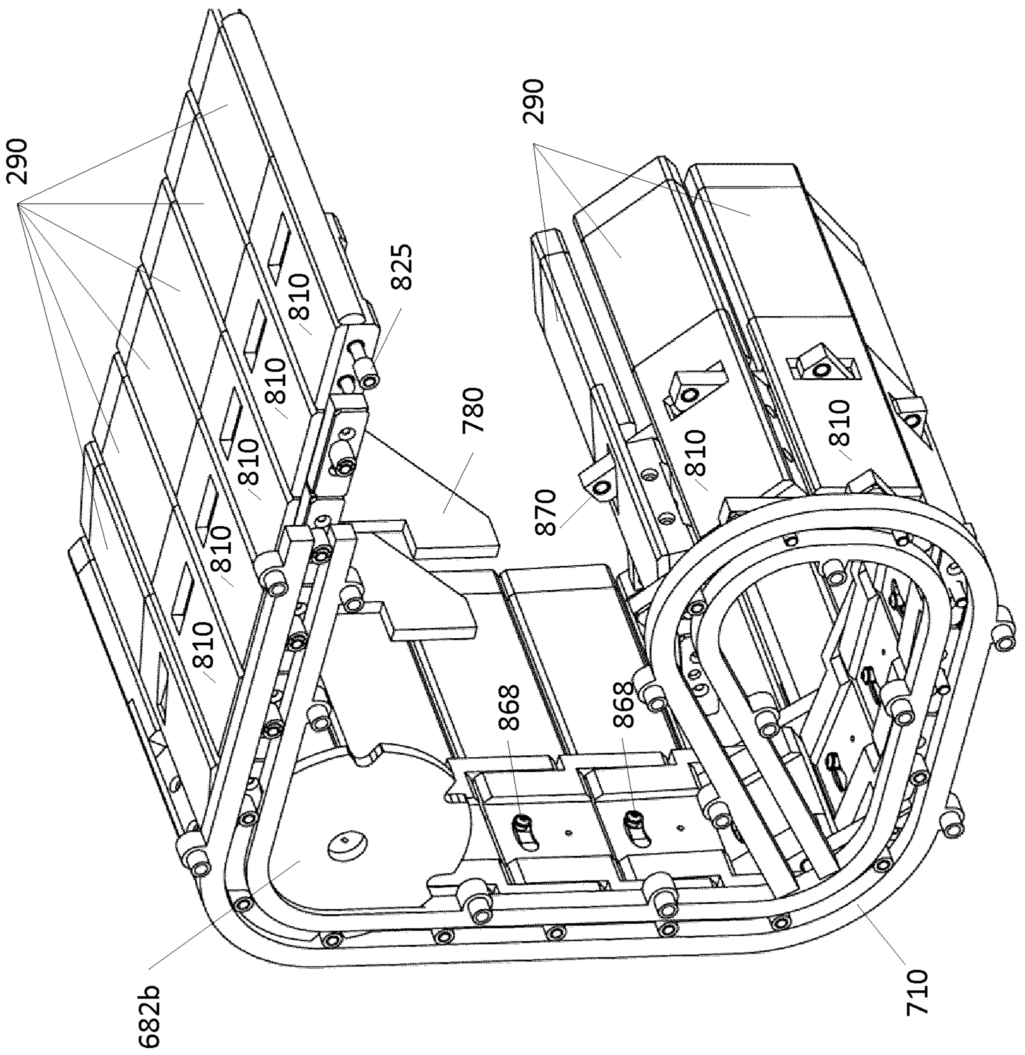
FIG. 69 is a perspective view of a transfer platform, guide track, and drive pinion of the transfer device of FIG. 42.
Figure 70:
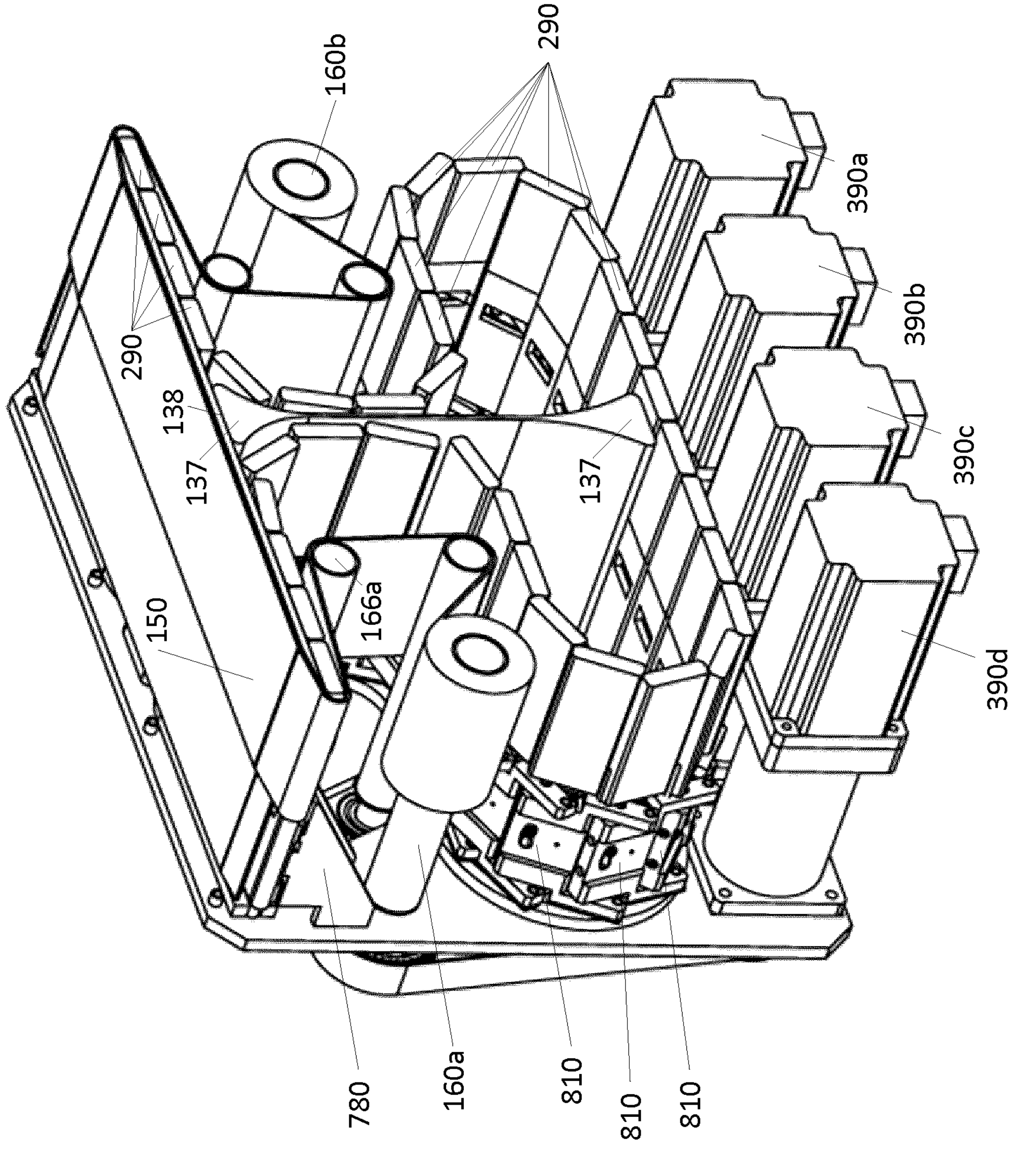
FIG. 70 is a perspective section view of an end drive assembly and transfer platforms of a transfer device in accordance with another embodiment.
Figure 71:
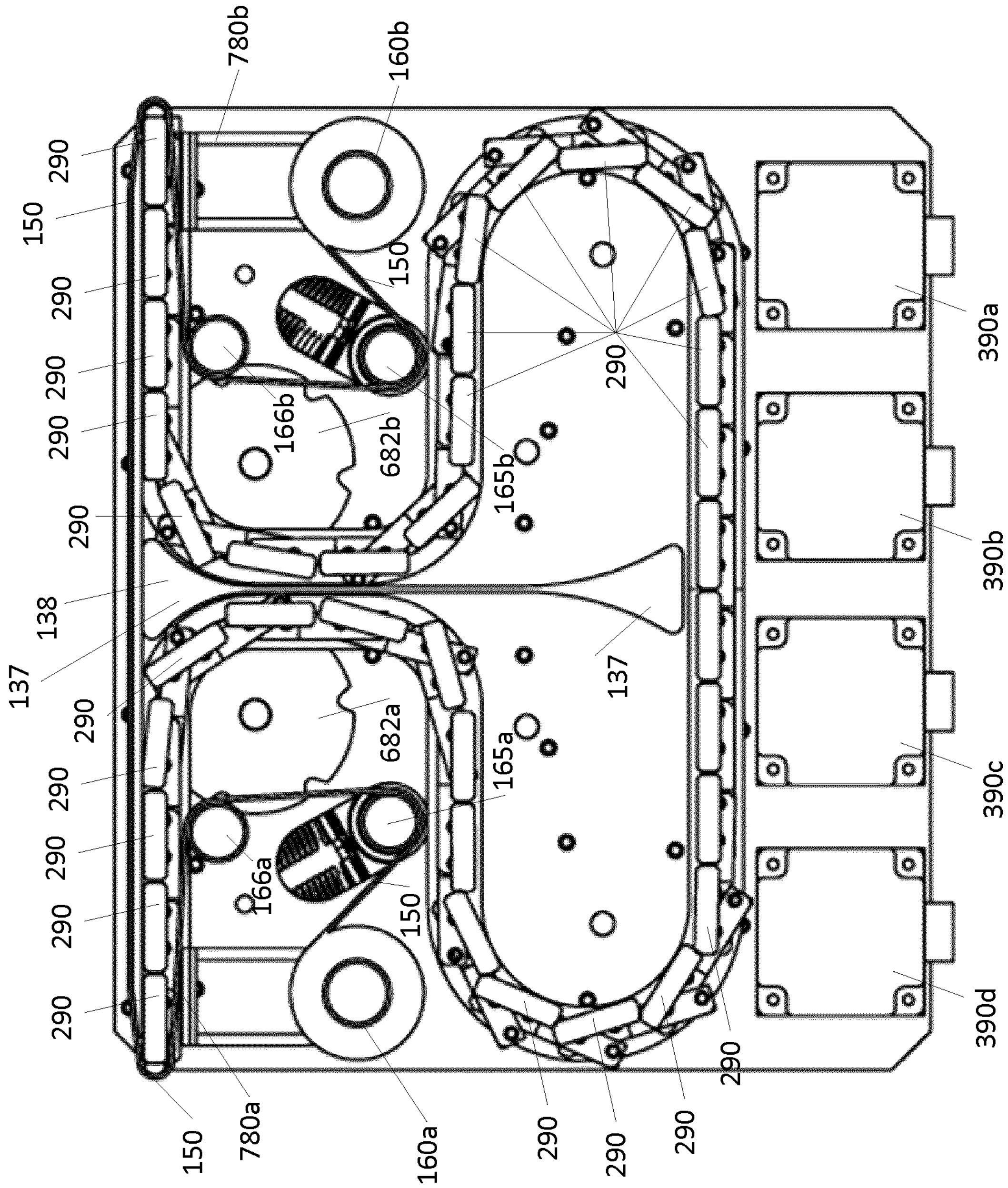
FIG. 71 is a plan section view of the end drive assembly and transfer platforms of FIG. 70.
Figure 72:
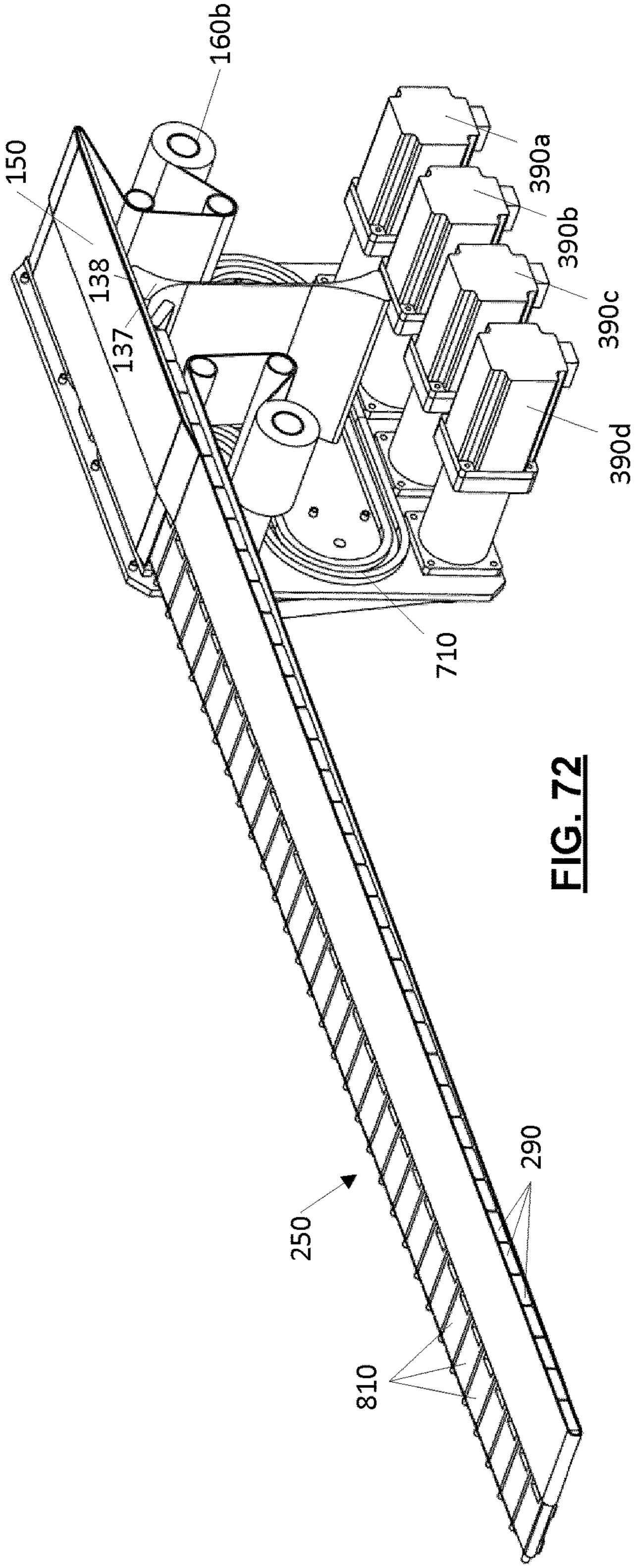
FIG. 72 is a perspective section view of the end drive assembly and transfer platforms of FIG. 70, with the articulated transfer platform in a fully extended position.
Figure 73:
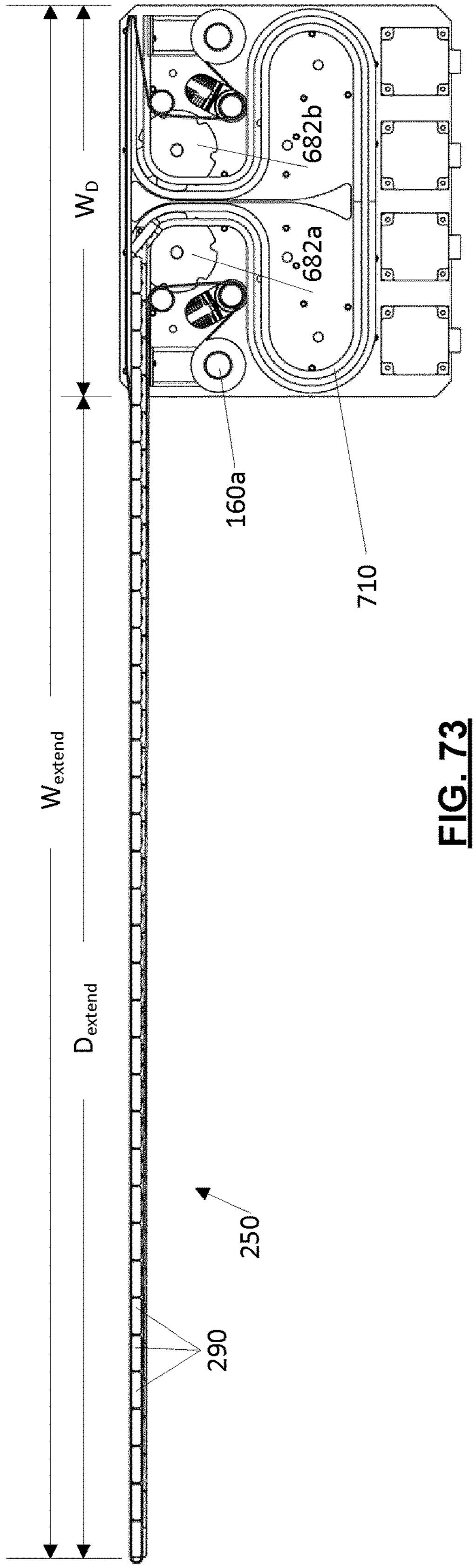
FIG. 73 is a plan section view of the end drive assembly and transfer platforms of FIG. 72.
Figure 74A:
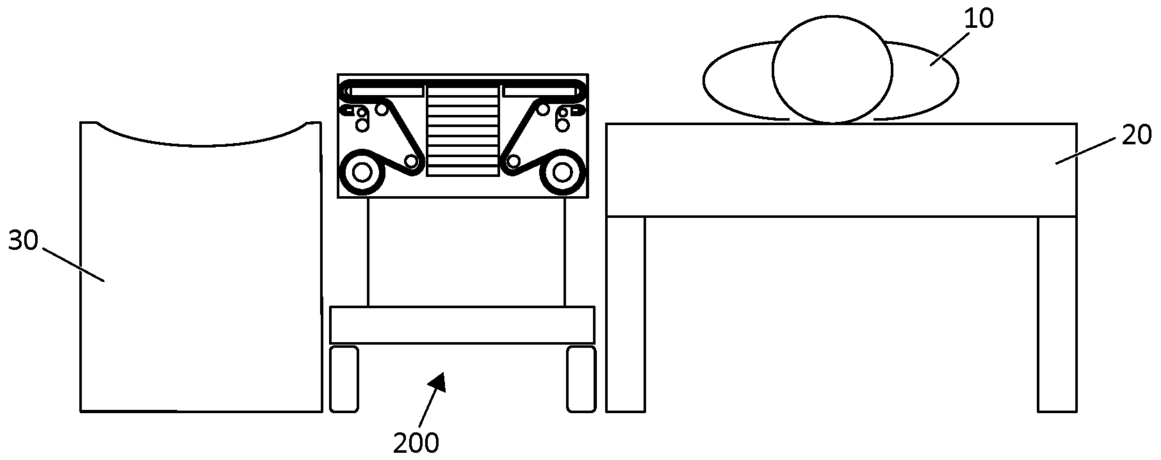
FIGS. 74A-E are a series of schematic elevation views illustrating another extendible transfer platform being used to transfer a human from a gurney onto a bed of a medical imaging scanner.
Figure 74B:
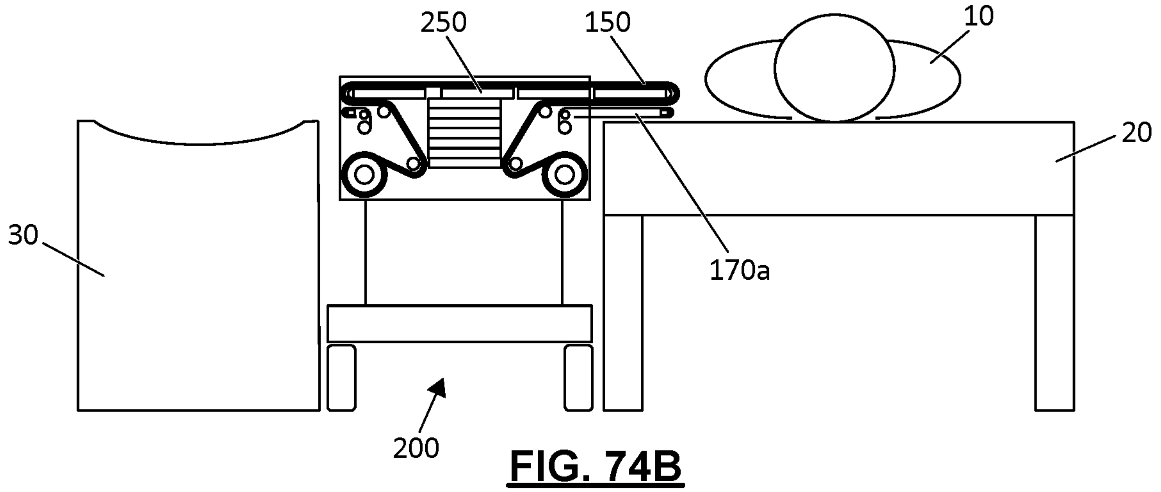
Figure 74C:
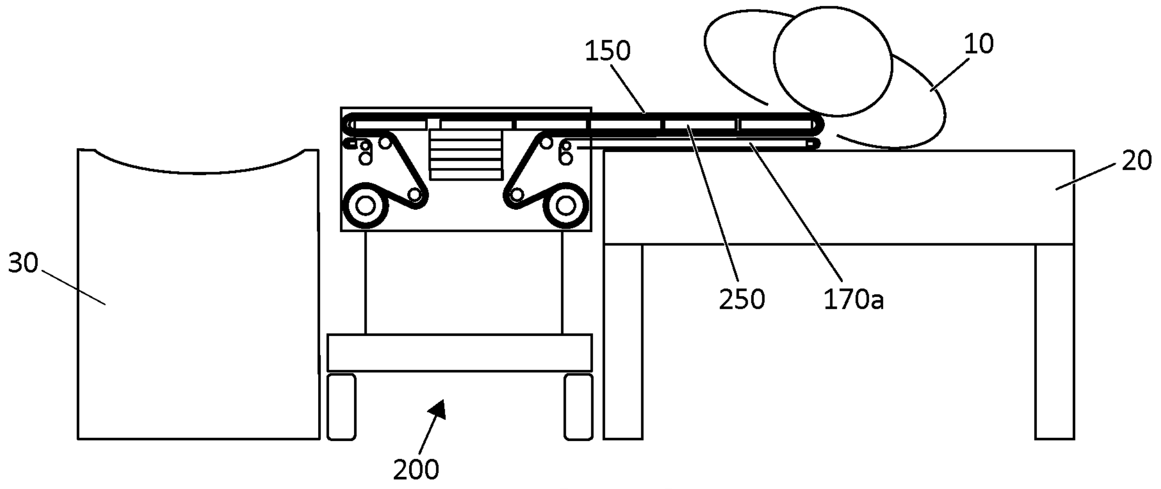
Figure 74D:
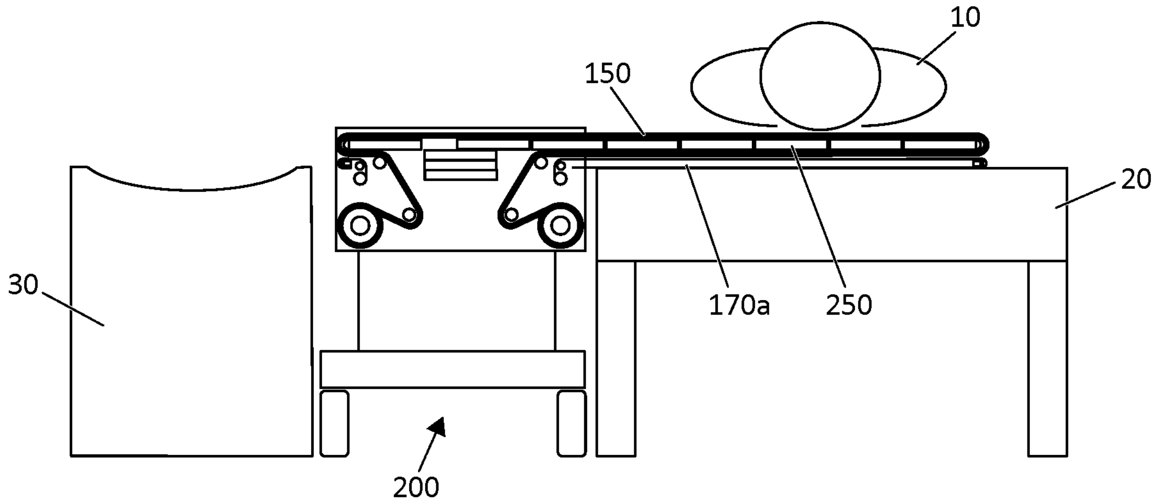
Figure 74E:
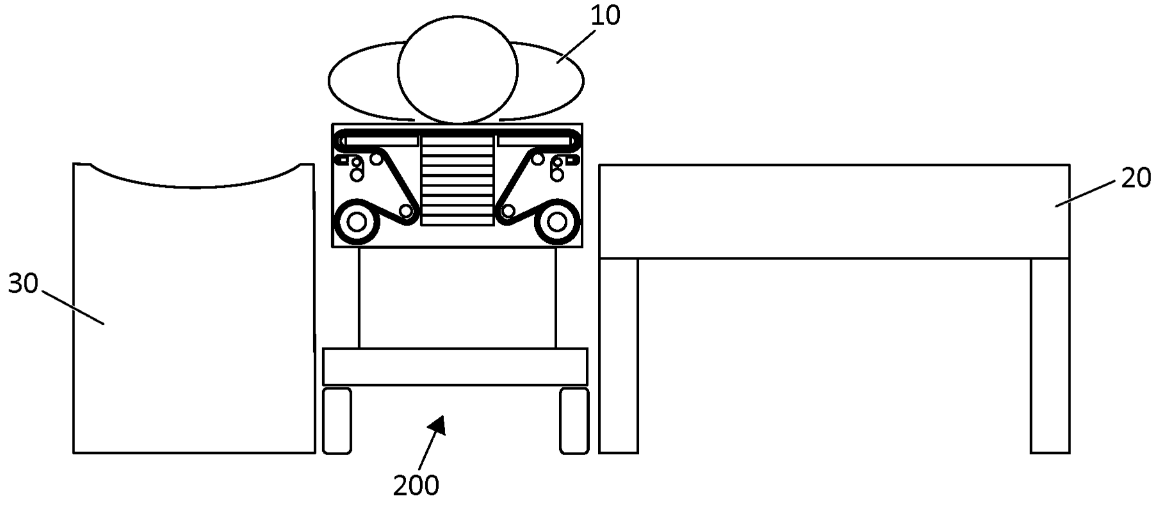

With reference to FIGS. 59, 66, and 68, the engagement plate 780 has a slot 790 that extends at an angle to the path of the segment links as the platform segments are extended and retracted from the transfer device. As a segment link is translated outwardly—e.g. as the articulated transfer platform is being extended—the engagement projection 868 enters a first end 791 of the slot 790. As the segment continues to move outwardly and the engagement projection 868 continues through the slot 790, the engagement projection 868 is urged transversely by the sidewalls of the slot 790 towards the second end 842 of the arcuate slot 840, which results in the shaft members 830 of that segment link to be moved from a retracted position to an extended position, engaging shaft members 830 with apertures 870 of the preceding segment link 810.

As a segment link is translated inwardly—e.g. as the articulated transfer platform is being retracted—the engagement projection 868 enters the second end 792 of the slot 790. As the segment continues to move inwardly, the engagement projection 868 is urged transversely towards the first end 841 of the arcuate slot 840, which results in the shaft members 830 of that segment link to be moved from an extended position to a retracted position, disengaging shaft members 830 from apertures 870 of the trailing segment link, allowing a greater degree of rotation between adjacent transfer platform segments.

In the illustrated example, the engagement plate 780 and its slot 790 may be characterized as a 'passive' actuation system that automatically switches the position of the engagement projection 868 as a segment link 810 passes over the engagement plate 780. In one or more alternative embodiments, the movement of engagement projection 868 may be 'actively' actuated, e.g. via a control system of transfer device 100. For example, the slot 790 may be oriented parallel to the direction of travel of segment links 810, and the engagement plate 780 may be moved perpendicular to the direction of travel to selectively switch the position of the engagement projection 868. Providing 'active' actuation to allow selective locking and unlocking of segment links 810 may have one or more advantages. For example, it may facilitate maintenance operations and/or device testing, and may allow alternative device operations, e.g. extending a transfer platform with one or more segment links in an unrestrained position.

FIGS. 70 to 73 illustrate another example of a transfer device 100 with an articulated transfer platform that includes transfer platform segments that remain coupled to each other.

In this example, a single articulated transfer platform is provided, guided by a continuous internal track 710, that may be extended to either side of the transfer device 100. As can be seen from FIG. 73, the extended distance $D_{extend}$ of articulated transfer platform 250 is much greater than the width $W_D$ of the device body 110. For example, the articulated transfer platform 250 may extends by at least three times the width of the device body 110.

Optionally, the transfer device 100 may include one or more transfer belt treatment systems for applying a cleaning and/or disinfecting treatment to the transfer belt 150. For example, an ultra-violet (UV) light emitter (not shown) may be positioned within the device housing to continuously or selectively emit UV light towards an upper surface of the transfer belt 150, or both an upper surface and a lower surface of the transfer belt 150 as it passes by the emitter. Such a configuration may be characterized as an ultraviolet germicidal irradiation system.

Additionally, or alternatively, a fluid chamber (not shown) may be defined within the housing interior, and a fluid agitator (e.g. an ultrasonic agitator) may be provided to continuously or selectively agitate a fluid as the transfer belt 150 passes through the fluid chamber. Such a configuration may be characterized as a fluid agitation system or as an ultrasonic bath system.

Additionally, or alternatively, a brush, sponge, microfiber, or other material (not shown) may be positioned within the housing and in contact with a surface of the transfer belt 150, such that when the transfer belt is advanced or retracted, dirt or debris may be removed from an upper surface of the transfer belt 150, or both an upper surface and a lower surface of the transfer belt 150. Optionally, a reservoir of a cleaning and/or disinfectant fluid (e.g. alcohol, peroxide, bleach, etc.) may also be provided, for dispensing cleaning and/or disinfectant fluid onto the brush, sponge, microfiber, or other material, and/or directly onto the transfer belt 150.

It will be appreciated that for embodiments that include a fluid dispensing apparatus, 'fluid-proofing' or at least increased ingress protection may be required for fluid-sensitive parts of the device (e.g. electronics).

In some embodiments, a manual actuator (e.g. a depressible button) may be provided to selectively actuate the transfer belt treatment system to provide one or more treatment agents (e.g. UV light, disinfectant fluid, ultrasonic bath agitation) to the transfer belt 150. For example, the UV light emitter may be configured such that, in response to depression of the manual actuator, it emits UV light for a pre-set period of time (e.g. 10 seconds, 30 minutes), which may be selected based on e.g. the decontamination level required, a distance of the emitter from belt 150, the intensity of light emitted by the emitter, and/or other factors known to those in the art. As another example, the agitator may be configured such that, in response to depression of the manual actuator, it agitates fluid in the chamber for a pre-set period of time (e.g. 10 seconds, 30 minutes), which may be selected based on e.g. the decontamination level required, composition of fluid within the chamber, and/or other factors known to those in the art. Additionally, or alternatively, the transfer belt treatment system may be configured such that one or more treatment agents (e.g. UV light, disinfectant fluid, ultrasonic agitation) are provided at pre-set intervals (e.g. following every transfer operation, every 24 hours) without requiring manual actuation, and/or at a preset time after a transfer operation has been performed.

In some embodiments, there is provided a platform segment treatment system. Similar to the transfer belt treatment system, the platform segment treatment system can include an Ultraviolet (UV) light emitter configured to direct UV light towards at least an upper surface of the one or more successive intermediate platform segments, a fluid emitter configured to direct at least one of a cleaning fluid and a disinfectant fluid towards at least the upper surface of the one or more successive intermediate platform segments, and/or a fluid agitator configured to agitate fluid in a fluid chamber through which the one or more successive intermediate platform segments are configured to pass. In some embodiments, the transfer device controller is operatively coupled to the platform segment treatment system, and the transfer device controller is configured to selectively actuate one or more of the UV light emitter, the fluid emitter, and the fluid agitator concurrently or separately from each other.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term, such as by 1%, 2%, 5% or 10%, for example, if this deviation does not negate the meaning of the term it modifies.

While the above description describes features of example embodiments, it will be appreciated that some features and/or functions of the described embodiments are susceptible to modification without departing from the spirit and principles of operation of the described embodiments. For example, the various characteristics which are described by means of the represented embodiments or examples may be selectively combined with each other. Accordingly, what has been described above is intended to be illustrative of the claimed concept and non-limiting. It will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

We claim:

1. A transfer device comprising:
- a device body having a first end, a second end, a first side, and a second side; and an articulated transfer platform comprising:
- a distal platform segment having a first end, a second end, a leading edge extending between the first end and the second end, a trailing edge extending between the first end and the second end, and a distal locking mechanism;
- a plurality of intermediate platform segments, including a lead intermediate platform segment and one or more successive intermediate platform segments, each intermediate platform segment having a first end, a second end, a first edge extending between the first end and the second end, a second edge extending between the first end and the second end, and an intermediate locking mechanism;
- wherein the distal locking mechanism is releasably securable to the intermediate locking mechanism of the lead intermediate platform segment, and
- wherein the intermediate locking mechanism of each successive intermediate platform segment is releasably securable to the intermediate locking mechanism of a preceding intermediate platform segment; and
- wherein, in a stowed position, the one or more successive intermediate platform segments are positioned below the lead intermediate platform segment, and
- wherein, in an extended position, the distal platform segment is located laterally away from the device body, the distal locking mechanism is secured to the intermediate locking mechanism of the lead intermediate platform segment, and the intermediate locking mechanism of one of the successive intermediate platform segments is secured to the intermediate locking mechanism of the lead intermediate platform segment.

2. The transfer device of claim 1, wherein the distal locking mechanism is located proximate the first end of the distal platform segment, and for each intermediate platform segment, the intermediate locking mechanism is located proximate the first end of the intermediate platform segment.

3. The transfer device of claim 1, further comprising a transfer device controller configured to control the articulated transfer platform.

4. The transfer device of claim 3, further comprising a platform lateral actuator operably coupled to the transfer device controller, the platform lateral actuator being configured to selectively move the distal platform segment and intermediate platform segments secured thereto laterally relative to the device body.

5. The transfer device of claim 3, further comprising a platform segment support assembly operably coupled to the transfer device controller, the platform segment support assembly being configured to selectively raise the one or more successive intermediate platform segments to bring the intermediate locking mechanism of a raised successive intermediate platform segment into alignment with the intermediate locking mechanism of a preceding intermediate platform segment.

6. The transfer device of claim 5, further comprising a platform segment release actuator operably coupled to the transfer device controller, the platform segment release actuator being configured to selectively disengage the locking mechanisms of successive platform segments.

7. The transfer device of claim 1, wherein, in the stowed position, the distal platform segment at least partially overlies the device body.

8. The transfer device of claim 1, wherein, in the stowed position, the distal platform segment is secured to the lead intermediate platform segment.

9. The transfer device of claim 1, wherein, in the stowed position, the successive intermediate platform segments are vertically stacked below the lead intermediate platform segment.

10. The transfer device of claim 1, wherein, when the distal platform segment and the intermediate platform segments of the articulated transfer platform are secured to each other to produce secured segments, the secured segments may be pivoted relative to each other by about 1° to 30°, or by about 10° to 20°, or by about 15°.

11. The transfer device of claim 10, wherein, when the distal platform segment and the intermediate platform segments of the articulated transfer platform are secured to each other to produce the secured segments, the secured segments are biased towards a neutral alignment in which adjacent segments are generally planar.

12. The transfer device of claim 11, wherein, when the distal platform segment and the intermediate platform segments of the articulated transfer platform are secured to each other to produce the secured segments, a magnitude of the bias towards the neutral alignment is selectively adjustable.

13. The transfer device of claim 1, wherein the device body has a width between the first and second sides of the device body, and wherein, in the extended position, a distance between the leading edge of the distal platform segment and the first side of the device body is greater than the width of the device body.

14. The transfer device of claim 13, wherein the width of the device body is about 400 mm to 1000 mm, and wherein, in the extended position, the distance between the leading edge of the distal platform segment and the first side of the device body is about 600 mm to 1400 mm.

15. The transfer device of claim 1, wherein the distal locking mechanism comprises one or more recesses.

16. The transfer device of claim 1, wherein the distal locking mechanism comprises one or more projections.

17. The transfer device of claim 1, wherein the intermediate locking mechanisms comprise one or more projections and one or more recesses.

18. The transfer device of claim 3, further comprising a transfer belt having a first end secured to a first driven roller, a second end secured to a second driven roller, the belt extending from the first driven roller, around the leading edge of the distal platform segment, above an upper surface of the articulated transfer platform, and to the second driven roller, wherein the first driven roller and the second driven roller are operably coupled to the transfer device controller.

19. The transfer device of claim 18, wherein the transfer belt is a first transfer belt and the transfer device further comprises a second transfer belt extending below a bottom surface of the articulated transfer platform on the first side of the device body, and a third transfer belt extending below a bottom surface of the articulated transfer platform on the second side of the device body.

20. The transfer device of claim 18, further comprising a belt treatment system comprising at least one of:

an Ultraviolet (UV) light emitter configured to direct UV light towards at least an upper surface of the transfer belt;

a fluid emitter configured to direct at least one of a cleaning fluid and a disinfectant fluid towards at least the upper surface of the transfer belt; and a fluid agitator configured to agitate fluid in a fluid chamber through which the transfer belt is configured to pass.

21. The transfer device of claim 20, wherein the transfer device controller is operatively coupled to the belt treatment system, and wherein the transfer device controller is configured to selectively actuate one or more of the UV light emitter, the fluid emitter, and the fluid agitator concurrently or separately from each other.

22. The transfer device of claim 3, further comprising a platform segment treatment system comprising at least one of:

an Ultraviolet (UV) light emitter configured to direct UV light towards at least an upper surface of the one or more successive intermediate platform segments;

a fluid emitter configured to direct at least one of a cleaning fluid and a disinfectant fluid towards at least the upper surface of the one or more successive intermediate platform segments; and a fluid agitator configured to agitate fluid in a fluid chamber through which the one or more successive intermediate platform segments are configured to pass.

23. The transfer device of claim 22, wherein the transfer device controller is operatively coupled to the platform segment treatment system, and wherein the transfer device controller is configured to selectively actuate one or more of the UV light emitter, the fluid emitter, and the fluid agitator concurrently or separately from each other.

24. The transfer device of claim 1, further comprising a device support structure secured to the device body for supporting the device body above a floor surface, wherein the device support structure is configurable to adjust a height of the device body above the floor surface and/or an angle of the device body.

25. The transfer device of claim 24, wherein the device support structure comprises a plurality of wheels to facilitate translation of the transfer device across the floor surface.

26. The transfer device of claim 25, wherein at least one of the plurality of wheels is driven by a motor, such that the transfer device is able to transport itself across the floor surface.

27. The transfer device of claim 3, wherein the transfer device comprises a plurality of controllable subsystems, and wherein the transfer device controller comprises a plurality of controllers configured to control the articulated transfer platform and all of the controllable subsystems.

28. The transfer device of claim 3, wherein the transfer device comprises a plurality of controllable subsystems, and wherein the transfer device controller comprises a single controller configured to control the articulated transfer platform and all of the controllable subsystems.

29. A transfer device comprising:

a device body having a first end, a second end, a first side, and a second side; and an articulated transfer platform comprising:

a distal platform segment, and a plurality of intermediate platform segments, each platform segment having a first end, a second end, and a segment link positioned at each of the first and second ends, the distal platform segment having a leading edge;

wherein the segment links of adjacent platform segments are pivotally coupled to each other, wherein the segment links of adjacent platform segments are configured to be selectively restrained in an aligned position;

wherein, in a stowed position, the platform segments of the articulated transfer platform are engaged with an internal track of the device body, wherein, as the articulated transfer platform is extended from the stowed position, the distal platform segment is extended laterally away from the device body and the segment links of successive platform segments are restrained in the aligned position upon exiting the internal track, and wherein, as the articulated transfer platform is retracted, the segment links of successive platform segments are unrestrained from the aligned position upon entering the internal track.

30. The transfer device of claim 29, further comprising a transfer device controller configured to control the articulated transfer platform.

31. The transfer device of claim 29, wherein the articulated transfer platform is a first articulated transfer platform, the distal platform segment is a first distal platform segment, the intermediate platform segments are first intermediate platform segments, the internal track is a first internal track, and the transfer device further comprises:

a second articulated transfer platform comprising:

a second distal platform segment, and a plurality of second intermediate platform segments, each second platform segment having a first end, a second end, and a segment link positioned at each of the first and second ends, the second distal platform segment having a leading edge;

wherein the segment links of adjacent second platform segments are pivotally coupled to each other, and wherein the segment links of adjacent second platform segments are configured to be selectively restrained in an aligned position;

wherein, in a stowed position, the platform segments of the second articulated transfer platform are engaged with a second internal track of the device body, wherein, as the second articulated transfer platform is extended from the stowed position, the second distal platform segment is extended laterally away from the device body and the segment links of successive second platform segments are restrained in the aligned position upon exiting the second internal track, and wherein, as the second articulated transfer platform is retracted, the segment links of successive second platform segments are unrestrained from the aligned position upon entering the second internal track.

32. The transfer device of claim 30, further comprising a transfer belt having a first end secured to a first driven roller, a second end secured to a second driven roller, the belt extending from the first driven roller, around the leading edge of the first distal platform segment, above an upper surface of the articulated transfer platform, and to the second driven roller, wherein the first driven roller and the second driven roller are operably coupled to the transfer device controller.

33. The transfer device of claim 32, wherein the transfer belt is a first transfer belt and the transfer device further comprises a second transfer belt extending below a bottom surface of the articulated transfer platform on the first side of the device body, and a third transfer belt extending below a bottom surface of the articulated transfer platform on the second side of the device body.

34. The transfer device of claim 29, further comprising an engagement plate positioned proximate an end of the internal track, the engagement plate being configured to restrain adjacent segment links as they pass the engagement plate as the articulated transfer platform is extended, and configured to unrestrain adjacent segment links as they pass the engagement plate as the articulated transfer platform is retracted.

35. The transfer device of claim 29, further comprising a first engagement plate positioned proximate a first end of the internal track, and a second engagement plate positioned proximate a second end of the internal track, the first and second engagement plates being configured to restrain adjacent segment links as they exit the internal track, and to unrestrain adjacent segment links they enter the internal track.

36. The transfer device of claim 29, wherein the device body has a width between the first and second sides of the device body, and wherein, when the articulated transfer platform is fully extended from the first side of the device body, a distance between the leading edge of the first distal platform segment and the first side of the device body is greater than the width of the device body.

37. The transfer device of claim 29, further comprising:

a belt treatment system comprising at least one of:

an Ultraviolet (UV) light emitter configured to direct UV light towards at least an upper surface of the transfer belt;

a fluid emitter configured to direct at least one of a cleaning fluid and a disinfectant fluid towards at least the upper surface of the transfer belt; and a fluid agitator configured to agitate fluid in a fluid chamber through which the transfer belt is configured to pass.

38. The transfer device of claim 37, wherein the transfer device controller is operatively coupled to the belt treatment system, and wherein the transfer device controller is configured to selectively actuate one or more of the UV light emitter, the fluid emitter, and the fluid agitator concurrently or separately from each other.

39. The transfer device of claim 29, further comprising:

a platform segment treatment system comprising at least one of:

an Ultraviolet (UV) light emitter configured to direct UV light towards at least an upper surface of the one or more successive intermediate platform segments;

a fluid emitter configured to direct at least one of a cleaning fluid and a disinfectant fluid towards at least the upper surface of the one or more successive intermediate platform segments; and a fluid agitator configured to agitate fluid in a fluid chamber through which the one or more successive intermediate platform segments are configured to pass.

40. The transfer device of claim 39, wherein the transfer device controller is operatively coupled to the platform segment treatment system, and wherein the transfer device controller is configured to selectively actuate one or more of the UV light emitter, the fluid emitter, and the fluid agitator concurrently or separately from each other.

41. The transfer device of claim 29, further comprising a device support structure secured to the device body for supporting the device body above a floor surface, wherein the device support structure is configurable to adjust a height of the device body above the floor surface and/or an angle of the device body.

42. The transfer device of claim 41, wherein the device support structure comprises a plurality of wheels to facilitate translation of the transfer device across the floor surface.

43. The transfer device of claim 42, wherein at least one of the plurality of wheels is driven by a motor, such that the transfer device is able to transport itself across the floor surface.

44. The transfer device of claim 30, wherein the transfer device comprises a plurality of controllable subsystems, and wherein the transfer device controller comprises a plurality of controllers configured to control the articulated transfer platform and all of the controllable subsystems.

45. The transfer device of claim 30, wherein the transfer device comprises a plurality of controllable subsystems, and wherein the transfer device controller comprises a single controller configured to control the articulated transfer platform and all of the controllable subsystems.

46. A transfer device comprising:

a device body having a first side and a second side; and an articulated transfer platform comprising:

a first distal platform segment, a plurality of intermediate platform segments, and a second distal platform segment, each platform segment having a first end, a second end, and a segment link positioned at each of the first and second ends, and each distal platform segment having a leading edge;

wherein the segment links of adjacent platform segments are pivotally coupled to each other, and are configured to be selectively restrained in an aligned position;

wherein, in a stowed position, the platform segments of the articulated transfer platform are engaged with an internal track of the device body;

wherein, as the articulated transfer platform is extended from the first side of the device body, the first distal platform segment is extended laterally away from the device body and the segment links of successive intermediate platform segments are restrained in the aligned position upon exiting the internal track;

wherein, as the articulated transfer platform is extended from the second side of the device body, the second distal platform segment is extended laterally away from the device body and the segment links of successive intermediate platform segments are restrained in the aligned position upon exiting the internal track; and wherein, as intermediate platform segments enter the internal track, their segment links are unrestrained from the aligned position.

47. The transfer device of claim 46, further comprising a transfer device controller configured to control the articulated transfer platform.

* * * * *